United States Patent
Duke et al.

(10) Patent No.: US 10,696,615 B2
(45) Date of Patent: *Jun. 30, 2020

(54) PRENYLATED HYDROXYSTILBENES

(71) Applicant: The University of Sydney, Sydney, NSW (AU)

(72) Inventors: Colin Charles Duke, Randwick (AU); Van Hoan Tran, Guildford (AU); Rujee Kyokajee Duke, Randwick (AU)

(73) Assignee: The University of Sydney, Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/221,666

(22) Filed: Dec. 17, 2018

(65) Prior Publication Data
US 2019/0194105 A1 Jun. 27, 2019

Related U.S. Application Data

(63) Continuation of application No. 14/115,574, filed as application No. PCT/AU2012/000482 on May 4, 2012, now Pat. No. 10,196,335.

(30) Foreign Application Priority Data

May 4, 2011 (AU) ................................ 2011901663

(51) Int. Cl.
| | | |
|---|---|---|
| *C07C 43/253* | (2006.01) | |
| *C07C 39/21* | (2006.01) | |
| *C07C 43/23* | (2006.01) | |
| *C07C 37/055* | (2006.01) | |
| *C07C 39/215* | (2006.01) | |
| *C07C 41/01* | (2006.01) | |
| *C07C 67/293* | (2006.01) | |
| *C07C 67/297* | (2006.01) | |

(52) U.S. Cl.
CPC .......... *C07C 43/253* (2013.01); *C07C 37/055* (2013.01); *C07C 39/21* (2013.01); *C07C 39/215* (2013.01); *C07C 41/01* (2013.01); *C07C 43/23* (2013.01); *C07C 67/293* (2013.01); *C07C 67/297* (2013.01)

(58) Field of Classification Search
CPC ..... C07C 37/055; C07C 39/21; C07C 39/215; C07C 41/01; C07C 43/23; C07C 43/253; C07C 67/293; C07C 67/297; A61K 31/09; A61K 31/05; A61P 35/00
See application file for complete search history.

(56) References Cited

U.S. PATENT DOCUMENTS

| | | | |
|---|---|---|---|
| 9,340,477 B2 | 5/2016 | Kishi et al. | |
| 10,196,335 B2 * | 2/2019 | Duke | C07C 39/21 |
| 2003/0125377 A1 | 7/2003 | Kinghom et al. | |
| 2013/0310611 A1 | 11/2013 | Kishi et al. | |

FOREIGN PATENT DOCUMENTS

| | | |
|---|---|---|
| CN | 1566054 A | 1/2005 |
| CN | 1736986 A | 2/2006 |
| CN | 101070274 A | 11/2007 |
| GB | 2411353 A | 8/2005 |
| JP | H07-17859 A | 1/1995 |
| JP | 2005505519 A | 2/2005 |
| KR | 20030011980 A | 2/2003 |
| WO | WO 03/009807 A2 | 2/2003 |
| WO | WO 03/010121 A1 | 2/2003 |
| WO | WO 2009/012910 A1 | 1/2009 |

OTHER PUBLICATIONS

Abu-Mellal et al., "Prenylated cinnamate and stilbenes from Kangaroo Island propolis and their antioxidant activity", 2012, Phytochemistry, vol. 77, pp. 251-259. (Available online Feb. 8, 2012). (Year: 2012).*
Abdel-Mogib et al.; "Stilbenes and a New Acetophenone Derivative from *Scirpus holoschoenus*;" Molecules; (Jul. 31, 2001); pp. 663-667; vol. 6.
Aguamah et al.; "Two Novel Stilbene Phytoalexins from *Arachis hypogaea*;" Phytochemistry; (1981); pp. 1381-1383; vol. 20, No. 6.
Aritomi et al.; "Stilbene Glucosides in the Bark of Picea Sitchensis;" Phytochemistry; (1976); pp. 2006-2008; vol. 15, Issue 12; <doi: 10.1016/S0031-9422(00)88881-0 >; [abstract].
Asakawa et al.; "Novel Bibenzyl Derivaties and Ent-Cuparene-Type Sesquiterpenoids from Radula Species;" Phytochemistry; (1982); pp. 2481-2490; vol. 21, No. 10.
Biondi et al.; "Dihydrostilbene Derivaties from *Glycyrrhiza glabra* Leaves;" Journal of Natural Products; (2005); pp. 1099-1102; vol. 68, No. 7; <doi: 10.1021/np050034q >.

(Continued)

*Primary Examiner* — My-Chau T. Tran
(74) *Attorney, Agent, or Firm* — Thorpe North & Western, LLP

(57) ABSTRACT

A method for treating cancer can include administering a therapeutically effective amount of a compound of formula (Ia):

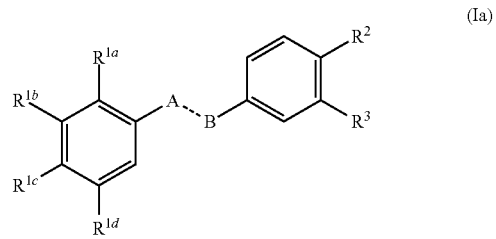

or pharmaceutically acceptable salts or solvates thereof, wherein $R^{1a}$, $R^{1b}$, $R^{1c}$, $R^{1d}$, $R^2$, and $R^3$ are as defined, and A----B is selected from CH=CH, CH=CH(CH$_2$)$_p$CH$_2$, or CH$_2$—CH$_2$(CH$_2$)pCH$_2$, and where p is 1 or 2.

25 Claims, 11 Drawing Sheets

(56) References Cited

OTHER PUBLICATIONS

Biondi et al.; "New Dihydrostilbene Derivaties from the Leaves of *Glycyrrhiza glabra* and Evaluation of their Antioxidant Activity;" (2003); pp. 477-480; vol. 66, No. 4; <doi: 10.1021/np020365s >.
Boonlaksiri et al.; "An Antimalarial Stilbene from *Artocarpus integer*;" Phytochemistry; (2000); pp. 415-417; vol. 54.
CAS Registry No. 1028254-67-2; Entered STN: Jun. 15, 2008.
CAS Registry No. 1083192-76-0, Entered STN: Dec. 12, 2008.
CAS Registry No. 1136618-10-4, Entered STN: Apr. 19, 2009.
CAS Registry No. 134958-54-6; Entered STN: Jul. 19, 1991.
CAS Registry No. 494411-23-9; Entered STN: Feb. 27, 2003.
CAS Registry No. 945919-58-4; Entered STN: Aug. 31, 2007.
CAS Registry No. 945919-59-5; Entered STN: Aug. 31, 2007.
CAS Registry No. 945919-60-8; Entered STN: Aug. 31, 2007.
CAS Registry No. 945919-61-9; Entered STN: Aug. 31, 2007.
CAS Registry No. 959120-57-1; Entered STN: Dec. 20, 2007.
Database Reaxys; Database Accession No. 7355532; Reaxys Registry No. 7355532, 7355111; [online]; (Upon Belief and Knowledge Accessed on or About Nov. 3, 2014); 2 pages; Elsevier.
Database WPI; Week 200575; AN 2005-726141; (Upon Knowledge and Belief Accessed on or About Nov. 3, 2014); 1 page; Thomson Scientific, London, GB.
Djoko et al.; "Characterization of Immunological Activities of Peanut Stilbenoids, Arachidin-1, Piceatannol, and Resveratrol on Lipopolysaccharide-Induced Inflammation of RAW 264.7 Macrophages;" Journal of Agricultural and Food Chemistry; (2007); pp. 2376-2383; vol. 55, No. 6; <doi: 10.1021/jf062741a >.
Ehrman et al.; "In Silico Search for Multi-Target Anti-Inflammatories in Chinese Herbs and Formulas;" Bioorganic & Medicinal Chemistry; (2010); pp. 2204-2218; vol. 18, No. 6; <doi: 10.1016/j.bmc.2010.01.070 >.
Fukai et al.; "Cytotoxic Activity of Low Molecular Weight Polyphenols Against Human Oral Tumor Cell Lines;" Anticancer Research; (Jul.-Aug. 2000); pp. 2525-2536; vol. 20, No. 4; International Institute of Anticancer Research.
Fukai et al.; "Phenolic Constituents of Glycyrrhiza, Part 6: Six Prenylated Phenols from *Glycyrrhiza uralensis*;" Phytochemistry; (1991); pp. 1245-1250; vol. 30, No. 4.
Hakim et al.; "Artoindonesianins N and O, New Prenylated Stilbene and Prenylated Arylbenzofuran Derivatives from *Artocarpus gomezianus*;" Fitoterapia; (2002); pp. 597-603; vol. 73.
Huang et al.; "Arachidin-1, a Peanut Stilbenoid, Induces Programmed Cell Death in Human Leukemia HL-60 Cells;" Journal of Agricultural and Food Chemistry; (Nov. 10, 2010); pp. 12123-12129; vol. 58; <doi: 10.1021/jf102993 >.
Ito et al.; "Synthetic Cinnamylphenol Derivatives as Cancer Chemopreventive Agents;" European Journal of Medicinal Chemistry; (Jul. 2007); pp. 902-909; vol. 42; doi: 10.1016/j.ejmech.2006.12.024 >.
Jayasinghe et al.; "Stilbene Derivatives with Antifungal and Radical Scavenging Properties from the Stem Bark of *Artocarpus nobilis*;" Natural Product Research; (Dec. 2004); pp. 571-574; vol. 18, No. 6; <doi: 10.1080/14786410310001643867 >.
Kim et al.; "Oxyresveratrol and Hydroxystilbene Compounds: Inhibitory Effect on Tyrosinase and Mechanism of Action;" The Journal of Biological Chemistry; (May 3, 2002); pp. 16340-16344; vol. 277, No. 18; <doi: 10.1074/jbc.M200678200 >.
Kusano et al.; "Studies on Index Compounds for HPLC Analysis of *Glycyrrhiza flavescens* Growing in Turkey;" Natural Medicines; (2002); pp. 129-135; vol. 56, No. 4.
Lee et al.; "Induction of Apoptosis by 3,4'-Dimethoxy-5-Hydroxy-Stilbene in Human Promyeloid Leukemic HL-60 Cells;" Planta Medica; (2002); pp. 123-127; vol. 68, No. 2.

Likhitwitayawuid; "Stilbenes with Tyrosinase Inhibitory Activity;" Current Science; (Jan. 10, 2008); pp. 44-52; vol. 94, No. 1.
Mouihate et al.; "Oxyresveratrol Dampens Neuroimmune Responses in Vivo: A Selective Effect on TNF- α;" American Journal of Physiology—Regulatory, Integrative and Comparative Physiology; (Jun. 29, 2006); pp. R1215-R1221; vol. 291; <doi: 10.1152/ajpregu.00250.2006 >.
Munigunti et al.; "Screening of Natural Compounds for Ligands to P $f$TrxR by Ultrafiltration and LC-MS Based Binding Assay;" Journal of Pharmaceutical and Biomedical Analysis; (2011); pp. 265-271; vol. 55; <doi: 10.1016/j.jpba.2011.01.033 >.
Murias et al.; "Antioxidant, Prooxidant and Cytotoxic Activity of Hydroxylated Resveratrol Analogues: Structure-Activity Relationship;" Biochemical Pharmacology; (2005); pp. 903-912; vol. 69; <doi: 10.1016/j.bcp.2004.12.001 >.
Nomura et al.; "Chemistry of Phenolic Compounds of Licorice (*Glycyrrhiza* Species) and their Estrogenic and Cytotoxic Activities;" Pure and Applied Chemistry; (2002); pp. 1199-1206; vol. 74, No. 7.
Orsini et al.; "Resveratrol Derivatives and Their Role as Potassium Channels Modulators;" Journal of Natural Products; (Feb. 20, 2004); pp. 421-426; vol. 67; <doi: 10.1021/np0303153 >.
Patel et al.; "Inhibition of Cyclo-Oxygenase-2 Expression in Mouse Macrophages by 4-(3-Methyl-but-1-Eny1)-3,5,3',4'-Tetrahydroxystilbene, a Resveratrol Derivative from Peanuts;" Phytotherapy Research; (2005); pp. 552-555; vol. 19; <doi: 10.1002/ptr.1698 >.
Sato et al.; "Erythrina Poeppigiana-Derived Phytochemical Exhibiting Antimicrobial Activity Against *Candida albicans* and Methicillin-Resistant *Staphylococcus aureus*;" Letters in Applied Microbiology; (Jun. 13, 2003); pp. 81-85; vol. 37, Issue 1; <doi: 10.1046/j.1472-765X.2003.01352.x >.
Siracusa et al.; "Phytocomplexes from Liquorice (*Glycyrrhiza glabra* L.) Leaves—Chemical Characterization and Evaluation of their Antioxidant, Anti-Genotoxic and Anti-Inflammatory Activity;" Fitoterapia; (2011); pp. 546-556; vol. 82; <doi: 10.1016/j.fitote.2011.01.009 >.
Sobolev et al.; "Biological Activity of Peanut (*Arachis hypogaea*) Phytoalexins and Selected Natural and Synthetic Stilbenoids;" Journal of Agricultural and Food Chemistry; (Feb. 11, 2011); pp. 1673-1682; vol. 59, No. 5; <doi: 10.1021/jf104742n >.
Sobolev et al.; "New Peanut (*Arachis hypogaea*) PHytoalexin with Prenylated Benzenoid and But-2-Enolide Moieties;" Journal of Agricultural and Food Chemistry; (Feb. 16, 2006); pp. 2111-2115; vol. 54; <doi: 10.1021/jf052948o >.
Sobolev et al.; "New Stilbenoids from Peanut (*Arachis hypogaea*) Seeds Challenged by an Aspergillus Caelatus Strain;" Journal of Agricultural and Food Chemistry; (Dec. 8, 2008); pp. 62-68; vol. 57; <doi: 10.1021/jf802891v >.
Sobolev et al.; "Prenylated Stilbenes from Peanut Root Mucilage;" Phytochemical Analysis; (Jun. 30, 2006); pp. 312-322; vol. 17; <doi: 10.1002/pca.920 >.
Su et al.; "Constituents of the Bark and Twigs of *Artocarpus dadah* with Cyclooxygenase Inhibitory Activity;" Journal of Natural Products; (Jan. 25, 2002); pp. 163-169; vol. 65; <doi: 10.1021/np010451c>.
Tanaka et al.; "Prenylated Cinnamylphenols, HIV-1 Replication Inhibitors, from Erythrina Poeppigiana;" ITE Letters on Batteries, New Technologies & Medicine; (2002); pp. 612-615; vol. 3, No. 5.
Wang et al.; "Prenylated Stilbenes and Their Novel Biogenetic Derivatives from *Artocarpus chama*;" European Journal of Organic Chemistry; (2006); pp. 3457-3463; <doi: 10.1002/ejoc.200600278 >.
Zhang et al.; "QSAR Study of Cinnamylphenol Derivatives as EBV-EA Inhibitors;" Computers and Applied Chemistry; (2009); pp. 1598-1602; vol. 26, No. 12.

* cited by examiner

PRENYLATED HYDROXYSTILBENES

CROSS-REFERENCE TO RELATED APPLICATIONS

The present application claims priority to U.S. patent application Ser. No. 14/115,574, filed on Nov. 4, 2013, which is a national stage application of PCT/AU2012/000482, filed on May 4, 2012, which claims the benefit of Australian Patent Application AU2011901663, filed on May 4, 2011, each of which is incorporated herein by reference.

TECHNICAL FIELD

This invention relates to novel prenylated stilbene compounds and to the use of such compounds in the treatment of diseases and medical disorders, for example cancer and skin aging.

BACKGROUND OF THE INVENTION

Propolis, or so called bee glue, is a complex resinous substance collected by worker honey bees (*Apis mellifera*) from exudates and secretions of young shoots and buds from certain trees and shrubs. It is used by the bees to seal cracks and holes in their hives, and protect against microbial infections.

Propolis is a rich source of bioactive substances, and the medicinal use of propolis dates back to ancient civilizations. Currently, propolis is extensively available as a natural health product, and is widely used in cosmetics. However, its modem use in medicine is limited, largely due to the wide variations in chemical compositions arising from honey bees collecting from different or a mixture of plant sources. The composition of propolis is dependent upon the surrounding flora to which the bees have access, and as such, differences in flora may result in differences in propolis compositions. For example, it is known that flavonoids are the major pharmacologically active compounds in European propolis, polyprenylated benzophenones are the main substances in Cuban and Venuzuelan propolis, and prenylated cinnamic acid derivatives are predominant in Brazilian propolis.

Recognition of the botanical origin of the propolis produced by honey bees enables beehives to be placed in favourable locations such that propolis from a single botanical source may be produced to enable manufacture of medicines of high quality and efficacy.

The medicinal uniqueness of propolis is determined by the selective collecting ability of honey bees, as they can recognise natural materials that are relatively non-polar and have antibiotic properties. As reported, the common source of propolis is leaf and flower bud exudates, which are of high antibiotic character in order to protect the delicate growing of plant tissue from attack by microorganisms. It has also been reported that honey bees collect exudates from wounded or diseased plant tissues. Such sources are potentially rich in antibiotic substances produced by plants in response to wounding or attack from insects, microorganisms and viruses.

It is not clear from previous studies whether the bees simply collect a plant material that is known as propolis, or if there is metabolic modification or addition from the bees. However, there does not appear to be evidence of significant amounts of material added from honey bees, or strong evidence for metabolic transformation.

Thus, a better understanding is required regarding the composition of propolis in specific geographical locations to be able to utilize it to its full benefit.

In work leading up to the present invention the inventors have conducted a survey of propolis samples isolated from Kangaroo Island (South Australia), and surprisingly found that unlike other propolis which commonly contain flavonoids as active constituents, Kangaroo Island propolis contain stilbenes, more particularly novel prenylated polyhydroxystilbenes (pPHOS) which are similar in their core structure to resveratrol (pictured below).

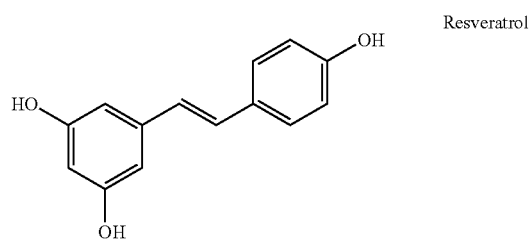 [SMILES: Oc1ccc(/C=C/c2cc(O)cc(O)c2)cc1]

Resveratrol is the constituent in red wine thought to contribute to the low incidence of heart attack amongst the French despite high consumption of very rich food. In fact, Resveratrol has been shown to inhibit LDL oxidation which leads to atherosclerosis and coronary heart disease. Resveratrol is also a lead compound in preventative anti-ageing medicine, and has also been found to possess anti-cancer and antioxidant activities.

However, despite its therapeutic properties, resveratrol exhibits very poor oral bioavailability and is rapidly metabolized in the intestines and liver into glucuronate and sulfate conjugates. The in vivo effectiveness of resveratrol is only observed at high concentrations (up to 5 g), or in the case of direct administration such as intravenous or local application.

Recently, GlaxoSmithKline (GSK) Pharmaceutical conducted phase IIa clinical trials of its proprietary formulation of resveratrol (3-5 g), SRT501 in the treatment of multiple myeloma; however, the trials were halted as the formulation only offered minimal efficacy, and several patients in the trial developed kidney failure.

Prenylated hydroxystilbenes have been reported in plants, mainly from the Moraceae (Mulberry family, including *Morus alba* (mulberry), and various *Artocarpus* species) and Fabaceae (Legume family, including *Arachis hypogaea* (peanut)) families. The isolated compounds have reportedly exhibited anti-inflammatory, antimicrobial and antioxidant activities, thus suggesting that the prenyl group does not adversely affect the biological activities of hydroxystilbenes.

In fact, prenylated hydroxystilbenes could circumvent the problem of low bioavailability of hydroxystilbenes, such as resveratrol, due to their lipophilic nature. Owing to the presence of one or more prenyl groups, the compounds may be able to cross cell membranes more readily and the formation of glucuronate and sulfate conjugates may be avoided, thus improving the bioavailability of the compounds, and more generally presenting superior drug candidates for the development of new therapeutic agents. Previously, it has been demonstrated that a tetramethoxy derivative of resveratrol was able to cross the blood-brain barrier in rats more easily than resveratrol.

Thus, the novel pPHOS derivatives isolated from the propolis samples of Kangaroo Island are strong candidates for the development of new therapeutic agents in the treatment of diseases such as cancer.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

SUMMARY

In work leading up to the present invention the inventors have isolated and synthesised a number of novel prenylated polyhydroxystilbenes (pPHOS) derivatives, and carried out in vitro experiments in which these novel compounds have exhibited high potency and selectivity in a panel of cancer cell lines, particularly in leukemia and melanoma cell lines. In other preliminary experiments, a number of the novel pPHOS derivatives were found to modulate activity of the SIRT1 enzyme which indicate that the novel pPHOS compounds of the present invention may be lead therapeutic agents for the treatment of a range of diseases.

Accordingly, in a first aspect of the invention, there is provided a method for treating cancer comprising administering a therapeutically effective amount of a compound of formula (I),

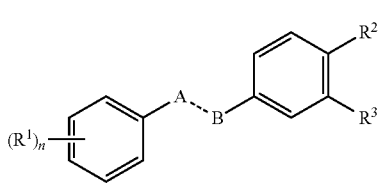

wherein:
$R^1$ is independently H, OH, $OR^4$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$, wherein at least one of $R^1$ is $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;
$R^2$ is selected from OH, $OR^4$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;
$R^3$ is selected from H, OH, $OR^4$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;
$R^4$ is selected from, methyl, ethyl, propyl, isopropyl, butyl, isobutyl, t-butyl or benzyl;
n is an integer selected from the group consisting of 1, 2, 3 or 4;
and A----B is selected from CH=CH, $CH_2$—$CH_2$, CH=CHX, or $CH_2$—$CH_2X$, where X=$(CH_2)pCH_2$, and p is an integer selected from the group consisting of 0, 1, 2 or 3; provided that when $R^2$ is OH, $R^3$ is H or OH, A----B is CH=CH, n is 3 and two of the $R^1$ groups are OH, then the third $R^1$ group is not $CH=CHCH(CH_3)_2$;
or a pharmaceutically acceptable salt, solvate, or pharmaceutical composition including said compounds, to a patient in need thereof.

In a second aspect of the invention, there is provided a method for treating cancer comprising administering a therapeutically effective amount of a compound of formula (I),

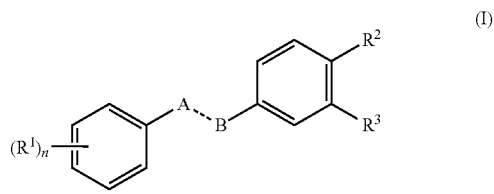

wherein:
$R^1$ is independently H, OH, $OR^4$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$, wherein at least one of $R^1$ is $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;
$R^2$ is selected from OH, $OR^4$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;
$R^3$ is selected from H, OH, $OR^4$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;
$R^4$ is selected from, methyl, ethyl, propyl, isopropyl, butyl, isobutyl, t-butyl or benzyl;
n is an integer selected from the group consisting of 1, 2, 3 or 4;
and A----B is selected from CH=CH, $CH_2$—$CH_2$, CH=CHX, or $CH_2$—$CH_2X$, where X=$(CH_2)pCH_2$, and p is an integer selected from the group consisting of 0, 1, 2 or 3;
or a pharmaceutically acceptable salt, solvate, or pharmaceutical composition including said compounds, to a patient in need thereof.

In a third aspect, there is provided a compound of formula (I) according to the first or second aspects, or pharmaceutical composition thereof, for use as a medicament.

In a fourth aspect, there is provided a compound of formula (I) according to the first or second aspects, or pharmaceutical composition thereof, for use in therapy.

In a fifth aspect of the invention there is provided a compound of formula (I) according to the first or second aspects, or pharmaceutical composition thereof, for use in the treatment of cancer.

In a sixth aspect of the invention, there is provided a method for treating immunosuppression comprising administering a therapeutically effective amount of a compound of formula (I) according to the first or second aspects, or a pharmaceutical composition including said compounds to a patient in need thereof.

In a seventh aspect of the invention, there is provided a method for treating inflammation comprising administering a therapeutically effective amount of a compound of formula (I) according to the first or second aspects, or a pharmaceutical composition including said compounds to a patient in need thereof.

In an eighth aspect of the invention, there is provided a method for treating a bacterial or fungal infection comprising administering a therapeutically effective amount of a compound of formula (I) according to the first or second aspects, or a pharmaceutical composition including said compounds to a patient in need thereof.

In a ninth aspect of the invention, there is provided a method for treating skin aging comprising administering a therapeutically effective amount of a compound of formula (I) according to the first or second aspects, or a pharmaceutical composition including said compounds to a patient in need thereof.

In a tenth aspect of the invention, there is provided a use of a compound of formula (I) according to the first or second aspects, or a pharmaceutical composition thereof in the preparation of a medicament for the treatment of cancer.

In an eleventh aspect of the invention, there is provided a use of a compound of formula (I) according to the first or second aspects, or a pharmaceutical composition thereof in the preparation of a medicament for the treatment of immunosuppression.

In a twelfth aspect of the invention, there is provided a use of a compound of formula (I) according to the first or second aspects, or a pharmaceutical composition thereof in the preparation of a medicament for the treatment of inflammation.

In a thirteenth aspect of the invention, there is provided a use of a compound of formula (I) according to the first or second aspects, or a pharmaceutical composition thereof in the preparation of a medicament for the treatment of a bacterial or fungal infection.

In a fourteenth aspect of the invention, there is provided a use of a compound of formula (I) according to the first or second aspects, or a pharmaceutical composition thereof in the preparation of a medicament for the treatment of skin aging.

In further aspects of the invention, there is provided combinations comprising a compound or pharmaceutical composition as defined above, and at least one further therapeutic agent for the methods and uses as described herein.

According to a fifteenth aspect of the invention, there is provided a compound of formula (Ia)

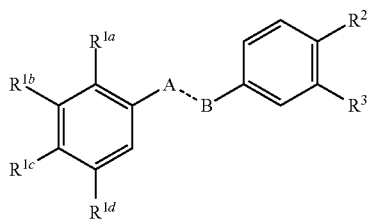

(Ia)

or a pharmaceutically acceptable salt or solvate thereof, wherein:

$R^{1a}$, $R^{1b}$, $R^{1c}$ and $R^{1d}$ are each independently H, OH, $OR^4$, $CH_2CH=C(CH_3)_2$, $OCH_2CH=C(CH_3)_2$, $CH=CHC(CH_3)=CH_2$, $OCH=CHCH(CH_3)_2$, or $OCH=CHC(CH_3)=CH_2$, wherein at least one of $R^{1a-1d}$ is $CH_2CH=C(CH_3)_2$, $OCH_2CH=C(CH_3)_2$, $CH=CHC(CH_3)=CH_2$, $OCH=CHCH(CH_3)_2$, or $OCH=CHC(CH_3)=CH_2$;

$R^2$ is selected from OH, $OR^4$, $CH_2CH=C(CH_3)_2$, $OCH_2CH=C(CH_3)_2$, $CH=CHC(CH_3)=CH_2$, $OCH=CHCH(CH_3)_2$, or $OCH=CHC(CH_3)=CH_2$;

$R^3$ is selected from H, OH, $OR^4$, $CH_2CH=C(CH_3)_2$, $OCH_2CH=C(CH_3)_2$, $CH=CHC(CH_3)=CH_2$, $OCH=CHCH(CH_3)_2$, or $OCH=CHC(CH_3)=CH_2$;

$R^4$ is selected from, methyl, ethyl, propyl, isopropyl, butyl, isobutyl, t-butyl or benzyl;

and A----B is selected from CH=CH, $CH_2$—$CH_2$, CH=CHX, or $CH_2$—$CH_2X$, where X=$(CH_2)pCH_2$, and p is an integer selected from the group consisting of 0, 1, 2 or 3; provided that:

(i) when $R^3$ is H and $R^2$ is OH or $OCH_2CH=C(CH_3)_2$, then $R^{1b}$ and $R^{1d}$ are independently not OH or $OCH_2CH=C(CH_3)_2$;

(ii) when $R^3$ is H, one of $R^{1a-1d}$ is H and at least one of $R^{1a-1d}$ is $CH_2CH=C(CH_3)_2$, then A---B is not CH=CH.

In a sixteenth aspect of the invention, there is provided a compound of formula (Ia)

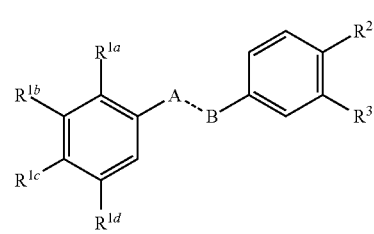

(Ia)

or a pharmaceutically acceptable salt or solvate thereof, wherein:

$R^{1a}$, $R^{1b}$, $R^{1c}$ and $R^{1d}$ are each independently H, OH, $OR^4$, $CH_2CH=C(CH_3)_2$, $OCH_2CH=C(CH_3)_2$, $CH=CHC(CH_3)=CH_2$, $OCH=CHCH(CH_3)_2$, or $OCH=CHC(CH_3)=CH_2$, wherein at least one of $R^{1a-1d}$ is $CH_2CH=C(CH_3)_2$, $OCH_2CH=C(CH_3)_2$, $CH=CHC(CH_3)=CH_2$, $OCH=CHCH(CH_3)_2$, or $OCH=CHC(CH_3)=CH_2$;

$R^2$ and $R^3$ are each independently selected from OH, $OR^4$, $CH_2CH=C(CH_3)_2$, $OCH_2CH=C(CH_3)_2$, $CH=CHC(CH_3)=CH_2$, $OCH=CHCH(CH_3)_2$, or $OCH=CHC(CH_3)=CH_2$;

$R^4$ is selected from, methyl, ethyl, propyl, isopropyl, butyl, isobutyl, t-butyl or benzyl;

and A----B is selected from CH=CH, $CH_2$—$CH_2$, CH=CHX, or —$CH_2$—$CH_2X$, where X=$(CH_2)pCH_2$ and p is an integer selected from the group consisting of 0, 1, 2 or 3.

In one specific example with respect to formula (Ia) or a pharmaceutically acceptable salt or solvate thereof:

$R^{1a}$ is selected from, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;

$R^{1b}$ is selected from, H, OH, $OR^4$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;

$R^{1c}$ is selected from H, OH, $OR^{4a}$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;

$R^{1d}$ is selected from H, OH, $OR^4$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;

wherein at least one of $R^{1b-1d}$ is OH and at least one of $R^{1a-1d}$ is $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;

$R^2$ is selected from OH, $OR^{4a}$, $OCH_2CH=C(CH_3)_2$, $CH=CHC(CH_3)=CH_2$, $OCH=CHCH(CH_3)_2$, or $OCH=CHC(CH_3)=CH_2$;

$R^3$ is selected from OH, $OR^4$, $OCH_2CH=C(CH_3)_2$, $CH=CHC(CH_3)=CH_2$, $OCH=CHCH(CH_3)_2$, or $OCH=CHC(CH_3)=CH_2$;

$R^4$ is selected from, methyl, ethyl, propyl, isopropyl, butyl, isobutyl, t-butyl or benzyl;

$R^{4a}$ is selected from, ethyl, propyl, isopropyl, butyl, isobutyl, t-butyl or benzyl; and A----B is selected from CH=CH, $CH=CH(CH_2)pCH_2$, or $CH_2-CH_2(CH_2)pCH_2$, where p is an integer selected from the group consisting of 1 and 2.

In a seventeenth aspect of the invention, there is provided a pharmaceutical composition comprising a compound of formula (Ia) according to the fifteenth or sixteenth aspects, or a pharmaceutically acceptable salt or solvate thereof, and a pharmaceutically acceptable excipient.

According to an eighteenth aspect, there is provided a method for treating cancer, immunosuppression, inflammation, bacterial infection, fungal infection or skin aging comprising administering a therapeutically effective amount of a compound of formula (Ia) according to the fifteenth or sixteenth aspects, or a pharmaceutical composition including said compounds to a patient in need thereof.

In a nineteenth aspect of the invention, there is provided a use of a compound of formula (Ia) according to the fifteenth or sixteenth aspects, or a pharmaceutical composition thereof in the preparation of a medicament for the treatment of cancer, immunosuppression, inflammation, bacterial infection, fungal infection or skin aging.

According to the twentieth aspect of the invention, there is provided a method of preparing compounds of formula (Ib) which comprises the following steps:

(i) treating the carboxylic acid with a suitable agent to provide the acid chloride as follows;

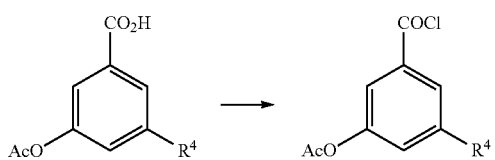

(ii) condensation of the corresponding acid chloride with an aryl alkene as follows;

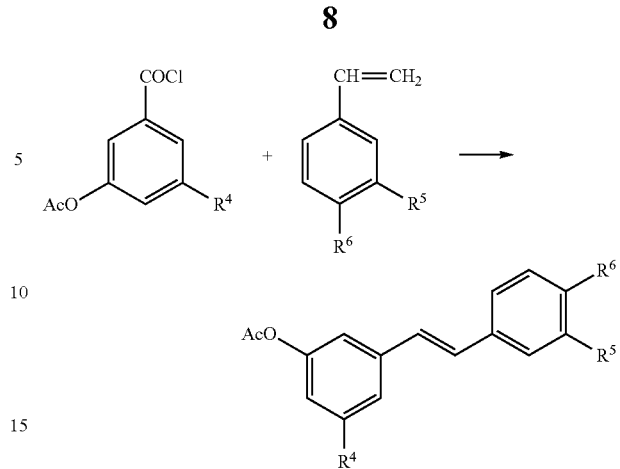

(iii) deprotection of the acetate group and alkylation as follows;

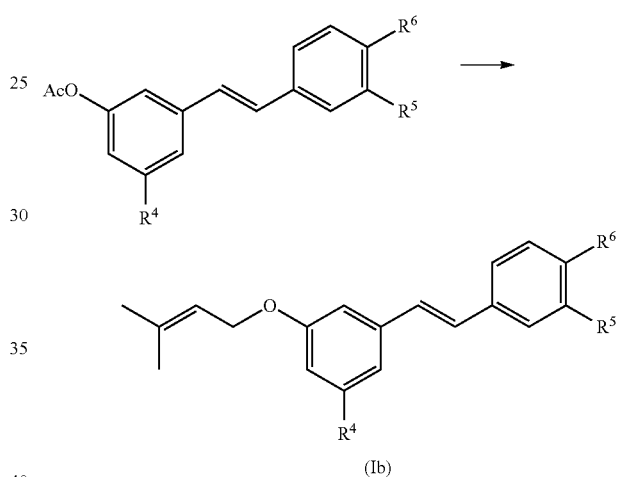

(Ib)

wherein, $R^4$, $R^5$ and $R^6$ are each independently selected from the group OMe, OEt, OPr, $O^iPr$, OBu, $O^iBu$, $O^tBu$, and OBn.

In this and other examples, as is conventionally understood in the context listed, Me is methyl, Et is ethyl, Pr is n-propyl, $^iPr$ is isopropyl, Bu is n-butyl, $^iBu$ is isobutyl, $^tBu$ is tert-butyl, and Bn is benzyl.

In one embodiment, the method comprises the additional step as follows:

(iv) a hydrogenation reaction as follows:

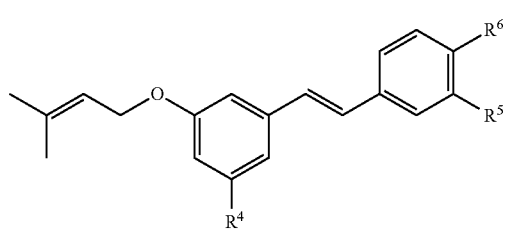

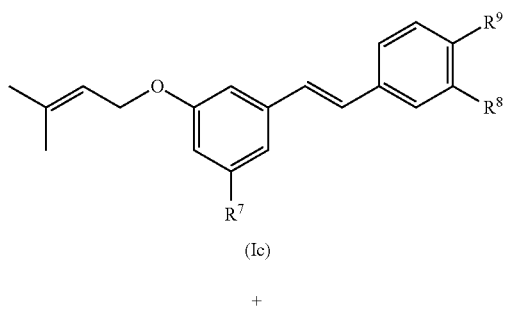

(Ic)

+

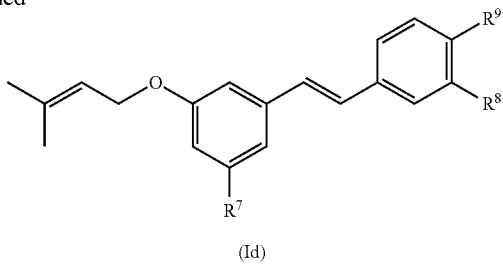

(Id)

wherein, $R^4$, $R^5$ and $R^6$ are as previously defined, provided that at least one of $R^4$, $R^5$ or $R^6$ is OBn;
$R^7$, $R^8$ and $R^9$ are each independently selected from the group consisting of OH, OMe, OEt, OPr, O$^i$Pr, OBu, O$^i$Bu, and O$^t$Bu.

In another embodiment the method comprises two additional steps as follows:
(v) rearrangement of the prenyl group as follows:

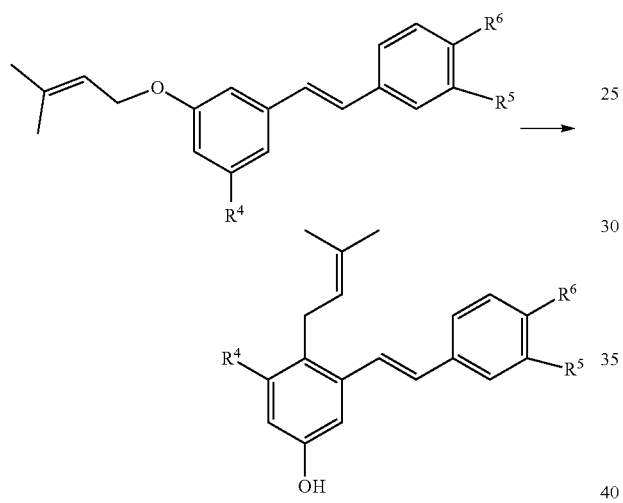

(vi) and a hydrogenation reaction as follows:

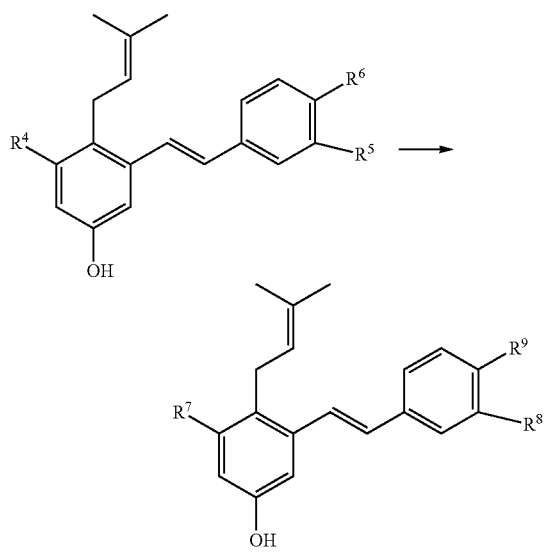

(Ie)

+

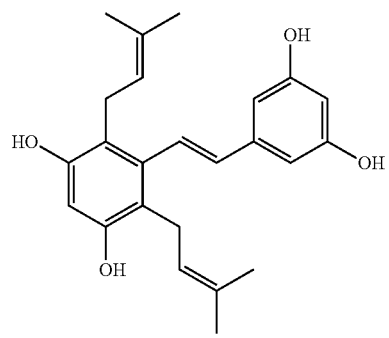

(If)

wherein, $R^4$, $R^5$ and $R^6$ are as previously defined, provided that at least one of $R^4$, $R^5$ or $R^6$ is OBn;
$R^7$, $R^8$ and $R^9$ are each independently selected from the group consisting of OH, OMe, OEt, OPr, O$^i$Pr, OBu, O$^i$Bu, and O$^t$Bu.

In a twenty first aspect of the invention, there is provided a compound according to USYDS15 as identified below

USYDS15

There is also provided a pharmaceutical composition comprising the compound USYDS15 according to the twenty first aspect, or a pharmaceutically acceptable salt or solvate thereof, and a pharmaceutically acceptable excipient.

In a twenty third aspect of the invention, there is provided use of the compound according to the twenty first aspect or the composition of the twenty second aspect, in the preparation of a medicament for the treatment of cancer, immunosuppresion, inflammation, fungal or bacterial infection, or for the treatment of skin aging.

DETAILED DESCRIPTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

While it is possible that, for use in therapy a therapeutically effective amount of the compounds as defined herein, or a pharmaceutically acceptable salt or solvate thereof, may be administered as the raw chemical; in one aspect of the present invention the active ingredient is presented as a pharmaceutical composition. Thus, in a further embodiment the invention provides a pharmaceutical composition comprising a compound of formula (I) or (Ia) according to the first, second, fifteenth and sixteenth aspects, or a pharmaceutically acceptable salt or solvate thereof, in admixture with one or more pharmaceutically acceptable carriers, diluents, or excipients. The carrier(s), diluent(s) or excipient(s) must be acceptable in the sense of being compatible with the other ingredients of the formulation and not deleterious to the recipient thereof.

When applicable, the compounds of the present invention, including the compounds of formula (I) or (Ia) may be in the form of and/or may be administered as a pharmaceutically acceptable salt.

As used herein the term "pharmaceutically acceptable salt" refers to salts which are toxicologically safe for systemic administration. The pharmaceutically acceptable salts may be selected from alkali or alkaline earth metal salts, including, sodium, lithium, potassium, calcium, magnesium and the like, as well as non-toxic ammonium, quaternary ammonium, or amine cations, including, but not limited to ammonium, tetramethylammonium, tetraethylammonium, methylamine, dimethylamine, trimethylamine, triethylamine, ethylamine, triethanolamine or the like.

As used herein the term "pharmaceutically acceptable excipient" refers to a solid or liquid filler, diluent or encapsulating substance that may be safely used in systemic administration. Depending upon the particular route of administration, a variety of carriers, well known in the art may be used. These carriers or excipients may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, or pyrogen-free water.

As used herein, the term "solvate" refers to a complex of variable stoichiometry formed by a solute (in this invention, a compound of formula (I) or (Ia) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. In particular the solvent used is a pharmaceutically acceptable solvent. Examples of suitable pharmaceutically acceptable solvents include, without limitation, water, ethanol, acetic acid, glycerol, liquid polyethylene glycols and mixtures thereof. A particular solvent is water.

Administration of compounds of the formula (I) or (Ia) may be in the form of a "prodrug". A prodrug is an inactive form of a compound which is transformed in vivo to the active form. Suitable prodrugs include esters, phosphonate esters etc, of the active form of the compound.

It should be understood that in addition to the ingredients particularly mentioned above, the formulations may include other agents conventional in the art having regard to the type of formulation in question.

The compounds of the present invention may be suitable for the treatment of diseases in a human or animal patient. In one embodiment, the patient is a mammal including a human, horse, dog, cat, sheep, cow, or primate. In one embodiment the patient is a human. In a further embodiment, the patient is not a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "treatment" refers to defending against or inhibiting a symptom, treating a symptom, delaying the appearance of a symptom, reducing the severity of the development of a symptom, and/or reducing the number or type of symptoms suffered by an individual, as compared to not administering a pharmaceutical composition comprising a compound of the invention. The term treatment encompasses the use in a palliative setting Those skilled in the art will appreciate that in the preparation of the compounds of the invention it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl).

According to the first, second or eighteenth aspects of the invention, the cancers to be treated are leukemia, non-small cell lung cancer, colon cancer, CNS cancer, melanoma, ovarian cancer, renal cancer, prostate cancer or breast cancer. Most preferably, the cancer to be treated is leukemia or melanoma.

In a preferred embodiments of the first to ninth aspects, the compound according to formula (I) has the formula (Ia).

According to the tenth or nineteenth aspect of the invention, preferably the medicament is used to treat the following cancers; leukemia, non-small cell lung cancer, colon cancer, CNS cancer, melanoma, ovarian cancer, renal cancer, prostate cancer or breast cancer. Most preferably, the medicament is used to treat leukemia or melanoma.

In preferred embodiments of the tenth to fourteenth aspects, the compound according to formula (I) has the formula (Ia).

The antitumor effect of the compounds of the present invention may be applied as a sole therapy or may involve, in addition, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer such as a combination of surgery, radiotherapy and/or chemotherapy. In particular, it is known that irradiation or treatment with antiangiogenic and/or vascular permeability reducing agents can enhance the amount of hypoxic tissue within a tumour. Therefore the effectiveness of the compounds of the present invention may be improved by conjoint treatment with radiotherapy and/or with an antiangiogenic agent.

The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of the compounds of this invention with other anti-neoplastic agents includes in principle any combination with any pharmaceutical composition useful for treating cancer.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

Pharmaceutical compositions of the invention may be formulated for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Therefore, the pharmaceutical compositions of the invention may be formulated, for example, as tablets, capsules, powders, granules, lozenges, creams or liquid preparations, such as oral or sterile parenteral solutions or suspensions. Such pharmaceutical formulations may be prepared by any method known in the art of pharmacy, for example by bringing into association the active ingredient with the carrier(s) or excipient(s). Such pharmaceutical formulations may be prepared as enterically coated granules, tablets or capsules suitable for oral administration and delayed release formulations.

When a compound is used in combination with a second therapeutic agent active against the same disease, the dose of each compound may differ from that when the compound is used alone. Appropriate doses will be readily appreciated by those skilled in the art.

In one embodiment of the invention according to the fifteenth aspect, there is provided a compound of formula (Ia) wherein $R^{1a}$-$R^{1d}$, $R^2$, $R^3$, $R^4$ and A----B are as hereinbefore defined provided that:
(i) when $R^3$ is H, then $R^{1b}$ and $R^{1d}$ are independently not OH or OCH$_2$CH=C(CH$_3$)$_2$; and
(ii) when $R^3$ is H, one of $R^{1a-1d}$ is H and at least one of $R^{1a-1d}$ is CH$_2$CH=C(CH$_3$)$_2$, then A---B is not CH=CH.

According to the fifteenth or sixteenth aspects, in preferred embodiments of the invention two of $R^{1a-1d}$ are H. In other preferred embodiments one of $R^{1a-1d}$ is H, and in other embodiments none of $R^{1a-1d}$ are H.

In a preferred embodiment, at least one of $R^{1a-1d}$ is CH$_2$CH=C(CH$_3$)$_2$, and in another preferred embodiment at least one of $R^{1a-1d}$ is OCH$_2$CH=C(CH$_3$)$_2$.

In certain embodiments at least one of $R^{1a-1d}$ is hydroxyl, and in certain other embodiments at least two of $R^{1a-1d}$ are hydroxyl. In another embodiment at least one of $R^{1a-1d}$ is OR$^4$ and $R^4$ is methyl, and in yet another embodiment $R^4$ is benzyl.

In preferred embodiments of the invention according to the fifteenth or sixteenth aspects, at least one of $R^2$ or $R^3$ is hydroxyl. In another preferred embodiment both $R^2$ and $R^3$ are hydroxyl.

In another embodiment at least one of $R^2$ or $R^3$ is OR$^4$ and $R^4$ is methyl, and in yet another embodiment $R^4$ is benzyl.

In preferred embodiments of the invention, the group A----B in formula (Ia) or is CH=CH or CH=CHX—, where X=(CH$_2$)pCH$_2$, and p is an integer selected from the group consisting of 0, 1, 2 and 3.

In other embodiments of the invention the group A----B in formula (Ia) is CH$_2$—CH$_2$, or CH$_2$—CH$_2$X, where X=(CH$_2$)pCH$_2$, and p is independently an integer selected from the group consisting of 0, 1, 2 and 3.

In a preferred embodiment, the compound of formula (Ia) according to the fifteenth or sixteenth aspect has the formula (Ib):

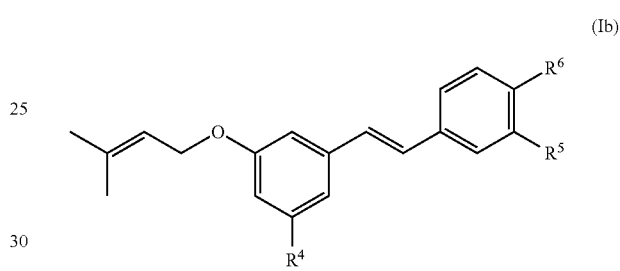

(Ib)

Wherein, $R^4$, $R^5$ and $R^6$ are each independently selected from the group consisting of OMe, OEt, OPr, O$^i$Pr, OBu, O$^i$Bu, O$^t$Bu, and OBn.

In another preferred embodiment the compound of formula (Ia) according to the fifteenth or sixteenth aspects has the formula (Ic) or (Id):

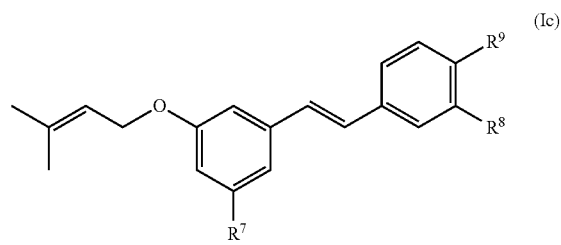

(Ic)

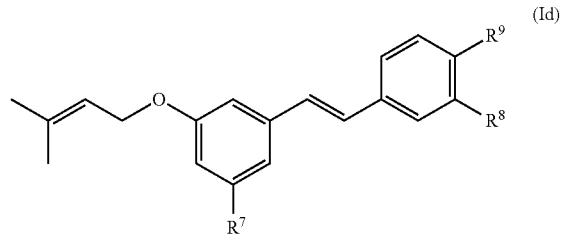

(Id)

Wherein, $R^7$, $R^8$ and $R^9$ are each independently selected from the group consisting of OH, OMe, -OEt, OPr, O$^i$Pr, OBu, O$^i$Bu, and O$^t$Bu.

In yet another preferred embodiment, the compound of formula (Ia) according to the fifteenth or sixteenth aspects has the formula (Ie) or (If)

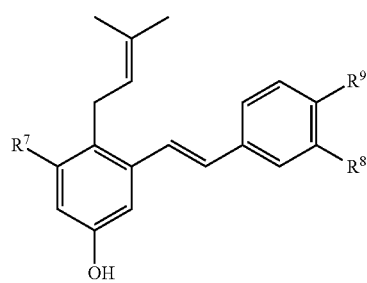
(1e)
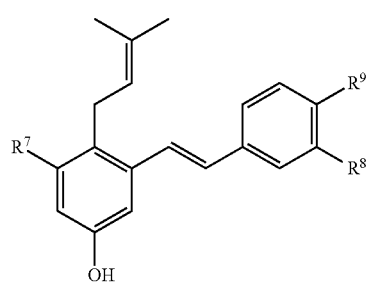
(1f)
Wherein, $R^7$, $R^8$ and $R^9$ are each independently selected from the group consisting of OH, OMe, OEt, OPr, O$^i$Pr, OBu, O$^i$Bu, and O$^t$Bu.
Preferably, the compound according to the fifteenth or sixteenth aspects, or pharmaceutically acceptable salt or solvate thereof is selected from the group consisting of:
USYDS1
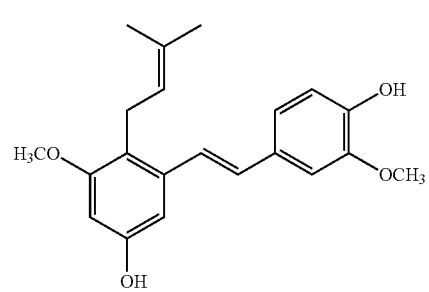
USYDS2
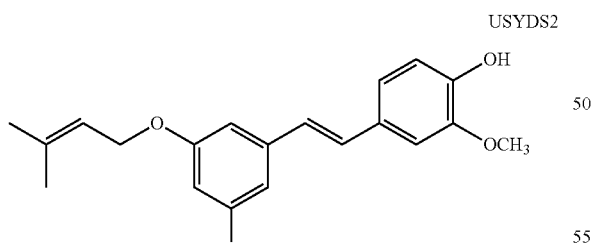
USYDS3
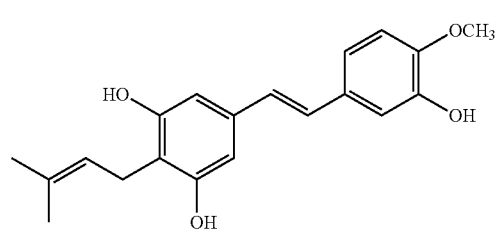
USYDS4
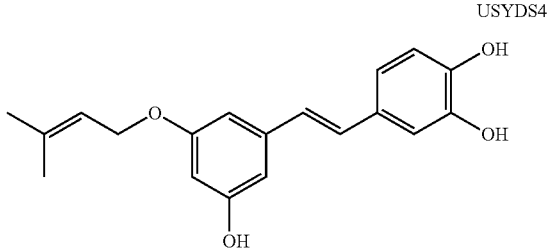
USYDS7
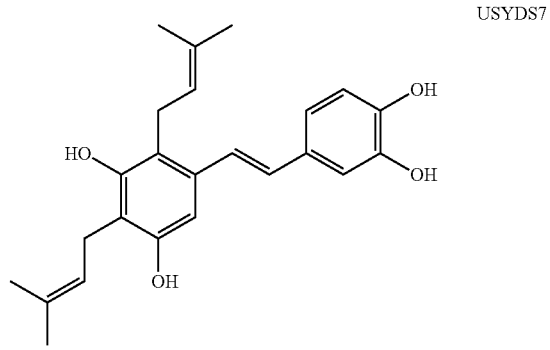
USYDS8
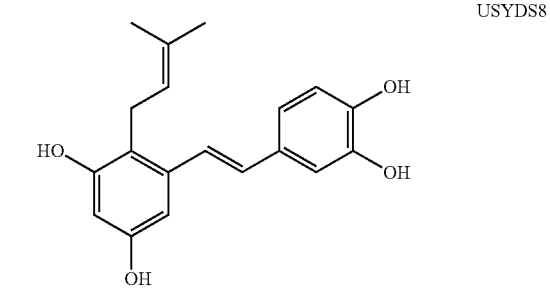
USYDS9
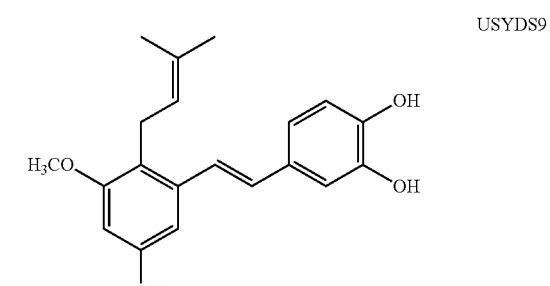
USYDS10
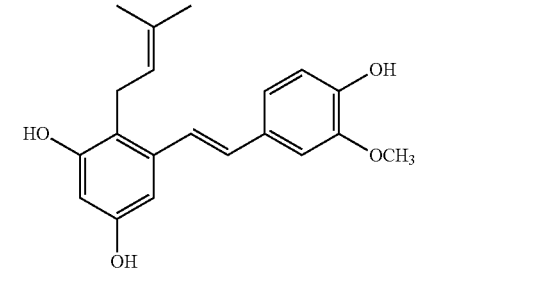

USYDS13
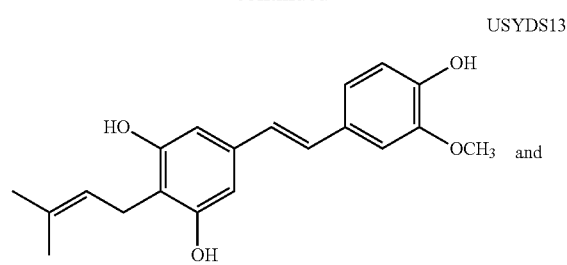
and
USYDS4
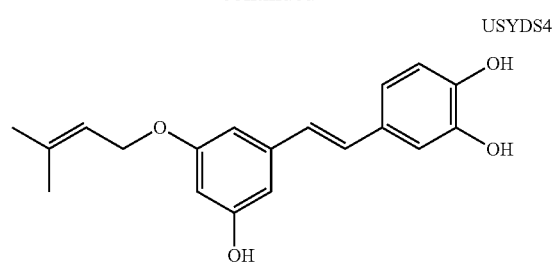 [SMILES: CC(C)=CCOc1cc(O)cc(/C=C/c2ccc(O)cc2)c1]
USYDS14
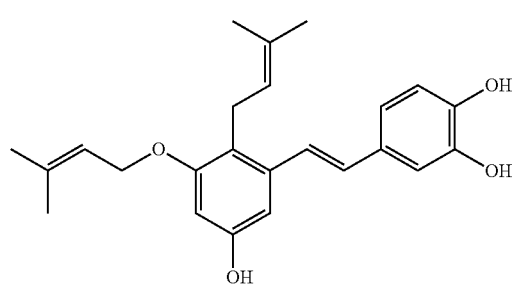
USYDS7
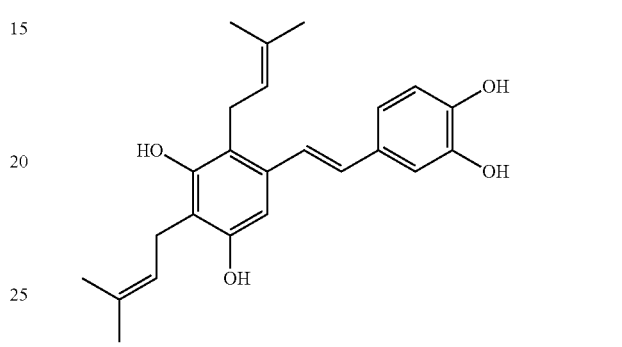
More preferably the compound according to the fifteenth or sixteenth aspects, or pharmaceutically acceptable salt or solvate thereof is selected from the group consisting of:
USYDS1
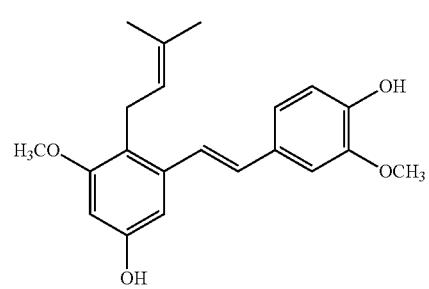
USYDS8
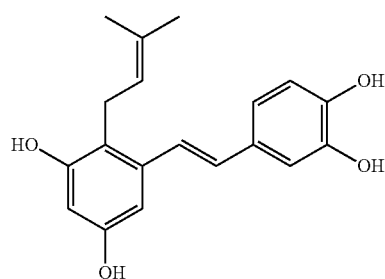
USYDS2
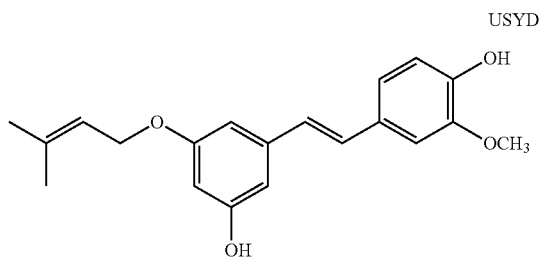
USYDS9
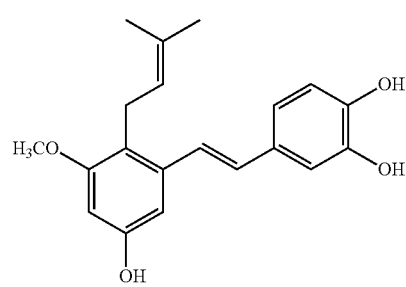
USYDS13
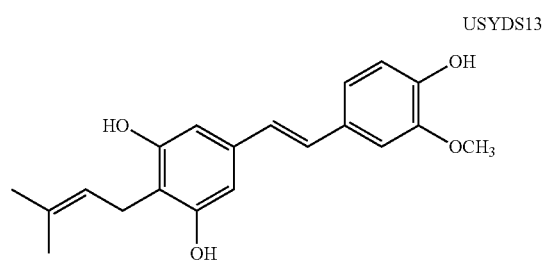
USYDS10
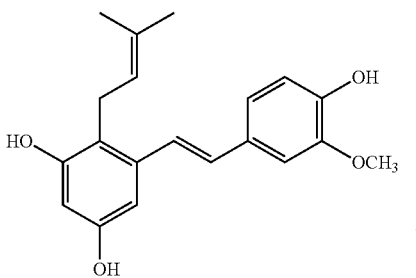
and -continued
USYDS14
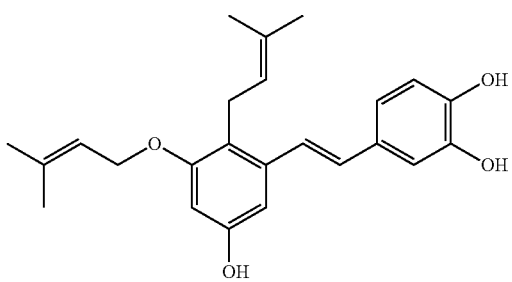
In one embodiment the compound according to the fifteenth or sixteenth aspects, or pharmaceutically acceptable salt or solvate thereof is selected from the group consisting of:
USYDS1
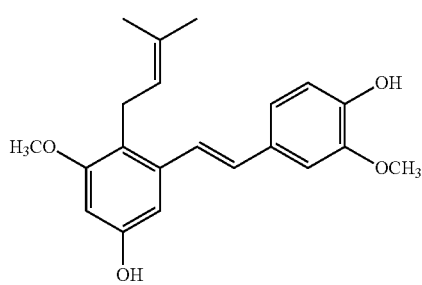
USYDS2
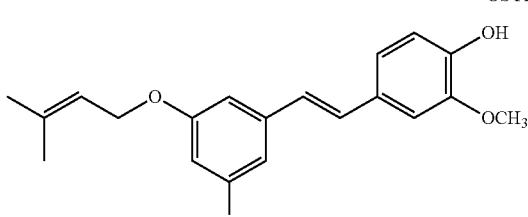
USYDS4
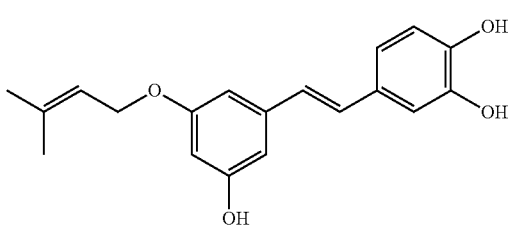
USYDS7
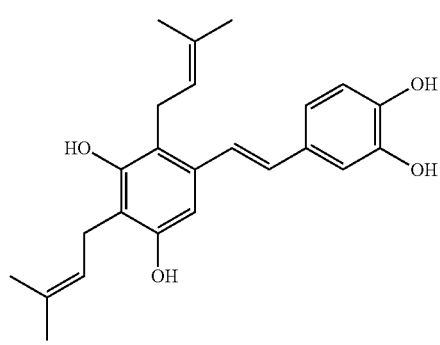
-continued
USYDS8
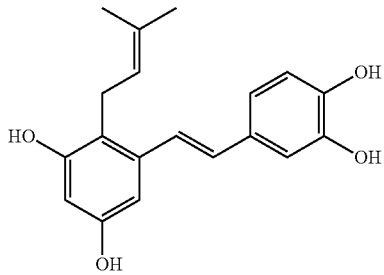
USYDS9
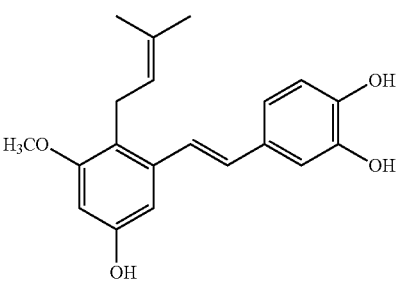
and
USYDS10
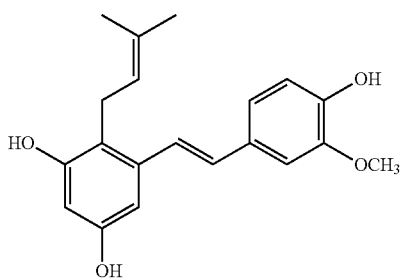
USYDS14
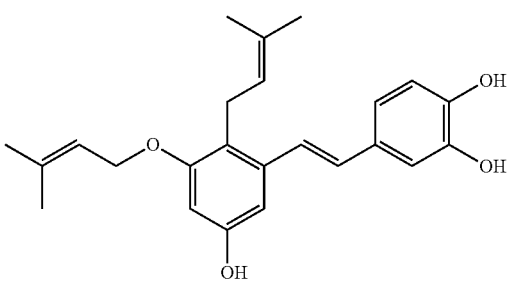
In another preferred embodiment the compound is USYDS18.
USYDS18
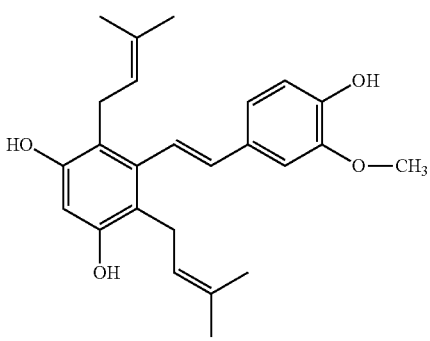

In another preferred embodiment, the compound according to the fifteenth aspect, or pharmaceutically acceptable salt or solvate thereof is selected from the group consisting of:

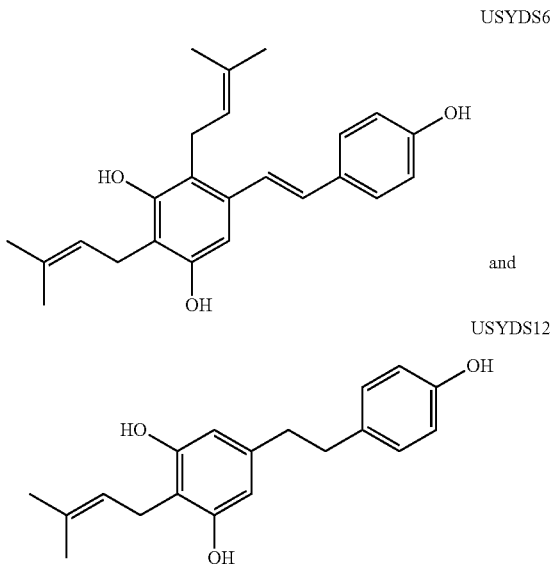

USYDS6 and

USYDS12

In preliminary in vitro assays to determine the anticancer activity of prenylated polyhydroxystilbene derivatives, the inventors observed structure dependent inhibition of cancerous cell growth for all derivatives, USYDS1 to USYDS7 and USYDS13. Most of these compounds, exhibited potent inhibition of almost all leukemia cell lines (CCRF-CEM, HL-60(TB), K-562, MOLT-4, RPMI-8226, SR). In some cell lines, growth was inhibited at nano-molar concentrations. USYDS1 displayed the most potent activity followed by USYDS10, USYDS9, USYDS2 then USYDS14 in the inhibition of cancerous cell growth. Structure dependent inhibition of cancerous cell growth for derivatives USYDS10 and 14 have also been observed. Structure-activity study shows the C-prenylation at the 2 position with the methoxy group at 3 position exhibits the highest potency towards inhibition of cancer cells.

Most of the pTHOS in this study have structures built on the piceatannol structure, a known naturally occurring compound, which displays a wide spectrum of biological activity. It is now attracting much attention on its anticancer properties because of its ability to inhibit proliferation of a wide variety of tumor cells, including leukemia, lymphoma; cancers of the breast, prostate, colon and melanoma. Its anticancer effects are suggested to mediate through cell-cycle arrest; upregulation of Bid, Bax, Bik, Bok, Fas; P21WAF1 down-regulation of Bcl-xL; BCL-2, cIAP, activation of caspases, loss of mitochondrial potential, and release of cytochrome c. Piceatannol has also been shown to inhibit the activation of some transcription factors, including NF-κB, which plays a central role in response to cellular stress caused by free radicals, ultraviolet irradiation, cytokines, or microbial antigens, JAK-1, a key transcription in the STAT pathway that controlling cellular activities in response to extracellular cytokines.

It has been observed that the pTHOS described in this study display a similar spectrum of biological activities to that exhibited by piceatannol. Furthermore, the pTHOS (ie. USYDS1, $GI_{50}$ values: 0.02 μM-5 μM) showed approximately 250 fold more potent than piceatannol ($IC_{50}$ values: 5 μM-100 μM) in inhibition of proliferation of almost all types of tumor cells. Therefore, the pTHOS present in this application will be an attractive lead for pharmaceutical research and development and as biological tools for further understanding the pathophysiology of cancer.

The potent cytotoxicity of compounds USYDS1 and compound USYDS2 may be explained in terms of their increased hydrophobicity, as demonstrated by their calculated Log partition coefficient (Log P) values. USYDS1 and USYDS2 have Log P values almost twice that of the hydroxystilbene resveratrol. The effects of Log P on therapeutic compounds relate primarily to tissue penetration and distribution. Higher Log P values will enable compounds to more easily cross cell membranes and enter cells.

In other preliminary experiments, particular examples of O- and C-prenylated hydroxystilbene derivatives were found to exhibit concentration dependent inhibition of the SIRT1 enzyme, a member of the Sirtuin family of proteins (silent information regulator two proteins, Sir 2).

Sirtuins have emerged as critical regulators for ageing and longevity in model organisms. Studies into genetics and physiology of sirtuins have shown that this enzyme family plays a role in a variety of cellular processes, including gene silencing, cell death, fatty acid metabolism, neuronal protection and life span extension.

Without being bound to any particular theory, it is proposed that modulation of SIRT1 activity could lead to the development of therapeutic agents for the treatment of diseases including cancer, metabolic syndrome, obesity, neurodegenerative disorder and aging-related diseases.

In a preferred embodiment, according to the fifteenth or sixteenth aspects the compound of formula (Ia) is chemically synthesised. In another preferred embodiment the compound of formula (Ia) is isolated from propolis, wherein the propolis originates from plants of the *Lepidosperma* genus. In yet another preferred embodiment, the compound of formula (Ia) is isolated from the resin, gum or exudate of the *Lepidosperma* genus.

According to the twentieth aspect of the invention, in the preparation of compounds of the formula (Ib), (Ic), (Id), (Ie) or (If), preferably the condensation reaction in step (ii) is carried out in the presence of a palladium catalyst. Preferably the palladium catalyst is palladium (II) acetate.

Preferably, the alkylation reaction in step (iii) is carried out in the presence of a metal hydride and a halogenated prenyl reagent. Preferably the metal hydride is sodium hydride; however, it would be appreciated by the person skilled in the art that other known metal hydrides can be used. Most preferably the halogenated prenyl reagent is $BrCH_2CH=C(CH_3)_2$.

In a preferred embodiment, the hydrogenation reaction in step (iv) or (vi) is carried out in the presence of a palladium catalyst in a mixture of solvents. Most preferably the palladium catalyst is palladium on carbon and the mixture of solvents comprises 1,4-cyclohexadiene and ethanol. However, it would be appreciated by the person skilled in the art that any other suitable reagents and solvents can be used.

In a preferred embodiment, the rearrangement reaction in step (v) is carried out in the presence of magnesium silicate particles (Florisil®), silica or alumina particles. In another preferred embodiment the rearrangement reaction can be carried out in the presence of microwave radiation or light. In yet another preferred embodiment, the rearrangement reaction in step (v) is carried out in the presence of magnesium silicate particles (Florisil®), silica or alumina particles and in the presence of microwave radiation or light.

MODES FOR CARRYING OUT THE INVENTION

Figure 1:
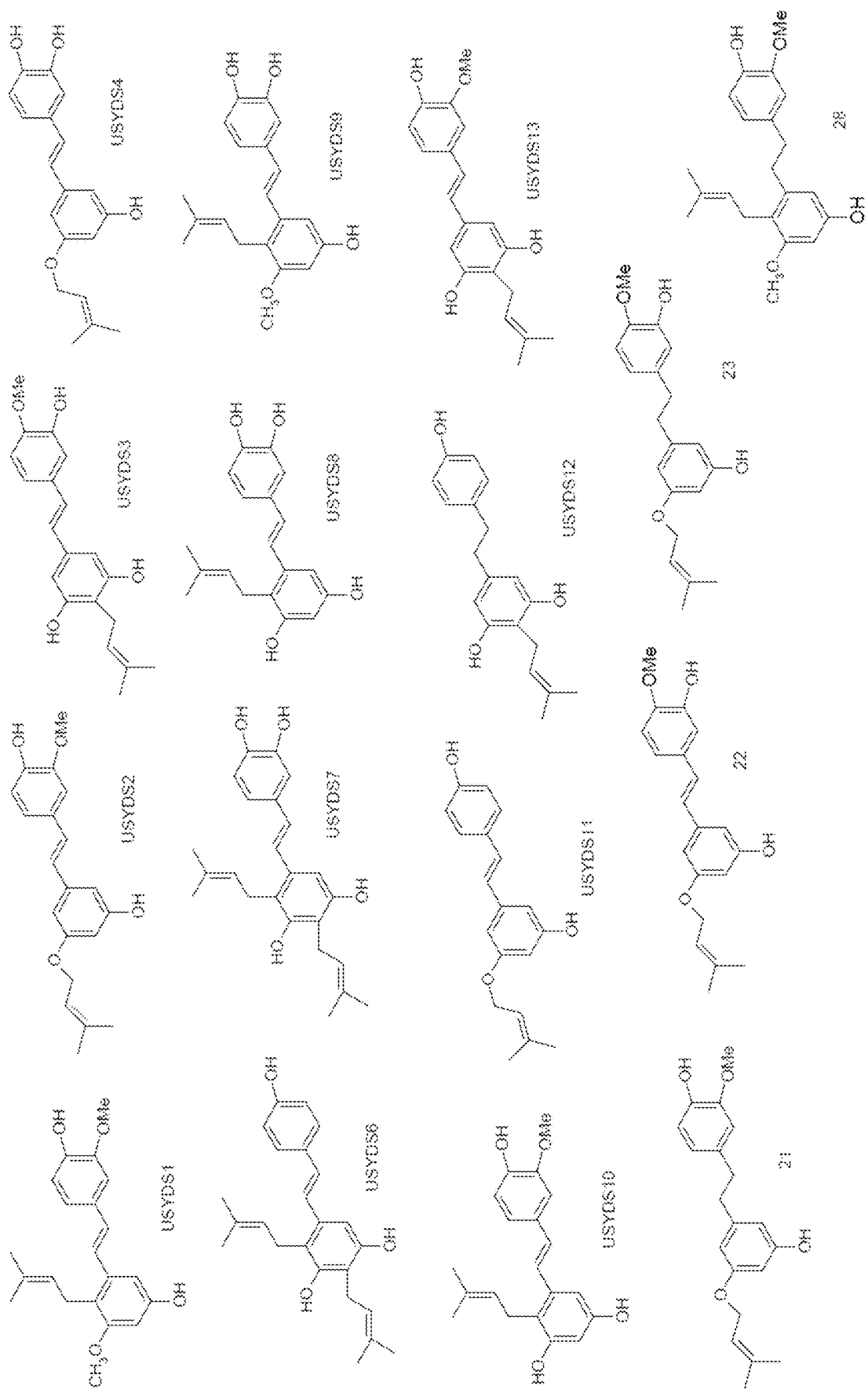
FIG. 1 is a compilation of some of the isolated and synthesised prenylated polyhydroxystilbene derivatives.
Figure 2:
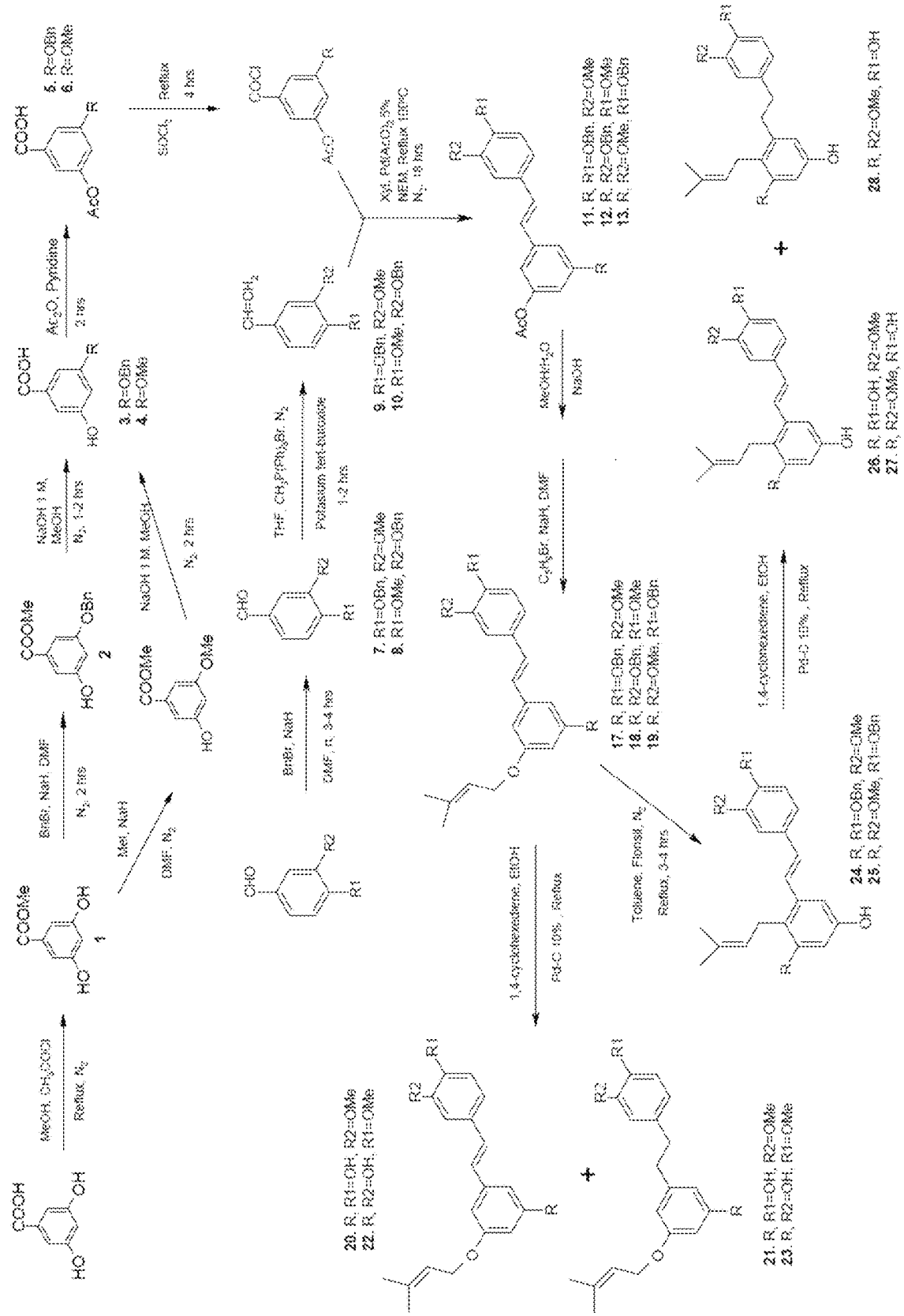
FIG. 2 is a scheme summarising the synthesis of the novel O- and C-prenylated polyhydroxystilbenes derivatives.
Figure 3:
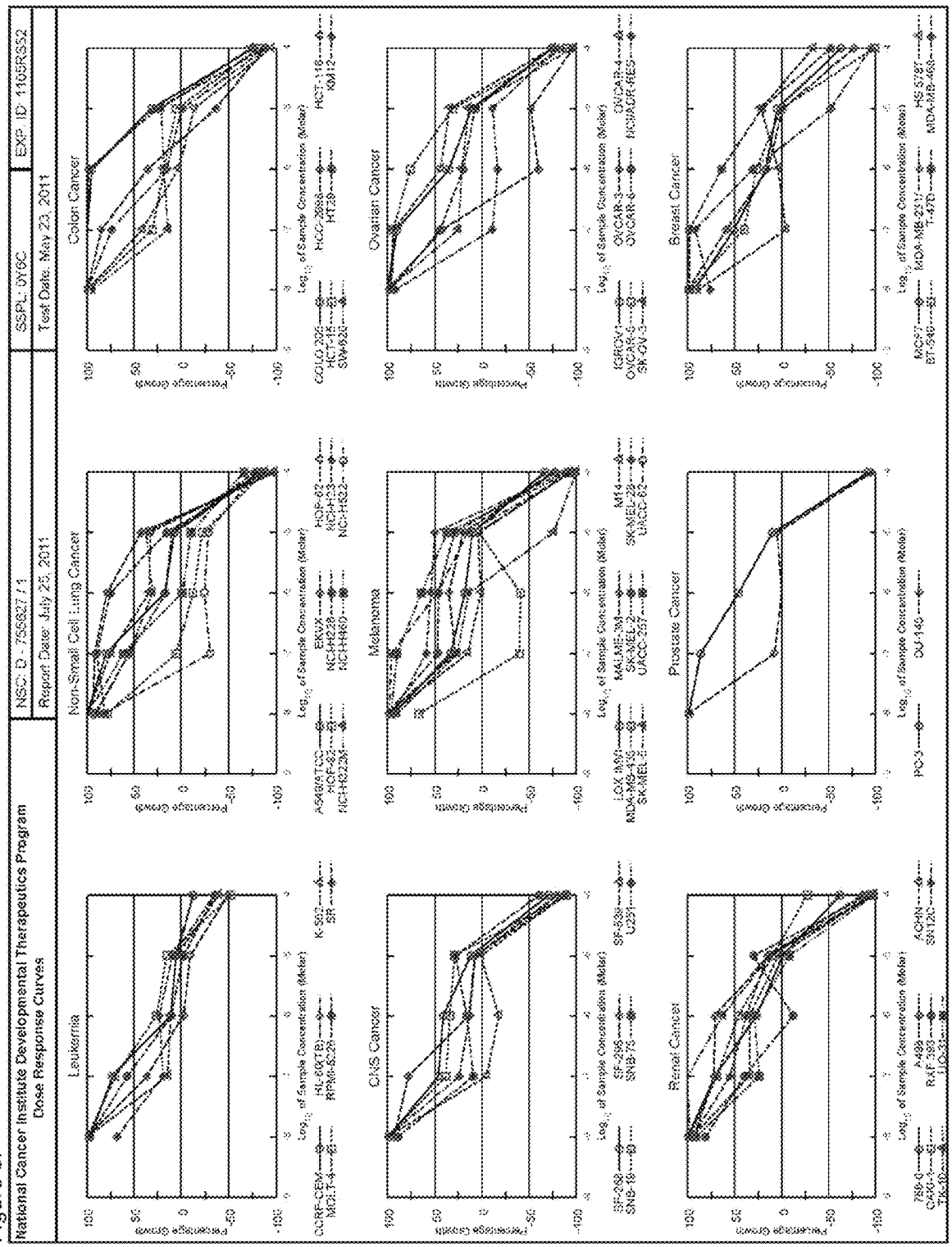
FIG. 3 exhibits dose response curves for the inhibition of human cancerous cell growth, for various cell lines, by compound USYDS1.
Figure 4:
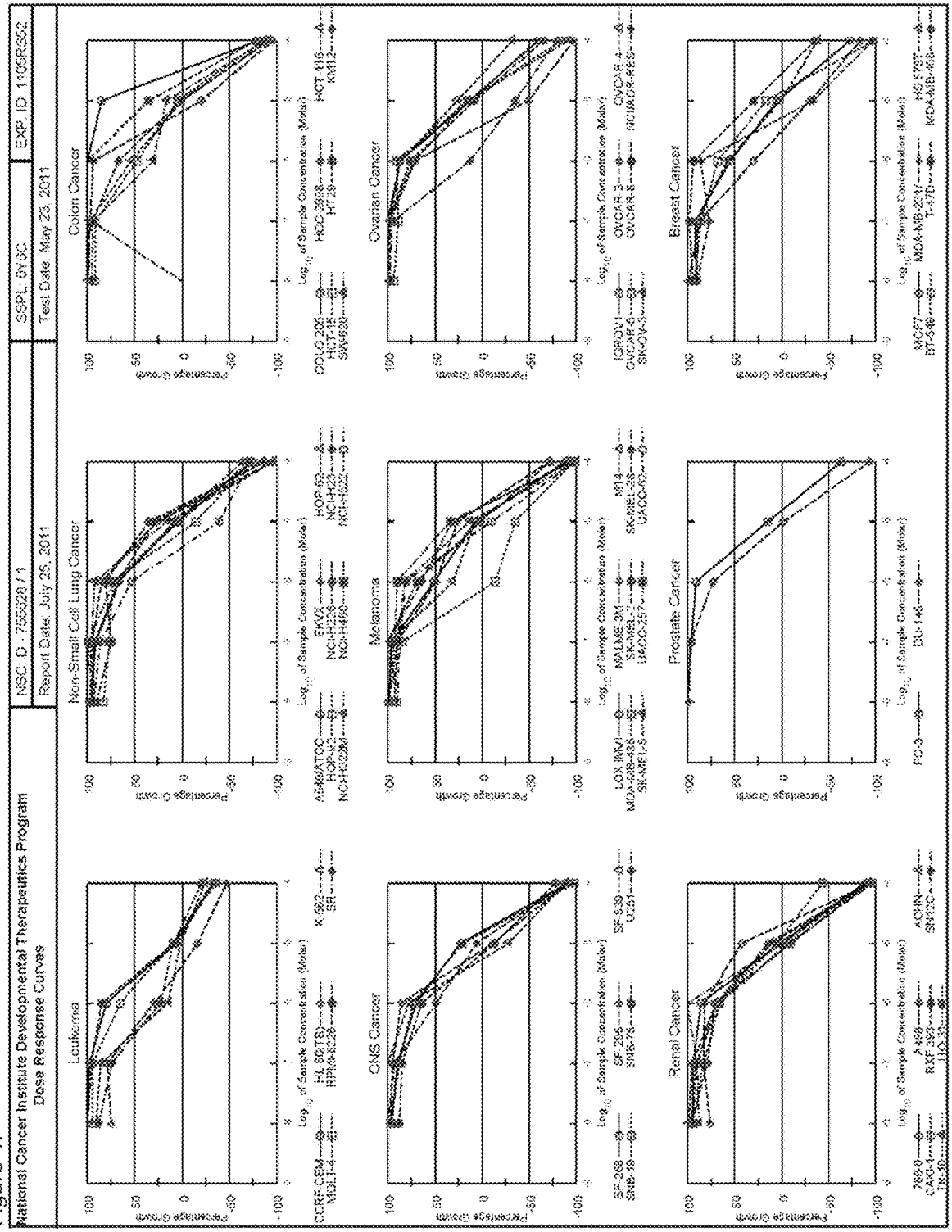
FIG. 4 exhibits dose response curves for the inhibition of human cancerous cell growth, for various cell lines, by compound USYDS2.
Figure 5:
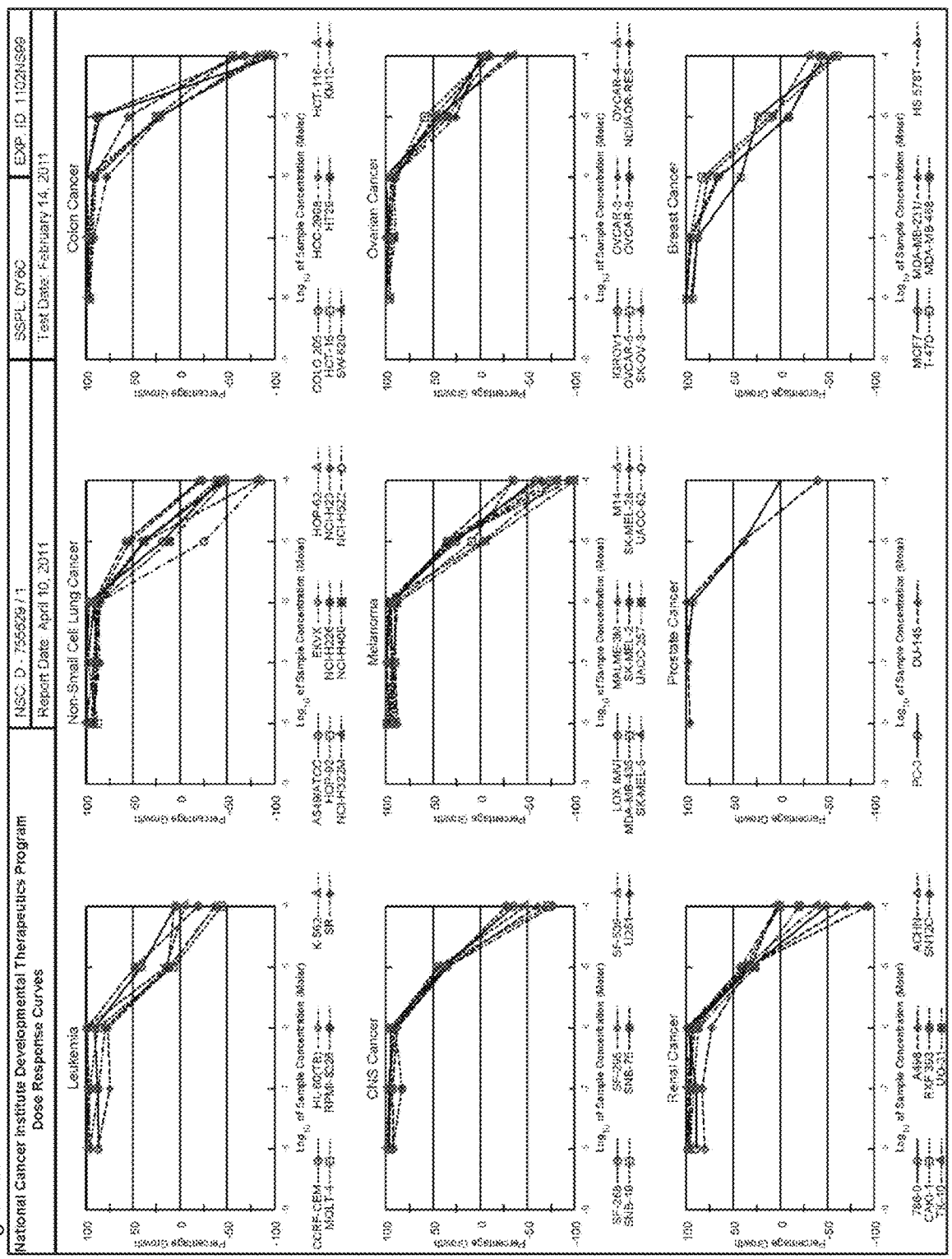
FIG. 5 exhibits dose response curves for the inhibition of human cancerous cell growth, for various cell lines, by compound USYDS13.
Figure 6:
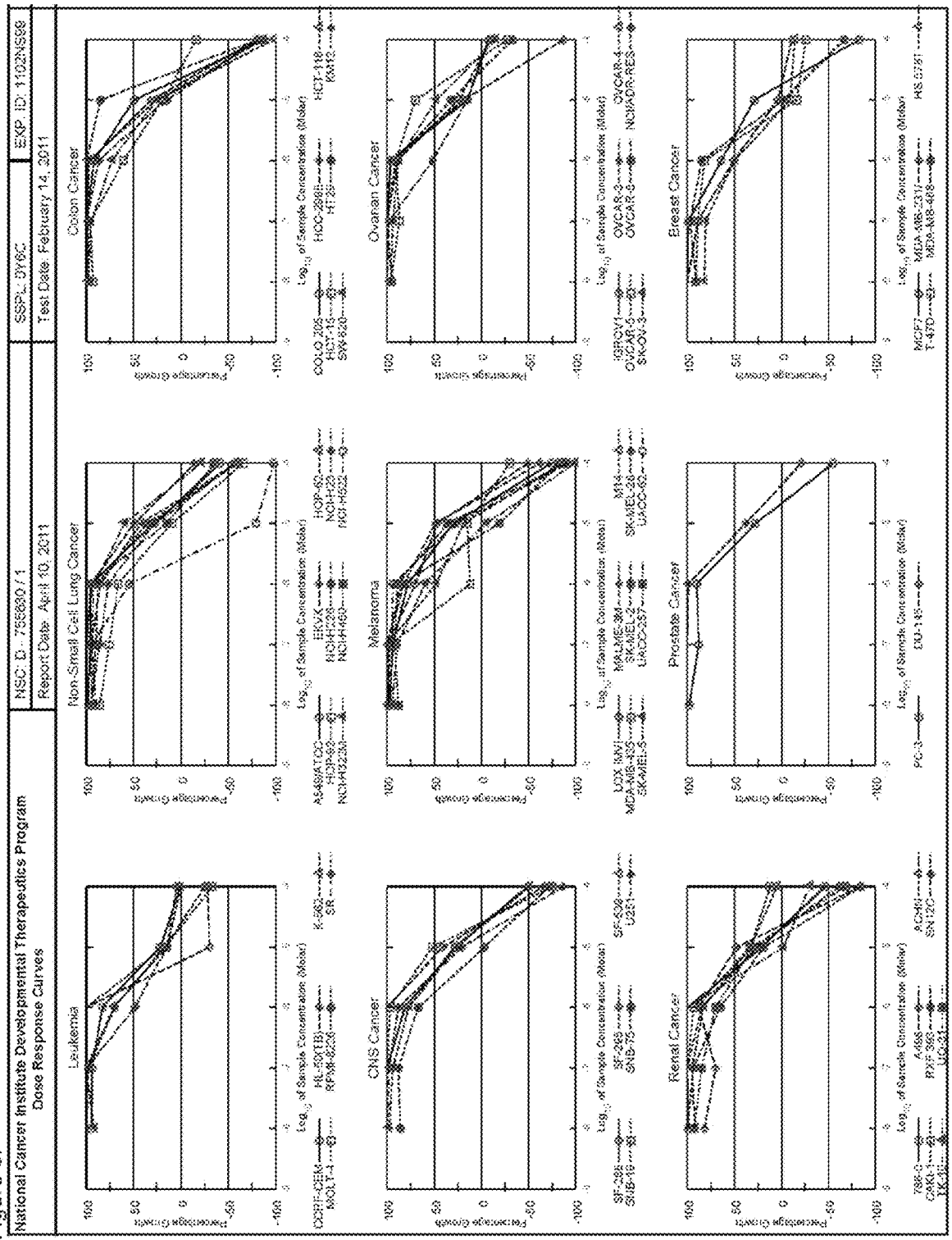
FIG. 6 exhibits dose response curves for the inhibition of human cancerous cell growth, for various cell lines, by compound USYDS4.
Figure 7:
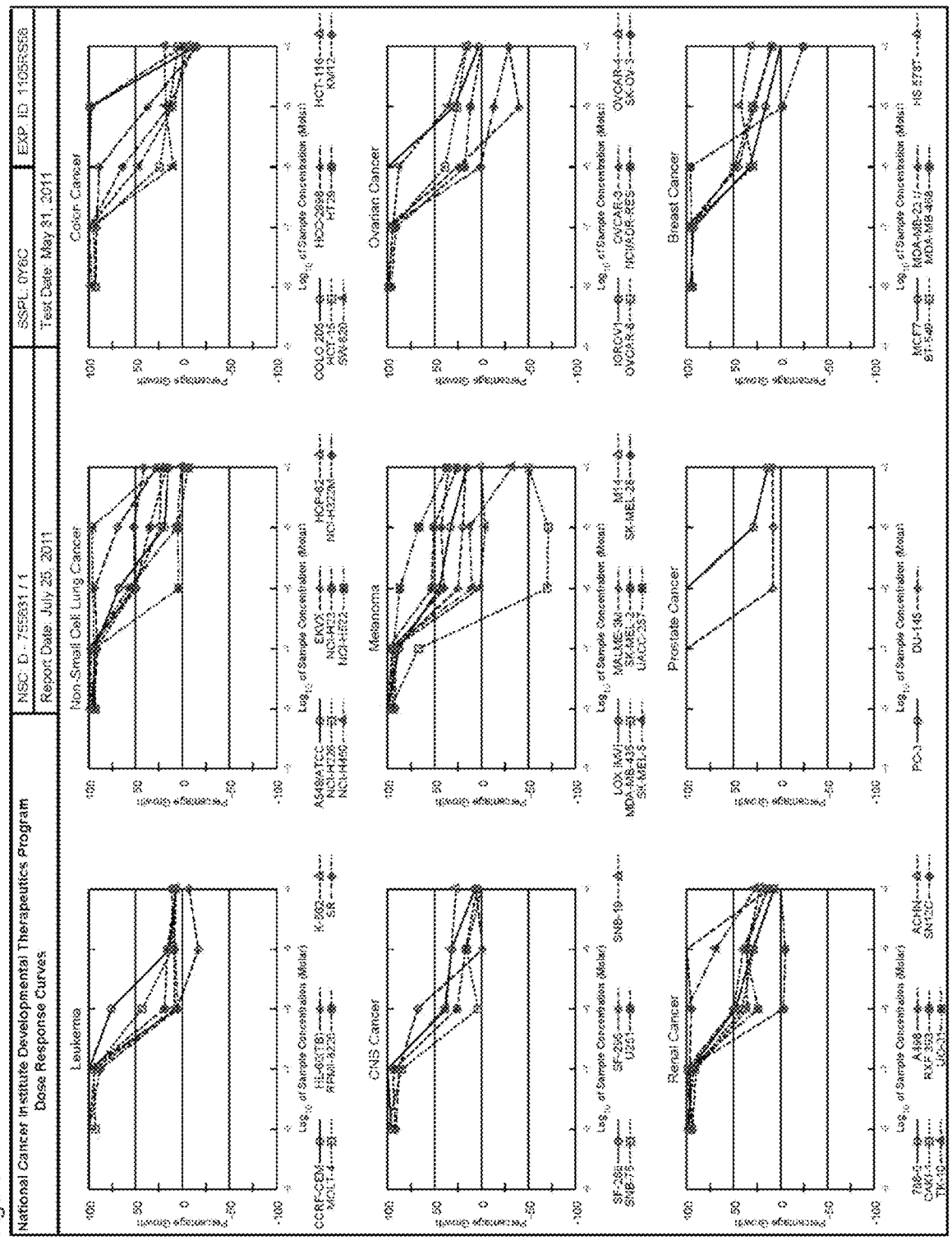
FIG. 7 exhibits dose response curves for the inhibition of human cancerous cell growth, for various cell lines, by compound USYDS9.
Figure 8:
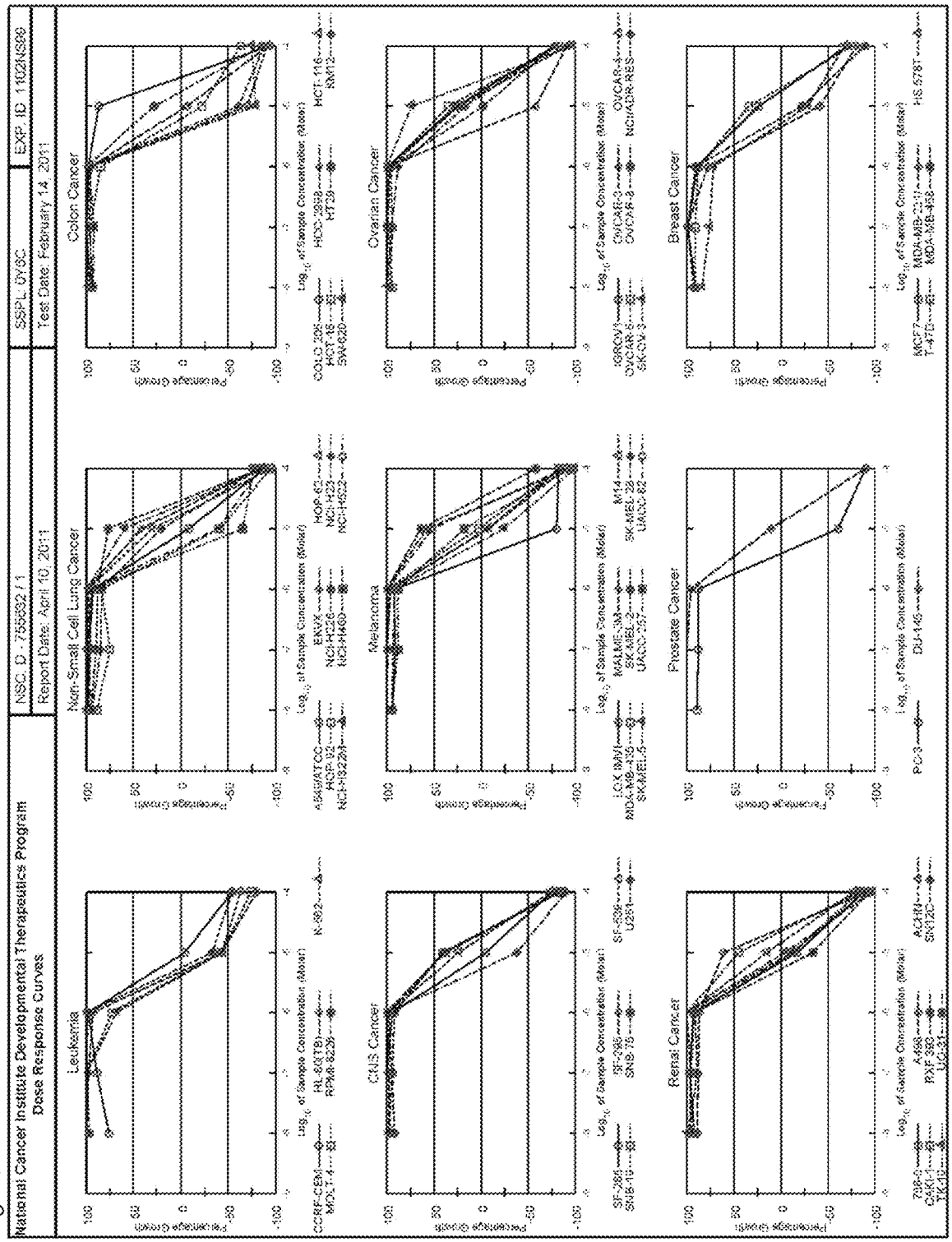
FIG. 8 exhibits dose response curves for the inhibition of human cancerous cell growth, for various cell lines, by compound USYDS6.
Figure 9:
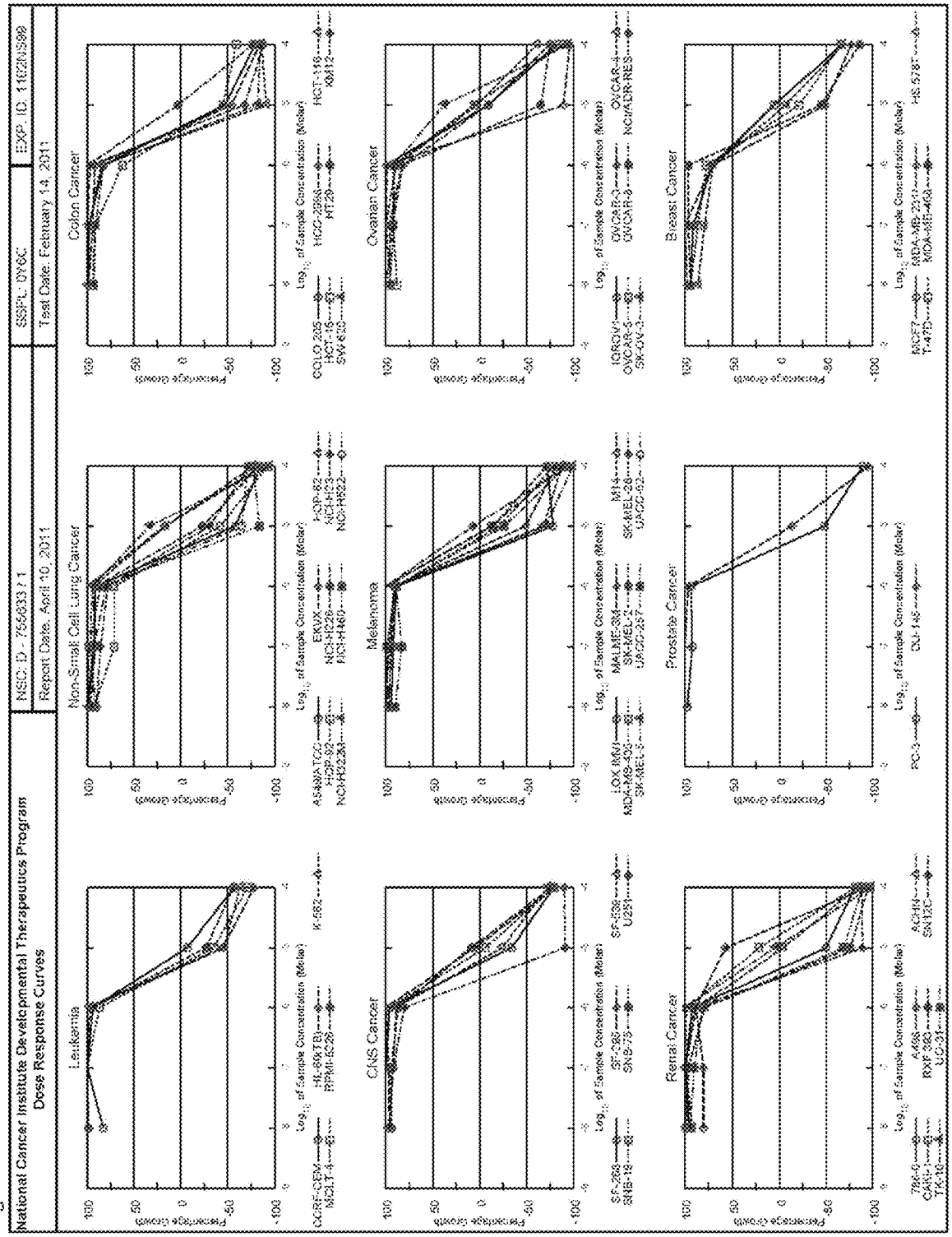
FIG. 9 exhibits dose response curves for the inhibition of human cancerous cell growth, for various cell lines, by compound USYDS7.

In order to better understand the nature of the invention a number of examples will now be described as follows:

Materials

Honey bees observed collecting from the sedges (*Lepidosperma viscidum*) were captured in plastic tubes, capped and frozen. Sections of the bee hind legs holding propolis were cut and pooled. Resin from plants were collected and stored at −20° C. until analysis. Plant samples were obtained and dried at 40° C. in a ventilated oven (Thermoline, NSW Australia) overnight to provide voucher specimens for identification by botanist, A/Prof Murray Henwood, John Ray Museum, University of Sydney, Sydney, Australia, and registered as *Lepidosperma viscidum* chemotype 1a, voucher number Duke 100222-42 and *Lepidosperma viscidum* chemotype 2a, voucher number Duke 100221-21.

76 Beehives made up of 3 10-frame boxes each fitted with a propolis mat under the hive cover lid were used to collect propolis samples. The individually numbered hives were used on location in the apiary sites situated in the central southern region of Kangaroo Island.

Thin layer chromatography sheets precoated with silica gel 60 $F_{254}$ and silica gel 60H for normal-phase short-column chromatography (NPSCC) were purchased from Merck. TLC plates were visualized with a UVGL-58 mineral-light lamp, Multiband UV-2544/366.

All the chemicals used in the isolation and synthesis, including deuterated NMR solvents such as chloroform-d and methanol-$d_4$, deuterated dimethyl sulfoxide ($d_6$-dimethyl sulfoxide) were purchased from Sigma-Aldrich Pty Ltd (Castle Hill, NSW, Australia). Solvents including hexane, dichloromethane, ethyl acetate, isopropanol, ethanol, methanol, and acetic acid were of analytical grade and purchased from Ajax Fine Chem, Taren Point, NSW, Australia. or Asia Pacific Specialty Chemical Ltd (APS).

Rotavapor model R-114 rotary evaporator with a water bath temperature ranging between 40-60° C. was used to evaporate the solvent fraction. Vacuum pump V-700 or Vacuubrand MD 4C NT diaphragm pump (Vacuubrand GMBH, Wertheim, Germany) with vacuum controller V-800 or V-850 is used. Final drying is carried out by a Napco 5831 vacuum oven (NAPCO, Salt Lake City, USA) using a DirectTorr vacuum pump (Sargent-Welch, Buffalo, USA).

Preparative HPLC was performed on a Shimadzu preparative gradient LC-8A system on a reversed-phase column (Grace, Alltima C18 5 µM 22 mm ID×250 mm), injection volume 500 µL, eluted with methanol (75%) and water at 10 mL/min and detected at 280 nm with a UV-Vis detector (Shimadzu SPD-20A). Analytical HPLC was performed on Shimadzu UFLC, LC-20AD pump, SIL-20A HT autosampler, with a Hewlett-Packard Column, NUCLEOSIL 100C18, 5 µm, 4 mm×125 mm, injection volume 20 µL, eluted with methanol-water-acetic acid (70:29.8:0.2) at 1 mL/min and detected at 230 nm with a UV-Vis detector (Shimadzu SPD-20A).

$^1$H and $^{13}$C Nuclear magnetic resonance (NMR) analyses were carried out on Varian 400 MHz System with a SMS autosampler (Palo Alto, Calif., USA). NMR spectra were referenced to tetramethylsilane (TMS). Mass spectra were obtained from a ThermoFinnigan TSQ 7000 (LC-MS/MS system) and a Finnigan Polaris Ion Trap MS/MS system (Finnigan, San Jose, USA) using an Xcalibur 1.2 data system.

Determination of the $^1$H-NMR Chemical Profiles of the Plant and Propolis Specimens Resin samples from the base of stem (0.1 g), bee hind leg (0.01 g) and beehive propolis (1.0 g) were extracted with ethyl acetate at room temperature for 15 min. The extracts were filtered, dried under reduced pressure and analyzed by $^1$H-NMR and HPLC. Samples from the sedge type-1 were found to contain prenylated hydroxystilbenes and cinnamates as major constituents, whereas those from sedge type-2 showed only prenylated stilbenes as major constituents as discussed above. Propolis samples were subsequently selected for isolation of the components.

Isolation and Identification of Prenylated Polyhydroxystilbenes from Propolis of Kangaroo Island.

General Method

Propolis (10 g) was extracted with dichloromethane at room temperature with stirring for 1 hr. The extract was subjected to purification using normal-phase short column chromatography (NPSCC). A step-wise gradient of mobile phase (2×100 mL) consisting of dichloromethane (DCM) and ethyl acetate (EtOAc) at 0, 1, 2, 4, 8, 10, 15, 20, 50 and 100% was employed to elute the components which were analysed by TLC and NMR. Further purification of the compounds, if required, was subsequently carried out on the same NPSCC with different mobile phases consisting of either hexane and EtOAc or hexane and isopropanol. Normal-phase preparative HPLC was also employed when required to further purify the compounds (Shimadzu LC-8A). The compounds were eluted through a silica column (Altima® silica 10 µm, 10 cm×250 cm) at a flow rate of 10 mL/min with a mobile phase of 2% isopropanol in hexane at ambient temperature. The elution of compounds was monitored with a UV detector (UV/Vis SPD-20A) at 280 nm. Structures and identity of these purified compounds were characterized by $^1$H- and $^{13}$C-NMR and mass spectrometry including high resolution mass spectrometry.

Detailed structural analyses of the isolated compound were also carried out when needed by 2D-NMR using Gradient Heteronuclear Multiple Bond Coherence (GHMBC).

Isolated Prenylated Polyhydroxystilbene Derivatives (E)-2-(3-methyl-2-buten-1-yl)-4',5-dihydroxy-3,3'-dimethoxystilbene (USYDS1)

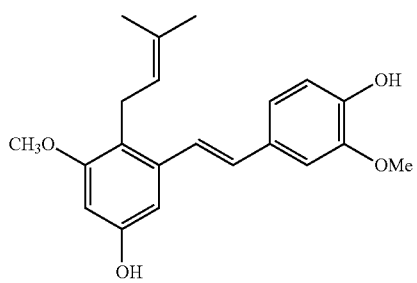

USYDS1

Light yellow liquid. $C_{21}H_{24}O_4$ $^1H$ NMR (methanol-$d_4$, 400 MHz): $R_t$ 14.64 min. δ 7.16 (d, J=16 Hz, H), 7.07 (d, J=4 Hz, H), 6.94 (dd, J=8, 4 Hz, H), 6.86 (d, J=16 Hz, H), 6.78 (d, J=8 Hz, H), 6.63 (d, J=4 Hz, H), 6.34 (d, J=4 Hz, H), 5.06 (m, H), 3.89 (s, 3H), 3.77 (s, 3H), 3.39 (m, 2H), 1.80 (bs, 3H), 1.66 (bs, 3H). $^{13}C$-NMR (CDCl$_3$, 100 MHz) δ 158.5, 154.4, 146.7, 145.6, 138.1, 130.6, 130.4, 130.3, 124.3, 123.7, 120.7, 120.6, 114.5, 108.2, 103.9, 98.2, 55.9, 55.7, 25.8, 24.5, 18.0; CI-MS: m/z 339 (M−1)$^-$, HRESIMS: m/z 341.1749 (M+H)$^+$, calcd 341.1747 for $C_{21}H_{25}O_4$.

(E)-3-(3-methyl-2-butenyloxy)-4',5-dihydroxy-3'-methoxystilbene (USYDS2)

USYDS2

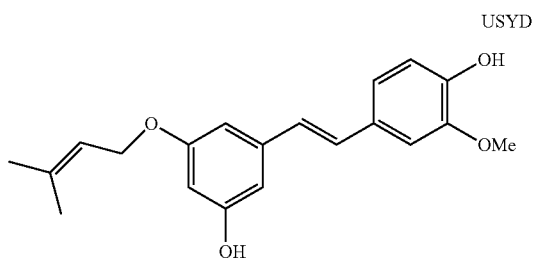

Light yellow liquid. $C_{20}H_{22}O_4$ $^1H$ NMR (methanol-$d_4$, 400 MHz): $R_t$ 15.46 min. δ 7.12 (d, J=4 Hz, 1H), 7.01 (d, J=16 Hz, 1H), 6.97 (dd, J=8, 4 Hz, 1H), 6.88 (d, J=16 Hz, 1H), 6.78 (d, J=8 Hz, 2H, 6.56 (m, 2H), 6.24 (m, 1H), 5.46 (m, 1H), 4.52 (d, J=4 Hz, 2H), 3.90 (s, 3H), 1.79 (bs, 3H), 1.76 (bs, 3H). $^{13}C$-NMR (CDCl$_3$, 100 MHz) δ 160.2, 156.9, 146.7, 145.5, 139.9, 138.6, 129.9, 129.2, 126.2, 120.6, 119.4, 114.7, 108.4, 105.9, 105.4, 101.5, 65.0, 55.9, 25.8, 18.2; CI-MS m/z 325 (M−1)$^-$, HRESIMS m/z 327.15938 (M+H)$^+$, calcd 327.1591 for $C_{20}H_{23}O_4$.

(E)-4-(3-methyl-2-buten-1-yl)-3,4',5-trihydroxy-3'-methoxystilbene (USYDS13)

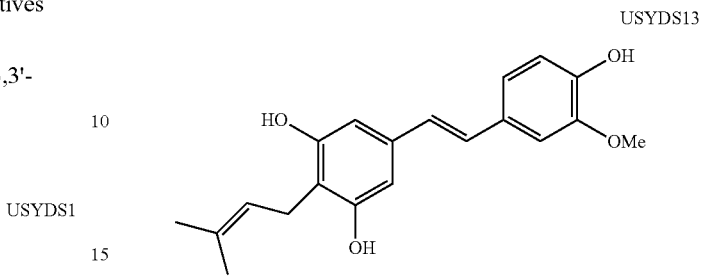

USYDS13

Light yellow liquid. $C_{20}H_{22}O_4$ $^1H$ NMR (methanol-$d_4$, 400 MHz): $R_t$ 11.46 min. δ 7.08 (d, J=4 Hz, 1H), 6.93 (dd, J=8, 4 Hz, 1H), 6.91 (d, J=16 Hz, 1H), 6.78 (d, J=16 Hz, 1H), 6.77 (d, J=8 Hz, 1H), 6.46 (s, 2H), 5.23 (m, 1H), 3.89 (s, 3H), 3.28 (m, 2H), 1.76 (bs, 3H), 1.65 (bs, 3H); $^{13}C$ NMR-GHMBC (methanol-$d_4$, 100 MHz): δ 157.4 (2C, C-3/5, H-2/6, H-1"), 149.3 (1C, C-3', H-2', H-5', OCH$_3$), 147.6 (1C, C-4', H-2', H-6'), 137.7 (1C, C-1', H-beta), 131.4 (1C, C-1, H-alpha), 131.3 (1C, C-3", H-1", H-4", H-5"), 128.7 (1C, C-beta, H-2', H-alpha), 127.6 (1C, C-alpha, H-2/6, H-6'), 124.8 (1C, C-2", H-1", H-4", H-5"), 121.2 (1C, C-6', H-2', H-beta), 116.5 (1C, C-5'), 116.1 (1C, C-4, H-2/6, H-1"), 110.4 (1C, C-2', H-beta), 105.9 (2C, C-2/6, H-2/6, H-alpha), 56.5 (1C, OCH$_3$), 26.1 (1C, C-4", H-5"), 23.5 (1C, C-1"), 18.1 (1C, C-5", H-4"); CI-MS: m/z 325 (M−1)$^-$; HRMS: 325.14453 [M−1]$^-$, (calculated 325.14398 for $C_{20}H_{21}O_4$).

(E)-3-(3-methyl-2-butenyloxy)-3',4',5-trihydroxystilbene (USYDS4)

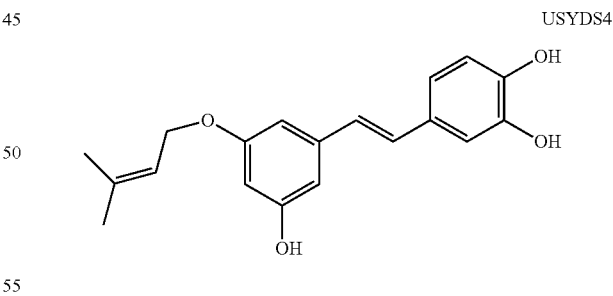

USYDS4

Light yellow liquid. $C_{19}H_{20}O_4$ $^1H$ NMR (methanol-$d_4$, 400 MHz): $R_t$ 18.62 min. δ 6.98 (d, J=4 Hz, 1H), 6.94 (d, J=16 Hz, 1H), 6.85 (dd, J=8, 4 Hz, 1H), 6.80 (d, J=16 Hz, 1H), 6.74 (d, J=8 Hz, 1H), 6.53 (m, 2H), 6.23 (m, 1H), 5.46 (m, 1H), 4.51 (d, J=4 Hz, 2H), 1.79 (bs, 3H), 1.76 (bs, 3H); $^{13}C$ NMR (methanol-$d_4$, 100 MHz): δ 160.2, 158.2, 145.2, 145.1, 139.8, 136.9, 129.5, 128.5, 125.5, 119.9, 118.8, 114.9, 112.4, 105.2, 103.8, 100.7, 64.4, 24.4, 16.8; CI-MS: m/z 311 (M−1)$^-$; HREIMS: m/z 335.1252 (M+Na)$^+$, calcd 335.1259 for $C_{19}H_{20}O_4$Na.

27

(E)-2,4-di(3-methyl-2-buten-1-yl)-3,4',5-trihydroxystilbene (USYDS6)

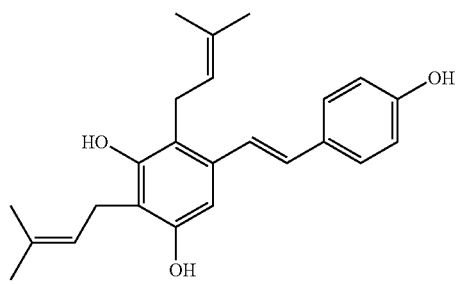

Off-white solid. $C_{24}H_{28}O_3$ $^1$H NMR (methanol-$d_4$, 400 MHz): $R_t$ 9.35 min. δ 7.30 (d, J=8 Hz, 2H), 7.11 (d, J=16 Hz, 1H), 6.80 (d, J=16 Hz, 1H), 6.76 (d, J=8 Hz, 2H), 6.63 (s, 1H), 5.21 (m, 1H), 5.10 (m, 1H), 3.41 (m, 2H), 3.35 (m, 2H), 1.81 (bs, 3H), 1.78 (bs, 3H), 1.68 (bs, 6H); CI-MS: m/z 363 (M−1)$^−$.

(E)-2,4-di(3-methyl-2-buten-1-yl)-3,3',4',5-tetrahydroxystilbene (USYDS7)

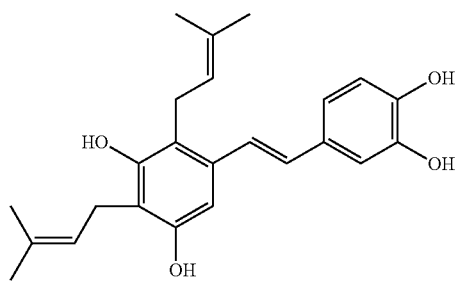

Off-white solid. $C_{24}H_{28}O_4$ $^1$H NMR (methanol-$d_4$, 400 MHz): $R_t$ 10.46 min. δ 7.07 (d, J=16 Hz, 1H), 6.94 (d, J=4 Hz, 1H), 6.79 (dd, J=8.4 Hz, 1H), 6.73 (d, J=16 Hz, 1H), 6.71 (d, J=8 Hz, 1H), 6.62 (s, 1H), 5.21 (m, 1H), 5.10 (m, 1H), 3.41 (m, 2H), 3.35 (m, 2H), 1.81 (bs, 3H), 1.78 (bs, 3H), 1.68 (bs, 6H); $^{13}$C NMR (methanol-$d_4$, 100 MHz): δ 153.23, 152.79, 145.04, 144.84, 134.98, 130.52, 130.26, 129.75, 128.67, 124.08, 123.94, 122.93, 118.56, 118.51, 115.32, 114.93, 112.30, 103.85, 24.54, 24.49, 24.46, 22.32, 16.74, 16.54; CI-MS: m/z 379 (M−1)$^−$; HRMS: 379.19148 [M−1]$^−$, (calculated 379.19092 for $C_{24}H_{27}O_4$).

28

(E)-2-(3-methyl-2-buten-1-yl)-3,3',4',5-tetrahydroxystilbene (USYDS8)

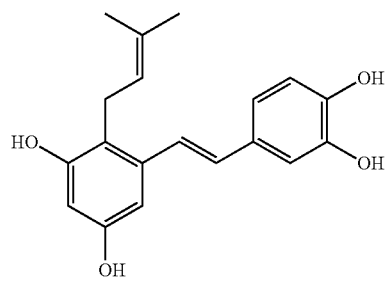

$C_{19}H_{20}O_4$ $^1$H NMR (acetone-$d_6$, 400 MHz): δ 7.07 (d, J=2 Hz, 1H), 7.15 (d, J=16 Hz, 1H), 6.89 (dd, J=8, 2 Hz, 1H), 6.81 (d, J=8 Hz, 1H), 6.80 (d, J=16 Hz, 1H), 6.63 (d, J=2 Hz, 1H), 6.35 (d, J=2 Hz, 1H), 5.15 (t, J=7 Hz, 1H), 3.42 (d, J=7 Hz, 2H), 1.81 (s, 3H), 1.65 (s, 3H). $^{13}$C NMR (acetone-$d_6$, 100 MHz): δ 155.9, 155.8, 145.4, 145.3, 138.4, 130.1, 129.7, 129.4, 124.5, 123.9, 117.4, 119.0, 115.4, 112.9, 103.4, 101.6, 24.0, 25.0, 17.2. HRESIMS: (m/z) 313.1434 (M+H)$^+$, calcd 313.1440 for $C_{19}H_{21}O_4$.

(E)-2-(3-methyl-2-buten-1-yl)-3',4',5-trihydroxy-3-methoxystilbene (USYDS9)

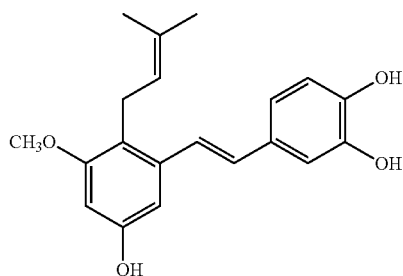

$C_{20}H_{22}O_4$ $^1$H NMR (acetone-$d_6$, 400 MHz): δ 7.16 (d, J=16 Hz, 1H), 7.07 (d, J=2 Hz, 1H), 6.90 (dd, J=8, 2 Hz, 1H), 6.85 (d, J=16 Hz, 1H), 6.82 (d, J=8 Hz, 1H), 6.71 (d, J=2 Hz, 1H), 6.39 (d, J=2.3 Hz, 1H), 5.09 (1H, t, J=7 Hz, 1H), 3.78 (s, 3H), 3.40 (d, J=7 Hz, 2H), 1.80 (s, 3H), 1.64 (s, 3H). $^{13}$C NMR (acetone-$d_6$, 100 MHz): δ 158.5, 156.3, 145.3 (2C), 138.0, 130.1, 130.0, 129.6, 123.7, 124.2, 119.1, 118.9, 115.3, 112.9, 103.7, 98.1, 55.0, 25.0, 23.9, 17.2. HRESIMS: m/z 327.1592 (M+H)$^+$, calcd 327.1596 for $C_{20}H_{23}O_4$.

(E)-2-(3-methyl-2-buten-1-yl)-3,4',5-trihydroxy-3'-methoxystilbene (USYDS10)

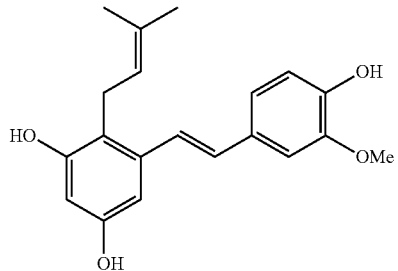

C$_{20}$H$_{22}$O$_4$ $^1$H NMR: (acetone-d$_6$, 400 MHz) δ 7.13 (d, J=16 Hz, 1H) 7.02 (dd, J=8, 2 Hz, 1H), 7.00 (s, 1H), 6.92 (d, J=8 Hz, 1H), 6.85 (d, J=16 Hz, 1H), 6.66 (d, J=2 Hz, 1H), 6.30 (d, J=2 Hz, 1H), 5.20 (t, J=7 Hz, 1H), 3.95 (s, 3H), 3.43 (d, J=7 Hz, 2H), 1.84 (s, 3H), 1.75 (s, 3H). $^{13}$C NMR (acetone-d$_6$, 100 MHz): δ 155.4, 154.4, 146.7, 145.7, 138.8, 133.6, 131.2, 130.1, 124.2, 122.5, 120.5, 117.7, 114.6, 108.4, 105.3, 102.5, 55.9, 25.8, 25.1, 18.0. HRESIMS: m/z 349.1411 (M+Na)$^+$, calcd 349.1416 for C$_{20}$H$_{22}$O$_4$Na.

(E)-3-(3-methyl-2-butenyloxy)-4',5-dihydroxystilbene (USYDS11)

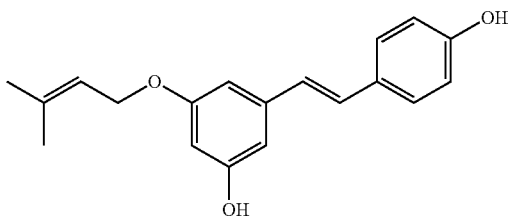

C$_{19}$H$_{22}$O$_3$ $^1$H NMR (CDCl$_3$, 400 MHz): δ 7.38 (dd, J=7, 2 Hz, 2H), 7.00 (d, J=16 Hz, 1H), 6.84 (d, J=16 Hz, 1H), 6.82 (dd, J=7, 2 Hz, 2H), 6.64 (t, J=2 Hz, 1H), 6.56 (t, J=2 Hz, 1H), 6.33 (t, J=2 Hz, 1H), 5.50 (t, J=7 Hz, 1H), 4.51 (d, J=7 Hz, 2H), 1.81 (s, 3H), 1.76 (s, 3H). $^{13}$C NMR (CDCl$_3$, 100 MHz): δ 160.4, 156.7, 155.4, 139.9, 138.4, 130.1, 128.8, 128.0 (2C), 126.3, 119.5, 115.6 (2C), 105.6, 105.5, 101.3, 64.9, 25.8, 18.2.

4-(3-methyl-2-buten-1-yl)-3,4',5-trihydroxydihydrostilbene (USYDS12)

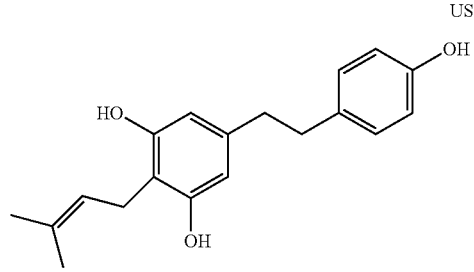

C$_{19}$H$_{22}$O$_4$ $^1$H NMR: (CD$_3$OD, 400 MHz) δ 6.97 (d, J=8 Hz, 2H), 6.66 (d, J=8 Hz, 2H), 6.13 (s, 2H), 5.22 (t, J=7 Hz, 1H), 3.24 (d, J=7 Hz, 2H), 2.72 (m, 2H), 2.64 (m, 2H), 1.74 (s, 3H), 1.64 (s, 3H). $^{13}$C NMR (CD$_3$OD, 100 MHz): δ 155.5 (2C), 154.9, 140.3, 132.9, 129.4, 128.9 (2C), 123.6, 114.6 (2C), 112.3, 106.5 (2C), 38.0, 36.8, 24.5, 21.7, 16.5.

(E)-2-(3-methyl-2-buten-1-yl)-3-(3-methyl-2-butenyloxy)-3',4',5-trihydroxystilbene (USYDS14)

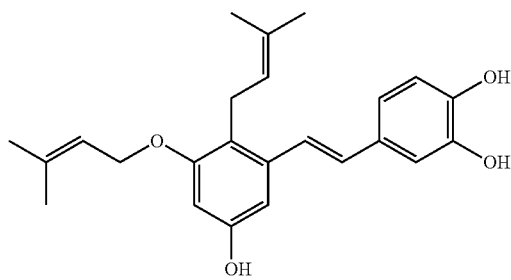

Colourless solid, yield 12 mg. ESI-MS: m/z 379 [M−1]$^−$, $^1$H-NMR (methanol-d$_4$ 400 MHz): δ 7.07 (d, J=16 Hz, 1H), 6.96 (d, J=4 Hz, 1H), 6.80 (dd, J=8, 4 Hz, 1H), 6.79 (d, J=16 Hz, 1H), 6.74 (d, J=8 Hz, 1H), 6.61 (d, J=4 Hz, 1H), 6.32 (d, J=4 Hz, 1H), 5.47 (m, 1H), 5.06 (m, 1H), 4.48 (m, 2H), 3.37 (m, 2H), 1.78 (m, 6H), 1.75 (m, 3H), 1.66 (m, 3H). $^{13}$C-NMR (100 MHz, CD$_3$OD): δ 16.75, 16.80, 23.84, 24.45, 24.54, 64.86, 99.04, 103.41, 112.39, 114.96, 118.71, 119.14, 120.14, 123.54, 123.97, 129.51, 129.70, 130.01, 136.78, 137.95, 145.08, 145.09, 155.59, 157.47. HRMS: 379.19148 [M−1]$^−$, (calculated 379.19092 for C$_{24}$H$_{27}$O$_4$).

(E)-2,6-di(3-methyl-2-buten-1-yl)-3,3',5,5'-tetrahydroxystilbene USYDS15

Colourless solid, yield 9 mg. ESI-MS: m/z 379 [M−1]$^−$, $^1$H NMR (methanol-d$_4$, 400 MHz): δ 6.91 (br t, 1H), 6.82 (d, J=16 Hz, 1H), 6.73 (d, J=1 Hz, 2H), 6.28 (s, 1H), 6.27 (d, J=16 Hz, 1H), 5.12 (m, 2H), 3.26 (d, J=6 Hz 4H), 1.65 (m, 6H), 1.59 (m, 6H). $^{13}$C-NMR (100 MHz, CD$_3$OD): δ 16.75, 24.53, 25.60, 112.27, 114.86, 117.66, 118.24, 124.06, 124.63, 130.20, 133.33, 139.41, 144.73, 144.97, 153.04. HRMS: 379.19149 [M−1]$^−$, (calculated 379.19092 for C$_{24}$H$_{27}$O$_4$).

(E)-2,6-di(3-methyl-2-buten-1-yl)-3,4',5-trihydroxy-3'-methoxystilbene USYDS18

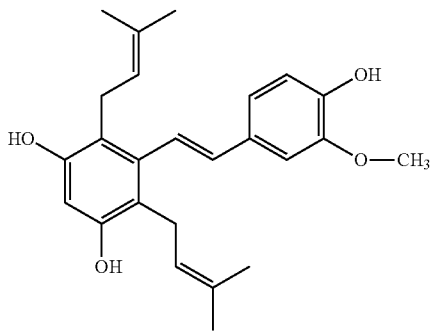

USYDS18

Yield 5 mg. ESI-MS: m/z 393 [M−1]⁻. $^1$H NMR: (CD$_3$OD, 400 MHz) δ 7.03 (d, J=2 Hz, 1H), 6.87 (d, J=17 Hz, 1H), 6.85 (dd, J=8, 2 Hz, 1H), 6.77 (d, J=8 Hz, 1H), 6.33 (d, J=17 Hz, 1H), 6.30 (s, 1H), 5.14 (br t, J=6 Hz, 2H), 3.88 (s, 3H), 3.26 (br d, J=6 Hz, 4H), 1.66 (br s, 6H), 1.60 (br s, 6H). $^{13}$C NMR (CD$_3$OD, 100 MHz): δ 18.37 (2C), 26.12 (2C), 27.20 (2C), 56.53, 102.58, 110.27, 116.42, 119.23 (2C), 121.03, 126.02 (2C), 126.31, 130.41 (2C), 131.7, 134.87, 140.95, 147.51, 149.26, 154.65 (2C). HRMS: 417.20363 [M+23]⁺, (calculated 417.20418 for C$_{25}$H$_{30}$O$_4$Na).

Chemical Modification and Synthesis of Prenylated Polyhydroxystilbenes

A. Rearrangement of O-prenyl to C-prenyl Polyhydroxystilbene

A mixture of USYDS2 (5 mg) and Florisil (5 mg) in xylene (2 ml) was heated at 120° C. for 30 min in a microwave reactor (CEM Discover Microwave). The product was dried under reduced pressure and purified using NPSCC. Two rearrangement products were observed in a combined yield of approximately 30%.

The major product observed was (E)-4-(3-methyl-2-buten-1-yl)-3,4',5-trihydroxy-3'-methoxystilbene (USDYS13):

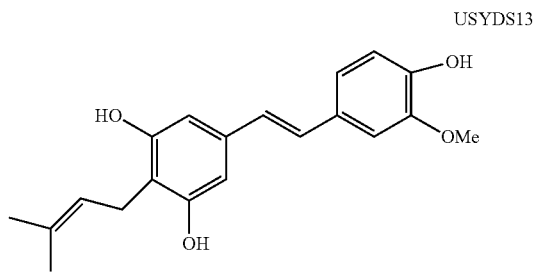 [SMILES: COc1cc(/C=C/c2cc(O)c(CC=C(C)C)c(O)c2)ccc1O]

USYDS13

The minor product observed was (E)-2-(3-methyl-2-buten-1-yl)-3,4',5-trihydroxy-3'-methoxystilbene (USYDS10).

B. Synthesis of Prenylated Polyhydroxystilbenes

1. Preparation of 3,5-dihydroxybenzoic acid methyl ester (1)

To a solution of 3,5-dihydroxybenzoic acid (10 g, 64.9 mmol) in anhydrous methanol (150 mL) acetyl chloride (2 mL, 28.1 mmol) was added dropwise. The mixture was heated at reflux under N$_2$ for 17 hours. The solvent was evaporated and the residue was dissolved in ethyl acetate (100 mL), then washed with saturated sodium hydrogen carbonate (3×100 mL). The combined organic layers were washed with water (2×100 mL), dried over sodium sulfate, filtered and concentrated in vacuo to afford 2 as a colourless solid (9.80 g, 90%): mp 167-168° C. (lit.[1] mp 168-169° C.); $^1$H NMR (400 MHz, Acetone-d$_6$) δ 8.66 (s, 2H), 7.00 (d, J=2.4 Hz, 2H), 6.59 (t, J=2.4 Hz, 2H), 3.83 (s, 3H).

2. Preparation of 3-hydroxy-5-benzyloxybenzoic acid methyl ester (2)

To a suspension of NaH (60% dispersion in mineral oil, 3.3 g, 137.3 mmol) in anhydrous N,N-dimethylformamide (DMF) (100 mL) was added a solution of 2 (10 g, 59.5 mmol) in anhydrous DMF (30 mL) at 0° C. under N$_2$, followed by the dropwise addition of benzyl bromide (6.4 mL, 53.8 mmol). The reaction mixture was stirred at room temperature for 2 hours, quenched with cold water (50 mL), acidified with cold 1 M HCl (20 mL) and extracted with diethyl ether (3×50 mL). The combined organic extracts were washed with water (2×50 mL), dried over sodium sulfate, filtered and evaporated in vacuo. The product was purified using NPSCC using a step-wise gradient consisting of chloroform/ethanol to afford 2 as an off-white solid (4.5 g, 60%)[2]: mp 97-98° C. (lit.[3] mp 98° C.); C$_{15}$H$_{14}$O$_4$ $^1$H NMR (400 MHz, CDCl$_3$) δ 8.01 (s, 1H), 7.43-7.33 (m, 5H), 7.24 (dd, J=2.0, 1.2 Hz, 1H), 7.20 (dd, J=2.0, 1.2 Hz, 1H), 6.70 (t, J=2.0 Hz, 1H), 5.07 (s, 2H), 3.90 (s, 3H).

3. Preparation of 3-hydroxy-5-benzyloxybenzoic acid (3)

To a solution of 2 (4.5 g, 16.7 mmol) in methanol (30 mL) was added 1 M NaOH (60 mL, 60 mmol). The resulting reaction mixture was stirred at 45° C. for 4 hours under N$_2$, followed by the addition of 1 M HCl (50 mL) to acidify the solution before extraction with ethyl acetate (3×40 mL). The combined organic extracts were washed with water (2×30 mL) and dried over sodium sulfate. The solvent was evaporated in vacuo to afford 3 as an off-white solid (4.02 g, 94%): mp 196-198° C.; C$_{14}$H$_{12}$O$_4$ $^1$H NMR (400 MHz, Acetone-d$_6$) δ 7.42-7.33 (m, 5H), 7.21 (dd, J=2.4, 1.2 Hz, 1H), 7.11 (dd, J=2.4, 1.2 Hz, 1H), 6.68 (t, J=2.4 Hz, 1H), 5.07 (s, 2H).

4. Preparation of 3-hydroxy-5-methoxybenzoic acid (4)

The title compound was prepared as described above by using methyl iodide instead of benzyl bromide to afford 4 as an off-white solid, mp 199-200° C. (lit.[4] mp 199-200° C.); C$_8$H$_8$O$_4$ $^1$H NMR (400 MHz, Acetone-d$_6$) δ 8.01 (s, 2H), 7.16 (t, J=1.2 Hz, 1H), 7.13 (t, J=1.2 Hz, 1H), 6.15 (t, J=2.4 Hz, 1H), 3.82 (s, 3H).

5. Preparation of 3-acetoxy-5-benzyloxybenzoic acid (5)

To the solution of 3 (4.02 g, 17.6 mmol) in acetic anhydride (20 mL, 21.6 mmol) was added pyridine (10%, 0.15 mL, 1.76 mmol). The mixture was stirred at room temperature for 4 hours, quenched with water (30 mL), acidified by 0.1 M HCl (10 mL) and extracted with ethyl acetate (3×40 mL). The combined organic extracts were washed with water (2×30 mL), dried over sodium sulfate and filtered. The solvent was evaporated in vacuo and recrystallised from a mixture (1:1) of hexane/ethyl acetate to afford 5 as pinkish crystals (3.86 g, 96%)[5]: mp 133-134° C.; $C_{16}H_{14}O_5$ $^1H$ NMR (400 MHz, $CDCl_3$) δ 7.59 (dd, J=2.4, 1.2 Hz, 1H), 7.45 (dd, J=2.4, 1.2 Hz, 1H), 7.43-7.34 (m, 5H), 6.99 (t, J=2.4 Hz, 1H), 5.1 (s, 2H), 2.32 (s, 3H).

6. Preparation of 3-acetoxy-5-methoxybenzoic acid (6)

The title compound was prepared as described in 5 was used to give 6 as an off white solid: mp 151-153° C.; $C_{10}H_{10}O_5$ $^1H$ NMR (400 MHz, $CDCl_3$) δ 7.50 (dd, J=2.0, 1.4 Hz, 1H), 7.43 (dd, J=2.0, 1.4 Hz, 1H), 6.90 (t, J=2.0 Hz, 1H), 3.86 (s, 3H), 2.32 (s, 3H).

7. Preparation of 3-methoxy-4-benzyloxybenzaldehyde (7)

To a suspension of NaH (60% dispersion in mineral oil, 1.6 g, 66.6 mmol) in anhydrous DMF (50 mL) at 0° C. under $N_2$ was added vanillin (4-hydroxy-3-methoxy benzaldehyde, 4 g, 26.3 mmol) in anhydrous DMF (20 mL) slowly via syringe, followed by the dropwise addition of benzyl bromide (3 mL, 25.2 mmol). The mixture was stirred at room temperature for 4 hours, quenched with cold water (30 mL), acidified with cold 1 M HCl (15 mL) and extracted with diethyl ether (3×40 mL). The combined organic extracts were washed with water (2×30 mL), dried over sodium sulfate and dried under reduced pressure to afford 7 as a colourless solid (6 g, 92%): mp 60-62° C. (lit.[6] mp 61-62° C.); $C_{15}H_{14}O_3$ $^1H$ NMR (400 MHz, $CDCl_3$) δ 9.84 (s, 1H)), 7.43-7.31 (m, 7H)), 7.00 (d, J=8.4 Hz, 1H)), 5.25 (s, 2H)), 3.95 (s, 3H)).

8. Preparation of 4-methoxy-3-benzyloxybenzaldehyde (8)

The title compound was prepared as described in 7 to give 8 as a colourless solid: mp 61-63° C. (lit.[7] mp 61-63° C.); $C_{15}H_{14}O_3$ $^1H$ NMR (400 MHz, $CDCl_3$) δ 9.80 (s, 1H)), 7.49-7.31 (m, 7H)), 7.00 (d, J=8.1 Hz, 1H)), 5.20 (s, 2H)), 3.97 (s, 3H)).

9. Preparation of 4-ethenyl-2-methoxy-1-benzyloxybenzene (9)

To a suspension of methyltriphenylphosphonium bromide (6.5 g, 18.2 mmol) in anhydrous tetrahydrofuran (THF) (15 mL) under $N_2$ at 0° C. was added potassium tert-butoxide (2.3 g, 20.5 mmol) and the reaction mixture was warmed to room temperature. A solution of benzyl vanillin (7) (4 g, 16.5 mmol) in anhydrous THF (15 mL) was added dropwise and stirred for 2 hours, then quenched with cold water (20 mL), acidified with 0.1 M HCl (20 mL), and extracted with ethyl acetate (3×40 mL). The combined organic extracts were washed with 20% aq. sodium chloride (20 mL) then dried under reduced pressure. The product was purified using NPSCC using a step-wise mobile phase consisting of hexane/ethyl acetate to afford 9 as a colourless solid (3.37 g, 85%); mp 53-54° C. (lit.[8] mp 50-51° C.); $C_{16}H_{16}O_2$ $^1H$ NMR (400 MHz, $CDCl_3$) δ 7.45-7.28 (m, 5H), 6.99 (d, J=2 Hz, 1H), 6.90 (dd, J=4, 1 Hz, 1H), 6.83 (d, J=4 Hz, 1H), 6.68 (dd, J=17, 1 Hz, 1H), 5.64 (dd, J=17, 1 Hz, 1H), 5.17 (s, 2H), 5.14 (d, J=1 Hz, 1H), 3.92 (s, 3H).

10. Preparation of 5-ethenyl-2-methoxy-1-benzyloxybenzene (10)

The title compound was prepared as described in 9 to give 10 as an off-white solid; mp 68-69° C. (lit.[9] mp 68-69° C.); $C_{16}H_{16}O_2$ $^1H$ NMR (400 MHz, $CDCl_3$): δ 7.48-7.31 (m, 5H), 7.01 (d, J=2 Hz, 1H), 6.97 (dd, J=8, 2 Hz, 1H), 6.85 (d, J=8 Hz, 1H), 6.64 (dd, J=17, 1 Hz, 1H), 5.56 (dd, J=17, 1 Hz, 1H), 5.17 (s, 2H), 5.12 (d, J=1 Hz, 1H), 3.92 (s, 3H).

11. Preparation of E-1-[3-acetoxy-5-benzyloxyphenyl]-2-[3-methoxy-4-benzyloxyphenyl]ethene (11)

To a solution of N,N-bis(2,6-diisopropyl) dihydro imidazolium chloride (0.093 g, 10%, 0.217 mmol) and $Pd(OAc)_2$ (0.048 g, 10%, 0.217 mmol) in xylene (3 mL) under $N_2$ at room temperature was added the acid chloride of 5 (0.7 g, 2.17 mmol) in xylene 2 mL, followed by the addition of 4-ethylmorpholine (0.04 mL, 0.316 mmol) and reagent 9 (0.627 g, 2.61 mmol) in xylene (3 mL). The mixture was heated at 130° C. for 18-22 hours. The solvent was evaporated in vacuo and the product was purified using NPSCC (hexane/ethyl acetate 3:1 as mobile phase) to give 11 as an yellow oil (0.33 g, 31.6%); $C_{31}H_{28}O_5$ $^1H$ NMR (400 MHz, $CDCl_3$) δ 7.45-7.28 (m, 13H), 7.06 (d, J=2.0 Hz, 1H), 7.02 (d, J=17 Hz, 1H), 6.97 (dd, J=6, 2 Hz, 1H), 6.89 (m, 1H), 6.62 (t, J=2 Hz, 1H), 5.18 (s, 2H), 5.07 (s, 2H), 3.94 (s, 3H), 2.30 (s, 3H); $^{13}C$ NMR (100 MHz, $CDCl_3$) δ 169.39, 159.78, 151.81, 149.79, 148.32, 139.82, 137.00, 136.57, 130.48, 129.78, 128.63 (2C), 128.58 (2C), 128.10, 127.88, 127.55 (2C), 127.24 (2C), 126.02, 119.98, 113.95, 112.02, 110.50, 109.48, 107.28, 71.0, 70.27, 56.02, 21.19; CI-MS m/z (%): 481 (M+1)$^+$, 503 (M+Na)$^+$; HRMS: m/z 503.1828 (M+Na)$^+$, calcd 503.1834 for $C_{31}H_{28}O_5Na$.

12. Preparation of E-1-[3-acetoxy-5-benzyloxyphenyl]-2-[3-benzyloxy-4-methoxyphenyl]ethene (12)

The title compound was prepared as described in 11 to condense the acid chloride of 5 with reagent 10. The product was recrystallised from a mixture (2:1) of hexane/toluene to afford yellowish needle crystals; $C_{31}H_{28}O_5$ mp 133-134° C.; $^1H$ NMR (400 MHz, $CDCl_3$) δ 7.49-7.29 (m, 10H), 7.07 (d, J=2 Hz, 1H), 7.05 (dd, J=8, 2 Hz, 1H), 6.97 (d, J=16 Hz, 1H), 6.95 (t, J=2 Hz, 1H), 6.89 (d, J=8 Hz, 1H), 6.84 (t, J=2 Hz, 1H), 6.82 (d, J=16 Hz, 1H), 6.62 (t, J=2 Hz, 1H), 5.18 (s, 2H), 5.07 (s, 2H), 3.94 (s, 3H), 2.30 (s, 3H); $^{13}C$ NMR (100 MHz, $CDCl_3$) δ 169.39, 159.76, 151.80, 149.90, 148.34, 139.83, 137.05, 136.58, 129.94, 129.78, 128.64 (2C), 128.60 (2C), 128.11, 127.94, 127.58 (2C), 127.38 (2C), 125.88, 120.59, 112.00, 111.91, 111.81, 110.52, 107.22, 71.16, 70.27, 56.06, 21.18 ($CH_3CO$); CI-MS m/z 481 (M+1)$^+$, 503 (M+Na)$^+$; HRMS m/z 503.1832 (M+Na)$^+$, calcd 503.1834 for $C_{31}H_{28}O_5Na$.

13. Preparation of E-1-[3-acetoxy-5-methoxyphenyl]-2-[3-methoxy-4-benzyloxyphenyl]ethene (13)

The title compound was prepared as described in 11 to condense the acid chloride of 6 with reagent 9 to give the title compound as an off white solid; mp 104-106° C.; $C_{25}H_{24}O_5$ $^1H$ NMR (400 MHz, $CDCl_3$) δ 7.45-7.30 (m, 8H), 7.07 (d, J=2 Hz, 1H), 7.03 (d, J=16 Hz, 1H), 6.98 (dd, J=8, 2 Hz, 1H), 6.90 (d, J=16 Hz, 1H), 6.88 (m, 1H), 5.18 (s, 2H), 3.95 (s, 3H), 3.83 (s, 3H), 2.31 (s, 3H); $^{13}$C NMR (100 MHz, CDCl$_3$) δ 169.41, 160.58, 151.83, 149.78, 148.31, 139.76, 137.00, 130.49, 129.72, 128.58 (2C), 127.88, 127.24 (2C), 126.07, 119.97, 113.94, 111.73, 109.67, 109.46, 106.54, 71.01, 56.02, 55.50, 21.18; CI-MS m/z 405 [M+1]$^+$; HRMS m/z 405.1695 (M+H)$^+$, calcd 405.1702 for C$_{25}$H$_{25}$O$_5$.

14. Preparation of E-1-[3-hydroxy-5-benzyloxyphenyl]-2-[3-methoxy-4-benzyloxyphenyl]ethene (14)

To a solution of stilbene 11 (0.04 g, 0.083 mmol) in mixed solvent (MeOH/THF/H$_2$O, 3/3/3 mL) was added NaOH (0.02 g, 0.35 mmol) at 0° C. under N$_2$. The reaction mixture was warmed up to room temperature and stirred for 3 hours. The solution was acidified with 0.1 M HCl (5 mL) and extracted with ethyl acetate (3×20 mL). The combined organic extracts were washed with 20% aq. sodium chloride (10 mL), dried over sodium sulphate and evaporated in vacuo. The product was purified using NPSCC (mobile phase of hexane/ethyl acetate) followed by recrystallisation to afford 14 as a colourless solid (0.016 g, 44.5%); mp 114-115° C.; C$_{29}$H$_{26}$O$_4$ $^1$H NMR (400 MHz, Methanol-d$_4$) δ 7.45-7.28 (m, 10H), 7.06 (d, J=2 Hz, 1H), 7.00 (d, J=16 Hz, 1H), 6.98 (dd, J=8, 2 Hz, 1H), 6.87 (d, J=8 Hz, 1H), 6.86 (d, J=16 Hz, 1H), 6.71 (t, J=2.0 Hz, 1H), 6.59 (t, J=2 Hz, 1H), 6.38 (t, J=2 Hz, 1H), 5.18 (s, 2H), 5.07 (s, 2H), 3.95 (s, 3H); $^{13}$C NMR (100 MHz, Methanol-d$_4$) δ 160.29, 156.78, 149.76, 148.19, 139.92, 136.98, 136.84, 130.65, 129.20, 128.61 (2C), 128.57 (2C), 128.02, 127.88, 127.49 (2C), 127.26 (2C), 126.54, 119.94, 113.96, 109.45, 105.97, 105.69, 101.54, 71.02, 70.01, 56.03; CI-MS: 461 (M+Na)$^+$, 439 (M+1)$^+$; HRMS m/z 439.1908 (M+H)$^+$, calcd 439.1909 for C$_{29}$H$_{27}$O$_4$.

15. Preparation of E-1-[3-hydroxy-5-benzyloxyphenyl]-2-[3-benzyloxy-4-methoxyphenyl]ethene (15)

Basic hydrolysis of 12 was carried out as described for compound 14 to give the title compound as a colourless solid; mp 117-119° C.; C$_{29}$H$_{26}$O$_4$ $^1$H NMR (400 MHz, Methanol-d$_4$) δ 7.49-7.30 (m, 10H), 7.07 (d, J=2.0 Hz, 1H), 7.06 (dd, J=8.4, 2.0 Hz, 1H), 6.96 (d, J=16.0 Hz, 1H), 6.87 (d, J=8.0 Hz, 1H), 6.79 (d, J=16.4 Hz, 1H), 6.99 (t, J=1.6 Hz, 1H), 6.57 (t, J=2.0 Hz, 1H), 6.38 (t, J=2.4 Hz, 1H), 5.19 (s, 2H), 5.07 (s, 2H), 3.90 (s, 3H). $^{13}$C NMR (100 MHz, Methanol-d$_4$) δ 160.20, 158.30, 149.68, 148.25, 139.70, 137.41, 137.31, 130.62, 128.16, 128.07 (2C), 128.05 (2C), 127.52, 127.41 (3C), 127.15 (2C), 126.62, 120.35, 111.95 (2C), 105.67, 104.09, 101.11, 70.88, 69.56, 55.10; CI-MS: m/z 461 (M+Na)$^+$, 439 (M+1)$^+$; HRMS m/z 439.1907 (M+H)$^+$, calcd 439.1909 for C$_{29}$H$_{27}$O$_4$.

16. Preparation of E-1-[3-hydroxy-5-methoxyphenyl]-2-[3-methoxy-4-benzyloxyphenyl]ethene (16)

Basic hydrolysis of 13 was carried out as described for compound 14 to give the title compound as a yellowish solid; mp 110-112° C.; C$_{23}$H$_{22}$O$_4$ $^1$H NMR (400 MHz, CDCl$_3$) δ 7.45-7.28 (m, 5H), 7.07 (d, J=2 Hz, 1H), 7.00 (d, J=16 Hz, 1H), 6.98 (dd, J=8, 2 Hz, 1H), 6.87 (d, J=17 Hz, 1H), 6.85 (d, J=8 Hz, 1H), 6.62 (t, J=2 Hz, 1H), 6.57 (t, J=2 Hz, 1H), 6.31 (t, J=2 Hz, 1H), 5.17 (s, 2H), 3.94 (s, 3H), 3.81 (s, 3H); $^{13}$C NMR (100 MHz, CDCl$_3$) δ 161.08, 156.86, 149.73, 148.16, 139.85, 136.96, 130.69, 129.11, 128.57 (2C), 127.90, 127.29 (2C), 126.61, 119.95, 113.97, 109.47, 105.72, 104.73, 100.72, 71.03, 56.03, 55.36; CI-MS, m/z 384 (M+Na)$^+$, 363 (M+1)$^+$; HRMS m/z 363.1592 (M+H)$^+$, calcd 363.1596 for C$_{23}$H$_{23}$O$_4$.

17. Preparation of E-1-[3-(3-methyl-2-butenyloxy)-5-benzyloxyphenyl]-2-[3-methoxy-4-benzyloxyphenyl]ethene (17)

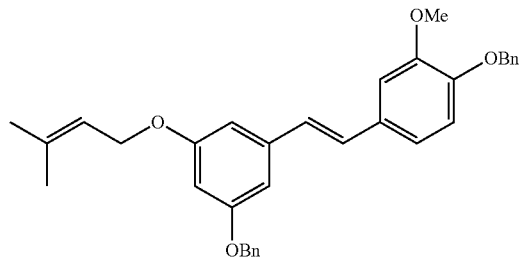

To the suspension of NaH (60% dispersion in mineral oil, 0.0051 g, 0.213 mmol) in anhydrous DMF (5 mL) under N$_2$ at 0° C., stilbene 14 (0.04 g, 0.091 mmol) was added dropwise in DMF (3 mL), followed by the dropwise addition of 3,3-dimetylallyl bromide (0.011 mL, 0.091 mmol).[2] The mixture was stirred at room temperature for 2-3 hours, then quenched with cold water (5 mL), acidified with cooled 0.1 M HCl (5 mL) and extracted with diethyl ether (3×10 mL). The combined organic extracts were washed with water (2×10 mL) and dried under reduced pressure. The product was purified using NPSCC (hexane/ethyl acetate as mobile phase) to give 17 as a yellowish oil (0.02 g, 43.3%); C$_{34}$H$_{34}$O$_4$ $^1$H NMR (400 MHz, CDCl$_3$) δ 7.46-7.28 (m, 10H), 7.07 (d, J=2 Hz, 1H), 7.01 (d, J=16 Hz, 1H), 6.96 (d, J=2 Hz, 1H), 6.90 (d, J=16 Hz, 1H), 6.87 (d, J=8 Hz, 1H), 6.73 (t, J=2 Hz, 1H), 6.68 (t, J=2 Hz, 1H), 6.48 (t, J=2 Hz, 1H), 5.52 (m, 1H), 5.17 (s, 2H), 5.07 (s, 2H), 4.52 (d, J=7 Hz, 2H), 3.95 (s, 3H), 1.80 (d, J=1 Hz, 3H), 1.76 (d, J=1 Hz, 3H); $^{13}$C NMR (100 MHz, CDCl$_3$) δ 160.21, 160.12, 149.78, 148.14, 139.49, 138.35, 137.03, 136.94, 130.76, 128.94, 128.59 (2C), 128.56 (2C), 127.94, 127.86, 127.54 (2C), 127.24 (2C), 126.97, 119.87, 119.53, 113.98, 109.43, 105.38, 105.32, 101.14, 71.01, 70.09, 64.84, 56.03, 25.85, 18.22; CI-MS: m/z 529 (M+Na)$^+$, 507 (M+1)$^+$; HRMS m/z 507.2528 (M+H)$^+$, calcd 507.2535 for C$_{34}$H$_{35}$O$_4$.

18. Preparation of E-1-[3-(3-methyl-2-butenyloxy)-5-benzyloxyphenyl]-2-[3-benzyloxy-4-methoxyphenyl]ethene (18)

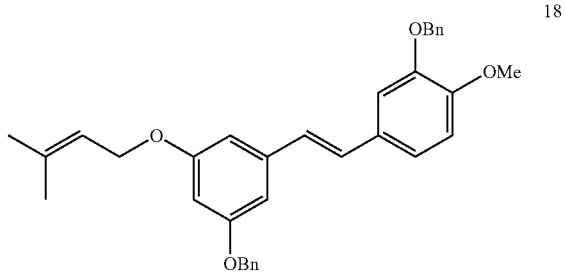 [SMILES: COc1ccc(/C=C/c2cc(OCC=C(C)C)cc(OCc3ccccc3)c2)cc1OCc1ccccc1]

Prenylation of 15 was carried out as described for compound 17 to give the title compound as an off white solid; mp 88-90° C.; $C_{34}H_{34}O_4$ $^1H$ NMR (400 MHz, CDCl$_3$) δ 7.49-7.32 (m, 10H), 7.08 (d, J=2 Hz, 1H), 7.06 (dd, J=8, 2 Hz, 1H), 6.97 (d, J=16 Hz, 1H), 6.89 (d, J=8 Hz, 1H), 6.82 (d, J=16 Hz, 1H), 6.71 (t, J=2 Hz, 1H), 6.66 (t, J=2 Hz, 1H), 6.47 (t, J=2 Hz, 1H), 5.53 (m, 1H), 5.20 (s, 2H), 5.07 (s, 2H), 4.52 (d, J=6 Hz, 2H), 3.91 (s, 3H), 1.80 (d, J=1 Hz, 3H), 1.75 (d, J=1 Hz, 3H); $^{13}C$ NMR (100 MHz, CDCl$_3$) δ 161.04, 160.95, 150.51, 149.11, 140.24, 139.03, 137.81, 137.67, 130.91, 129.57, 129.27 (4C), 128.66, 128.58, 128.22 (2C), 128.05 (2C), 127.50, 121.10, 120.20, 112.48, 112.40, 105.95, 105.86, 101.60, 71.55, 70.47, 65.18, 56.36, 26.00, 18.33; CI-MS: m/z 529 (M+Na)$^+$, 507 (M+1)$^+$; HRMS m/z 507.2530 (M+H)$^+$, calcd 507.2535 for $C_{34}H_{35}O_4$.

19. Preparation of E-1-[3-(3-methyl-2-butenyloxy)-5-methoxyphenyl]-2-[3-methoxy-4-benzyloxyphenyl]ethene (19)

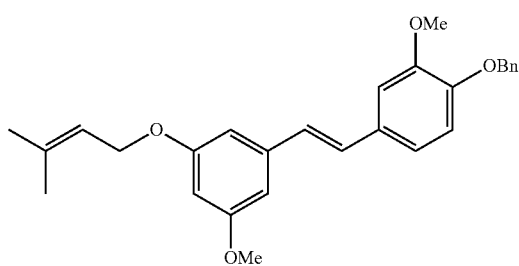

Prenylation of 16 was carried out as described for compound 17 to give the title compound as off white crystal; mp 66-69° C.; $C_{28}H_{30}O_4$ $^1H$ NMR (400 MHz, CDCl$_3$) δ 7.45-7.28 (m, 5H), 7.08 (d, J=2 Hz, 1H), 7.02 (d, J=16 Hz, 1H), 6.98 (d, J=2 Hz, 1H), 6.90 (d, J=16 Hz, 1H), 6.87 (d, J=8 Hz, 1H), 6.67 (t, J=2 Hz, 1H), 6.64 (t, J=2 Hz, 1H), 6.40 (t, J=2 Hz, 1H), 5.53 (m, 1H), 5.17 (s, 2H), 4.53 (d, J=7 Hz, 2H), 3.96 (s, 3H), 3.81 (s, 3H), 1.81 (d, J=1 Hz, 3H), 1.76 (d, J=1 Hz, 3H); $^{13}C$ NMR (100 MHz, CDCl$_3$) δ 160.91, 160.23, 149.76, 148.14, 139.46, 138.35, 137.04, 130.78, 128.90, 128.56 (2C), 127.87, 127.25 (2C), 127.02, 119.86, 119.56, 113.98, 109.44, 104.96, 104.49, 100.37, 71.02, 64.82, 56.04, 55.36, 25.86, 18.22; CI-MS: m/z 453 (M+Na)$^+$; HRMS m/z 453.2036 (M+Na)$^+$, calcd 453.2042 for $C_{28}H_{30}O_4Na$.

20. Preparation of (E)-3-(3-methyl-2-butenyloxy)-4',5-dihydroxy-3'-methoxystilbene (20, Equivalent to USYDS2)

To a solution of 17 (0.02 g, 0.035 mmol) in absolute ethanol (8 mL), was added 1,4-cyclohexadiene (3 mL, 0.030 mmol) and Pd—C(10%, 0.002 g). The mixture was stirred under N$_2$ and refluxed at 80° C. for 4 hours. The solution was filtered and dried under reduced pressure to give an oil residue which was purified by high performance liquid chromatography (HPLC) to afford 20 as a yellowish oil; $C_{20}H_{22}O_4$ $^1H$ NMR (400 MHz, CDCl$_3$) δ 7.02 (d, J=2 Hz, 1H), 7.00 (d, J=16 Hz, 1H), 6.99 (d, J=2 Hz, 1H), 6.91 (dd, J=8, 1 Hz, 1H), 6.85 (d, J=16 Hz, 1H), 6.64 (t, J=2 Hz, 1H), 6.56 (t, J=2 Hz, 1H), 6.33 (t, J=2 Hz, 1H), 5.53 (m, 1H), 4.52 (d, J=7 Hz, 2H), 3.95 (s, 3H), 1.82 (d, J=1 Hz, 3H), 1.76 (d, J=1 Hz, 3H); $^{13}C$ NMR (100 MHz, CDCl$_3$) δ 160.38, 156.70, 146.67, 145.69, 139.87, 138.37, 129.73, 129.29, 126.15, 120.63, 119.49, 114.54, 108.24, 105.58, 105.38, 101.29, 64.85, 55.92, 25.85, 18.22; CI-MS: m/z 325 (M−1)$^-$; HRMS m/z 327.1588 (M+H)$^+$, calcd 327.1596 for $C_{20}H_{23}O_4$.

21. Preparation of 3-(3-methyl-2-butenyloxy)-4',5-dihydroxy-3'-methoxydihydro-stilbene (21)

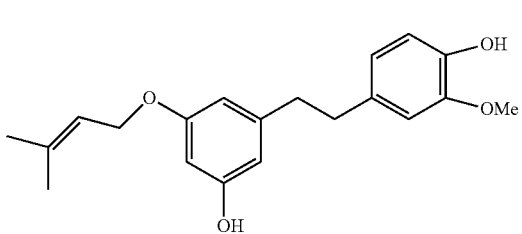

The title compound was obtained by hydrogenation of the double bond on the bridging C=C during removal of the benzyl group of compound 20. The title compound was obtained as a light yellow oil; $C_{20}H_{24}O_4$ $^1H$ NMR (400 MHz, CDCl$_3$) δ 6.84 (d, J=8 Hz, 1H), 6.69 (dd, J=8, 2 Hz, 1H), 6.62 (d, J=2 Hz, 1H), 6.34 (t, J=2 Hz, 1H), 6.26 (t, J=2.0 Hz, 1H), 6.24 (t, J=2 Hz, 1H),), 5.46 (m, 1H), 5.46 (s, 1H), 4.68 (s, 1H), 4.53 (d, J=7 Hz, 2H), 3.84 (s, 3H), 2.85 (m, 4H), 1.80 (d, J=0.4 Hz, 3H), 1.73 (d, J=0.5 Hz, 3H); $^{13}C$ NMR (100 MHz, CDCl$_3$) δ 160.11, 156.44, 146.22, 144.46, 143.73, 138.23, 133.61, 120.95, 119.55, 114.15, 111.10, 107.89, 107.58, 99.62, 64.72, 55.84, 38.29, 37.23, 25.84, 18.18; CI-MS: m/z 351 (M+Na)$^+$; HRMS m/z 351.1566 (M+Na)$^+$, calcd 351.1572 for $C_{20}H_{24}O_4Na$.

22. Preparation of (E)-3-(3-methyl-2-butenyloxy)-3',5-dihydroxy-4'-methoxystilbene (22)

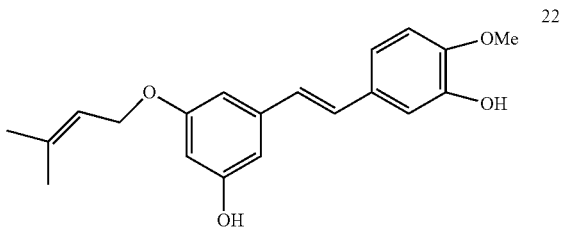 [SMILES: COc1ccc(/C=C/c2cc(O)cc(OCC=C(C)C)c2)cc1O]

Removal of benzyl group of 18 was carried out as described for compound 20 to give the title compound as a light yellow oil; $C_{20}H_{22}O_4$ $^1H$ NMR (400 MHz, CDCl$_3$) δ 7.13 (d, J=2 Hz, 1H), 6.98 (d, J=16 Hz, 1H), 6.97 (dd, J=8, 2 Hz, 1H), 6.86 (d, J=8 Hz, 1H), 6.86 (d, J=16 Hz, 1H), 6.64 (t, J=2 Hz, 1H), 6.57 (t, J=2 Hz, 1H), 6.33 (t, J=2 Hz, 1H), 5.60 (s, 1H), 5.52 (m, 1H), 4.77 (s, 1H), 4.52 (d, J=9 Hz, 2H), 3.91 (s, 3H), 1.82 (d, J=1 Hz, 3H), 1.76 (d, J=1 Hz, 3H); $^{13}C$ NMR (100 MHz, CDCl$_3$) δ 160.37, 156.69, 146.51, 145.75, 139.83, 138.36, 130.87, 128.92, 126.78, 119.51, 119.40, 111.84, 110.62, 105.66, 105.48, 101.33, 65.18, 56.36, 26.00, 18.33; CI-MS: m/z 349.1408 (M+Na)$^+$, calcd 349.1416 for $C_{20}H_{22}O_4Na$.

23. Preparation of 3-(3-methyl-2-butenyloxy)-3',5-dihydroxy-4'-methoxydihydro-stilbene (23)

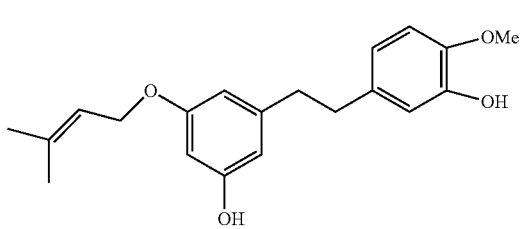

The title compound was obtained by hydrogenation of double bond on the side chain during removal of the benzyl groups of compound 18. The title compound was obtained as a light yellow oil; $C_{20}H_{24}O_4$ $^1$H NMR (400 MHz, CDCl$_3$) δ 6.79 (d, J=2 Hz, 1H), 6.77 (d, J=4 Hz, 1H), 6.66 (dd, J=8, 2 Hz, 1H), 6.35 (t, J=2 Hz, 1H), 6.27 (m, 1H), 5.56 (s, 1H), 5.50 (m, 1H), 4.74 (s, 1H), 4.46 (d, J=7 Hz, 2H), 3.88 (s, 3H), 2.80 (m, 4H), 1.80 (d, J=1 Hz, 3H), 1.74 (d, J=1 Hz, 3H); $^{13}$C NMR (100 MHz, CDCl$_3$) δ 160.11, 156.42, 145.41, 144.80, 144.51, 138.18, 135.07, 119.73, 119.59, 114.59, 110.55, 107.81, 107.49, 99.64, 64.73, 55.00, 38.05, 36.89, 25.83, 18.18; CI-MS: m/z 351 (M+Na)$^+$; HRMS m/z 351.1566 (M+Na)$^+$, calcd 351.1572 for $C_{20}H_{24}O_4$Na.

24. Preparation of E-1-[2-(3-methyl-2-butenyl)-5-hydroxy-3-benzyloxyphenyl]-2-[3-methoxy-4-benzyloxyphenyl]ethene (24)

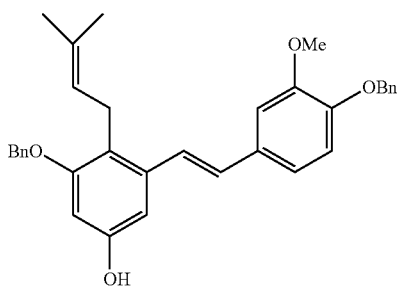

To a solution of 17 (0.024 g, 0.061 mmol) in toluene (30 mL) was added 100-200 mesh Florisil (0.24 g, 10×) and heated at 110° C. under N$_2$, for 4 hours. The reaction mixture was filtered, evaporated in vacuo and the red-brown residue was purified using NPSCC (hexane/ethyl acetate as mobile phase) to afford a brownish solid (0.014 g, 58.3%). The product was recrystallised from hexane/ethyl acetate (3:1) mixture to give 24 as an off white solid; mp 145-150° C.; $C_{34}H_{34}O_4$ $^1$H NMR (400 MHz, CDCl$_3$) δ 7.46-7.28 (m, 10H), 7.20 (d, J=16 Hz, 1H), 7.06 (d, J=2 Hz, 1H), 6.97 (dd, J=8, 2 Hz, 1H), 6.88 (d, J=16 Hz, 1H), 6.87 (d, J=8 Hz, 1H), 6.68 (d, J=2 Hz, 1H), 6.40 (d, J=2 Hz, 1H), 5.18 (s, 2H), 5.17 (m, 1H), 5.05 (s, 2H), 4.69 (s, 1H), 3.94 (s, 3H), 3.48 (d, J=7 Hz, 2H), 1.73 (d, J=1 Hz, 3H), 1.67 (d, J=1 Hz, 3H); $^{13}$C NMR (100 MHz, CDCl$_3$) δ 157.60, 154.27, 149.76, 148.08, 138.31, 137.14, 137.04, 131.18, 130.59, 130.35, 128.56 (2C), 128.49 (2C), 127.86, 127.78, 127.23 (2C), 127.21 (2C), 124.74, 123.63, 121.13, 119.85, 113.99, 109.47, 104.31, 99.53, 71.03, 70.29, 55.98, 25.77, 24.69, 18.01.

25. Preparation of E-1-[2-(3-methyl-2-butenyl)-5-hydroxy-3-methoxyphenyl]-2-[3-methoxy-4-benzyloxyphenyl]ethene (25)

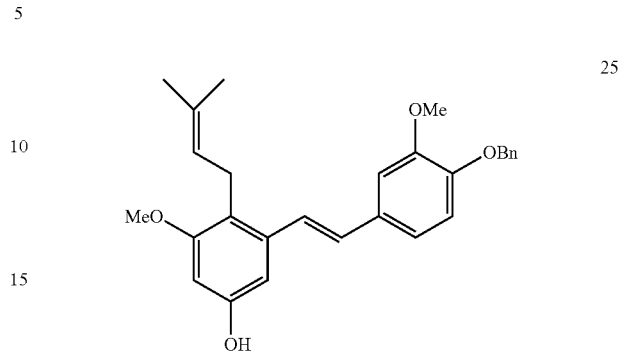

Rearrangement of 19 was carried out as described for compound 24 to give a pinkish solid: mp 161-162° C.; $C_{28}H_{30}O_4$ $^1$H NMR (400 MHz, CDCl$_3$) δ 7.46-7.28 (m, 5H), 7.19 (d, J=16 Hz, 1H), 7.06 (d, J=2 Hz, 1H), 6.97 (dd, J=8, 2 Hz, 1H), 6.88 (d, J=16 Hz, 1H), 6.87 (d, J=8 Hz, 1H), 6.66 (t, J=2 Hz, 1H), 6.40 (t, J=2 Hz, 1H), 5.18 (s, 2H), 5.13 (m, 1H), 4.64 (s, 1H), 3.94 (s, 3H), 3.80 (s, 3H), 3.42 (d, J=6 Hz, 2H), 1.80 (d, J=1 Hz, 3H), 1.68 (d, J=1 Hz, 3H); $^{13}$C NMR (100 MHz, CDCl$_3$) δ 158.56, 154.35, 149.76, 148.07, 138.11, 137.04, 131.21, 130.63, 130.24, 128.56 (2C), 127.86, 127.22 (2C), 124.73, 123.61, 120.78, 119.84, 113.99, 109.42, 103.88, 98.21, 71.03, 55.97, 55.68, 25.77, 24.46, 17.98; CI-MS: m/z 453 (M+Na)$^+$, 431 (M+1)$^+$; HRMS m/z 431.2217 (M+1)$^+$, calcd 431.2222 for $C_{28}H_{31}O_4$.

26. Preparation of (E)-2-(3-methyl-2-buten-1-yl)-3,4',5-trihydroxy-3'-methoxystilbene (26, Equivalent to USYDS10)

To a solution of 24 (0.02 g, 0.035 mmol) in absolute ethanol (6 mL) was added 1,4-cyclohexadiene (3 mL) and Pd—C (10%, 0.0035 mmol). The mixture was stirred under N$_2$ and heated at 80° C. for 4 hours. The solution was filtered and evaporated in vacuo to give an oil residue which was purified using NPSCC (hexane/ethyl acetate as mobile phase) followed by normal phase HPLC (2:1 hexane/isopropanol as mobile phase) to afford the title compound as a light yellow oil: Data analogous to that of USYDS10.

27. Preparation of (E)-2-(3-methyl-2-buten-1-yl)-5,4'-dihydroxy-3',3-dimethoxystilbene (27, Equivalent to USYDS1)

The title compound was prepared using the procedure as described for compound 25 to give 27 as light yellow oil; $C_{21}H_{24}O_4$ $^1$H NMR (400 MHz, CDCl$_3$) δ 7.17 (d, J=16 Hz, 1H), 7.01 (dd, J=12, 2 Hz, 1H), 7.0 (d, J=2 Hz, 1H), 6.91 (d, J=8 Hz, 1H), 6.87 (d, J=16 Hz, 1H), 6.66 (t, J=2 Hz, 1H), 6.36 (t, J=2 Hz, 1H), 5.15 (m, 1H), 4.64 (s, 1H), 3.94 (s, 3H), 3.80 (s, 3H), 3.42 (d, J=7 Hz, 2H), 1.81 (d, J=1 Hz, 3H), 1.68 (d, J=1 Hz, 3H); $^{13}$C NMR (100 MHz, CDCl$_3$) δ 158.57, 154.37, 146.68, 145.60, 138.18, 130.61, 130.44, 130.27, 124.28, 123.67, 120.73, 120.58, 114.55, 108.26, 103.88, 98.18, 55.88, 55.71, 25.79, 24.48, 17.98; CI-MS: m/z 339 (M−1)$^-$; HRMS m/z 363.1566 (M+Na)$^+$, calcd 363.1572 for $C_{21}H_{24}O_4$Na.

28. Preparation of 2-(3-methyl-2-buten-1-yl)-5,4'-dihydroxy-3',3-dimethoxydihydro-stilbene (28)

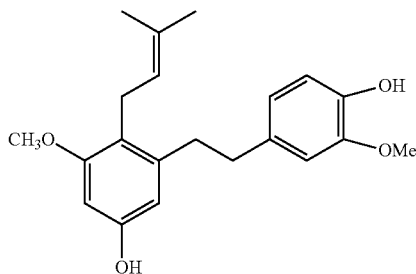

The title compound was obtained by hydrogenation of double bond on the side chain during removal of the benzyl group of compound 27. The title compound was obtained as a light yellow oil; $C_{21}H_{26}O_4$ $^1$H NMR (400 MHz, $CDCl_3$) δ 6.86 (d, J=8 Hz, 1H), 6.70 (dd, J=8, 2 Hz, 1H), 6.64 (d, J=2 Hz, 1H), 6.30 (d, J=2 Hz, 1H), 6.24 (d, J=2 Hz, 1H), 5.48 (s, 1H), 5.07 (m, 1H), 4.67 (s, 1H), 3.85 (s, 3H), 3.78 (s, 3H), 3.28 (d, J=6 Hz, 2H), 2.82 (m, 4H), 1.74 (d, J=1 Hz, 3H), 1.66 (d, J=1 Hz, 3H); $^{13}$C NMR (100 MHz, $CDCl_3$) δ 158.63, 154.23, 146.23, 143.73, 142.01, 133.93, 130.59, 123.87, 120.92, 120.67, 114.21, 111.02, 107.96, 96.90, 55.84, 55.60, 37.19, 35.49, 25.76, 24.38, 17.95; CI-MS: m/z 365 (M+Na)$^+$; HRMS m/z 365.1723 (M+Na)$^+$, calcd 365.1729 for $C_{21}H_{26}O_4Na$.

Biological Evaluations of Prenylated Polyhydroxystilbene Derivatives

1. Anticancer Activities of the Prenylated Polyhydroxystilbene Derivatives.

A) Seven prenylated polyhydroxystilbene derivatives, namely USYDS1, USYDS2, USYDS4, USYDS6, USYDS7, USYDS9 and USYDS13 were evaluated for inhibition of cell growth, as shown in table 1 below, against the 60 cell lines at a range of concentrations ($1\times10^{-8}$-$1\times10^{-4}$ M) at the National Cancer Institute (NCI), USA.

Methodology of the In Vitro Cancer Screen: General Method Adopted from NCI

The human tumor cell lines were grown in RPMI 1640 medium containing 5% fetal bovine serum and 2 mM L-glutamine. For a typical experiment, cells were inoculated into 96 well microtiter plates in 100 μL at plating densities ranging from 5,000 to 40,000 cells/well depending on the doubling time of individual cell lines. After cell inoculation, the microtiter plates were incubated at 37° C., 5% $CO_2$, 95% air and 100% relative humidity for 24 h prior to addition of the drugs.

After 24 h, two plates of each cell line were fixed in situ with trichloroacetic acid (TCA), to represent a measurement of the cell population for each cell line at the time of drug addition. Experimental drugs are solubilized in dimethyl sulfoxide (DMSO) at 400-fold the desired final maximum test concentration and stored frozen prior to use. At the time of drug addition, an aliquot of frozen concentrate was thawed and diluted to twice the desired final maximum test concentration with complete medium containing 50 μg/mL gentamicin. Aliquots of 100 μL of the drug were added to the appropriate microtiter wells already containing 100 μL of medium, resulting in the required final drug concentrations.

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 μL of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 μL) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 μL of 80% TCA (final concentration, 16% TCA), and the absorbance was read on an automated plate reader at a wavelength of 515 nm. The $GI_{50}$ value (concentration required for 50% inhibition of cell growth), TGI value (concentration required for total inhibition of cell growth) and $LC_{50}$ value (concentration required for 50% cell lethality or death) were calculated for each of USYDS1, USYDS2, USYDS4, USYDS6, USYDS7, USYDS9 and USYDS13, and the results are presented in tables 1 to 3 below.

TABLE 1

Effect of pPHOS USYDS1, USYDS2 and USYDS13 on human cancerous cells growth.

| | Compounds | | | | | | | | |
|---|---|---|---|---|---|---|---|---|---|
| | USYDS1 (μM) | | | USYDS2 (μM) | | | USYDS13 (μM) | | |
| | $GI_{50}$ | TGI | $LC_{50}$ | $GI_{50}$ | TGI | $LC_{50}$ | $GI_{50}$ | TGI | $LC_{50}$ |
| Leukemia | | | | | | | | | |
| CCRF-CEM | 0.35 | 24.6 | >100 | 5.06 | >100 | >100 | 6.56 | >100 | >100 |
| HL-60 (TB) | 0.02 | 0.06 | 68.9 | 1.34 | 9.77 | >100 | 2.55 | 17.1 | >100 |
| K-562 | 0.04 | 11.7 | >100 | 0.48 | >100 | >100 | 4.08 | 57.5 | >100 |
| MOLT-4 | 0.43 | 12.3 | 80.2 | 4.16 | 28.3 | >100 | 2.95 | 13.7 | >100 |
| RPMI-8226 | 0.11 | 14.8 | >100 | 4.32 | 52.8 | >100 | 9.05 | 51.6 | >100 |
| SR | 0.04 | 24.4 | >100 | 0.54 | >100 | >100 | 2.80 | >100 | >100 |
| Non-Small Cell Lung Cancer | | | | | | | | | |
| A549/ATCC | 0.50 | 11.3 | 40.3 | 3.28 | 13.0 | 42.1 | 4.01 | 20.4 | >100 |
| EKVX | 10.8 | 24.3 | 54.4 | 9.04 | 25.2 | 66.4 | 12.8 | 54.6 | >100 |
| HOP-62 | 0.44 | 16.0 | 42.2 | 4.44 | 18.5 | 43.4 | 5.66 | 20.4 | 53.7 |
| HOP-92 | 0.06 | 12.3 | 39.6 | 3.98 | 21.1 | 60.1 | 5.96 | 30.5 | >100 |

TABLE 1-continued

Effect of pPHOS USYDS1, USYDS2 and USYDS13 on human cancerous cells growth.

| | Compounds | | | | | | | | |
|---|---|---|---|---|---|---|---|---|---|
| | USYDS1 (µM) | | | USYDS2 (µM) | | | USYDS13 (µM) | | |
| | $GI_{50}$ | TGI | $LC_{50}$ | $GI_{50}$ | TGI | $LC_{50}$ | $GI_{50}$ | TGI | $LC_{50}$ |
| NCI-H226 | 3.13 | 13.3 | 45.6 | 5.43 | 19.1 | 46.4 | 10.9 | 50.1 | >100 |
| NCI-H23 | 0.28 | 15.1 | 62.5 | 2.89 | 23.6 | >100 | 5.66 | 28.0 | >100 |
| NCI-H322M | 11.8 | 25.7 | 55.9 | 9.64 | 22.7 | 52.3 | 5.90 | 28.5 | >100 |
| NCI-H460 | 0.23 | 1.38 | 42.0 | 2.47 | 10.9 | 58.7 | 3.09 | 15.6 | >100 |
| NCI-H522 | 0.02 | — | 44.8 | 1.14 | 3.57 | 14.7 | 2.13 | 59.8 | 25.6 |
| Colon Cancer | | | | | | | | | |
| COLO 205 | 3.86 | 16.1 | 42.6 | 17.3 | 31.7 | 57.9 | 15.6 | 28.9 | 53.8 |
| HCC-2998 | 1.07 | 11.5 | 35.8 | 4.61 | 17.3 | 46.4 | 11.0 | 30.6 | 85.3 |
| HCT-116 | 0.30 | 11.1 | 40.4 | 2.09 | 11.9 | 40.0 | 4.33 | 15.6 | 45.6 |
| HCT-15 | 0.05 | 16.1 | >100 | 0.76 | 17.8 | 97.3 | 4.25 | 20.5 | 84.5 |
| HT29 | 4.73 | 15.3 | 44.4 | 17.4 | 32.2 | 59.6 | 17.8 | 36.9 | 76.8 |
| KM12 | 0.32 | 13.9 | 46.7 | 2.09 | 11.7 | 45.0 | 3.15 | 16.1 | 49.0 |
| SW-620 | 0.04 | 15.1 | 44.3 | 0.53 | 14.0 | 40.7 | 3.98 | 15.9 | 42.8 |
| CNS Cancer | | | | | | | | | |
| SF-268 | 0.25 | 14.1 | 50.2 | 4.50 | 19.2 | 51.6 | 6.17 | 32.9 | >100 |
| SF-295 | 0.65 | 16.2 | 55.7 | 3.94 | 14.7 | 49.2 | 5.22 | 23.5 | 77.5 |
| SF-539 | 0.04 | 14.4 | 48.6 | 1.92 | 13.8 | 50.2 | 7.32 | 29.9 | >100 |
| SNB-19 | 0.17 | 19.3 | 51.5 | 5.02 | 20.4 | 53.6 | 8.02 | 24.2 | 64.5 |
| SNB-75 | 0.03 | 20.2 | 72.0 | 2.14 | 10.3 | 55.8 | 5.47 | 36.6 | >100 |
| U251 | 0.37 | 10.9 | 36.0 | 2.96 | 14.7 | 41.0 | 5.47 | 20.7 | 57.6 |
| Melanoma | | | | | | | | | |
| LOX IMVI | 0.05 | 16.2 | 58.8 | 1.56 | 19.4 | >100 | 4.48 | 20.2 | 80.0 |
| MALME-3M | 3.47 | 25.8 | 78.3 | 1.88 | 26.2 | 94.9 | 5.53 | 32.1 | >100 |
| M14 | 0.04 | 13.9 | 44.0 | 0.53 | 15.4 | 49.4 | 4.92 | 18.5 | 51.6 |
| MDA-MB-435 | 0.03 | 13.8 | 43.0 | 0.34 | 11.0 | 41.3 | 3.08 | 15.9 | >100 |
| SK-MEL-2 | 0.32 | 10.6 | 38.0 | 1.25 | 9.59 | 41.6 | 3.09 | 9.37 | 40.2 |
| SK-MEL-28 | 10.9 | 23.8 | 51.7 | 5.04 | 19.4 | 46.7 | 5.64 | 22.5 | 70.5 |
| SK-MEL-5 | 0.05 | 0.75 | 5.99 | 1.58 | 11.5 | 34.3 | 2.50 | 8.54 | 29.2 |
| UACC-257 | 2.53 | 17.7 | 45.4 | 7.89 | 20.6 | 46.0 | 5.35 | 18.1 | 44.0 |
| UACC-62 | 1.62 | 18.3 | 46.6 | 3.73 | 15.9 | 44.6 | 5.30 | 19.7 | 58.8 |
| Ovarian Cancer | | | | | | | | | |
| IGROV1 | 2.65 | 27.9 | >100 | 5.84 | 46.7 | >100 | 6.70 | 86.2 | >100 |
| OVCAR-3 | 0.26 | — | 37.3 | 3.02 | 10.7 | 36.1 | 7.98 | 39.8 | >100 |
| OVCAR-4 | 0.58 | 18.4 | 52.0 | 5.34 | 28.0 | >100 | 9.68 | 74.8 | >100 |
| OVCAR-5 | 6.0 | 21.4 | 55.3 | 10.1 | 24.8 | 60.9 | 13.9 | 79.3 | >100 |
| OVCAR-8 | 0.08 | 11.7 | 50.0 | 2.80 | 14.8 | 44.6 | 5.48 | 59.8 | >100 |
| ADR-RES | 0.03 | — | 70.7 | 0.40 | 4.95 | >100 | 4.41 | >100 | >100 |
| SK-OV-3 | 0.19 | 11.6 | 34.7 | 3.69 | 14.9 | 38.9 | 7.96 | 36.2 | >100 |
| Renal Cancer | | | | | | | | | |
| 786-0 | 0.48 | 14.0 | >100 | 3.55 | 15.9 | 98.8 | 5.24 | 24.5 | >100 |
| A498 | 1.84 | 8.45 | 32.2 | 10.3 | 23.8 | 55.2 | 3.88 | 21.0 | 63.5 |
| ACHN | 0.07 | 14.0 | 44.6 | 3.76 | 17.5 | 52.1 | 5.11 | >100 | >100 |
| CAKI-1 | 4.77 | 39.3 | >100 | 6.13 | >100 | >100 | 5.90 | >100 | >100 |
| RXF-393 | 0.03 | — | 39.1 | 1.35 | 5.46 | 23.6 | 5.48 | 18.9 | 46.5 |
| SN12C | 0.99 | 16.9 | 54.2 | 4.02 | 18.8 | 60.2 | 7.16 | >100 | >100 |
| TK-10 | 4.10 | 15.7 | 40.5 | 4.69 | 14.3 | 40.1 | 6.98 | 31.4 | >100 |
| UO-31 | 0.25 | 16.0 | 51.3 | 2.60 | 16.9 | 48.9 | 4.16 | 38.1 | >100 |
| Prostate Cancer | | | | | | | | | |
| PC-3 | 0.42 | 16.1 | 47.9 | 3.84 | 18.7 | 65.8 | 6.36 | >100 | >100 |
| DU-145 | 0.06 | 12.7 | 38.6 | 3.05 | 12.5 | 37.8 | 6.82 | 31.6 | >100 |
| Breast Cancer | | | | | | | | | |
| MCF7 | 0.23 | 13.0 | 52.9 | 1.24 | 15.0 | 41.0 | 0.68 | 19.9 | 82.7 |
| MDA-MB-231 | 0.15 | 2.43 | 61.2 | 0.25 | 2.10 | 15.7 | 1.63 | 7.82 | >100 |
| BT-549 | | | | | | | | | |
| HS 578T | 0.02 | — | >100 | 1.28 | 10.3 | >100 | 2.40 | 15.0 | >100 |
| T-47D | 0.72 | 19.8 | 67.4 | 5.66 | 33.6 | >100 | 2.92 | 14.7 | 70.5 |
| MDA-MB-468 | 0.36 | 8.37 | 33.2 | 2.72 | 9.41 | 36.8 | 1.68 | 7.63 | >100 |

TABLE 2

Effect of pPHOS USYDS4, USYDS9 and USYDS6 on human cancerous cells growth

| | Compounds | | | | | | | | |
|---|---|---|---|---|---|---|---|---|---|
| | USYDS4 (µM) | | | USYDS9 (µM) | | | USYDS6 (µM) | | |
| | $GI_{50}$ | TGI | $LC_{50}$ | $GI_{50}$ | TGI | $LC_{50}$ | $GI_{50}$ | TGI | $LC_{50}$ |
| Leukemia | | | | | | | | | |
| CCRF-CEM | 3.50 | >100 | >100 | 2.14 | >100 | >100 | 2.96 | 9.17 | 82.1 |
| HL-60 (TB) | 2.59 | 6.04 | >100 | 0.20 | 0.43 | 0.95 | 2.07 | 4.83 | 15.4 |
| K-562 | 2.35 | >100 | >100 | 0.33 | 13.9 | >100 | 1.46 | 4.13 | 22.6 |
| MOLT-4 | 4.31 | 21.6 | >100 | 1.27 | 6.77 | >100 | 1.59 | 4.27 | 16.8 |
| RPMI-8226 | 2.35 | 25.4 | >100 | 0.45 | >100 | >100 | 2.34 | 5.61 | 62.0 |
| SR | 0.95 | >100 | >100 | — | — | — | — | — | — |
| Non-Small Cell Lung Cancer | | | | | | | | | |
| A549/ATCC | 4.74 | 25.6 | >100 | 2.62 | 41.5 | >100 | 2.69 | 8.42 | 33.7 |
| EKVX | 9.55 | 59.6 | >100 | 26.4 | >100 | >100 | 7.19 | 21.4 | 54.4 |
| HOP-62 | 6.49 | 26.3 | 83.4 | 2.87 | >100 | >100 | 5.11 | 17.5 | 44.0 |
| HOP-92 | 1.92 | 13.6 | 62.3 | 0.62 | >100 | >100 | 1.86 | 4.67 | 14.5 |
| NCI-H226 | 5.14 | 23.1 | 78.0 | 18.6 | 57.9 | >100 | 1.47 | 30.1 | 61.5 |
| NCI-H23 | 3.42 | 20.8 | 81.9 | 1.43 | >100 | >100 | 3.38 | 15.7 | 47.6 |
| NCI-H322M | 12.8 | 54.7 | >100 | 0.76 | >100 | >100 | 1.16 | 25.5 | 56.2 |
| NCI-H460 | 3.65 | 20.3 | >100 | 0.47 | 10.3 | 75.7 | 1.89 | 3.90 | 8.06 |
| NCI-H522 | 1.07 | 2.54 | 6.04 | 0.15 | 0.45 | 44.8 | 2.18 | 5.15 | 17.8 |
| Colon Cancer | | | | | | | | | |
| COLO 205 | 9.72 | 23.0 | 53.5 | 21.7 | 83.6 | >100 | 16.0 | 30.2 | 57.2 |
| HCC-2998 | 5.16 | 19.0 | 53.4 | 4.18 | 21.2 | >100 | 2.81 | 8.78 | 32.2 |
| HCT-116 | 4.55 | 16.0 | 40.6 | 1.40 | 12.8 | 75.0 | 1.89 | 3.78 | 7.54 |
| HCT-15 | 1.77 | 34.9 | >100 | 0.43 | >100 | >100 | 2.13 | 6.26 | 48.2 |
| HT29 | 16.3 | 32.5 | 64.7 | 18.6 | 46.6 | >100 | 5.44 | 17.6 | 48.3 |
| KM12 | 3.27 | 14.2 | 46.5 | 0.52 | 12.2 | 63.9 | 2.21 | 4.37 | 8.64 |
| SW-620 | 2.97 | 16.6 | 46.5 | 0.31 | 15.3 | 75.0 | 1.84 | 3.54 | 6.82 |
| CNS Cancer | | | | | | | | | |
| SF-268 | 3.89 | 23.2 | >100 | 0.63 | 37.6 | >100 | 2.78 | 8.97 | 44.3 |
| SF-295 | 7.29 | 24.3 | 70.9 | 2.60 | 20.5 | >100 | 6.78 | 20.8 | 53.2 |
| SF-539 | 3.45 | 22.3 | 97.5 | 0.28 | 1.02 | >100 | 4.48 | 17.6 | 57.1 |
| SNB-19 | 10.5 | 25.8 | 63.8 | 0.55 | >100 | >100 | 6.38 | 20.6 | 52.7 |
| SNB-75 | 1.77 | 9.11 | 48.3 | 0.24 | — | >100 | 6.67 | 21.4 | 54.0 |
| U251 | 3.67 | 15.6 | 45.5 | 0.59 | 19.6 | >100 | 2.33 | 5.31 | 16.7 |
| Melanoma | | | | | | | | | |
| LOX IMVI | 3.82 | 19.3 | 58.5 | 0.64 | 58.6 | >100 | 1.76 | 3.42 | 6.68 |
| MALME-3M | 7.25 | 30.6 | >100 | 0.62 | >100 | >100 | 2.80 | 8.56 | 37.1 |
| M14 | 0.91 | 15.4 | 46.3 | 0.30 | 5.69 | >100 | 2.82 | 8.46 | 33.4 |
| MDA-MB-435 | 0.36 | 21.6 | >100 | 0.13 | 0.42 | >100 | 3.37 | 10.8 | 42.1 |
| SK-MEL-2 | 2.18 | 6.57 | 31.0 | 2.17 | 12.1 | >100 | 13.1 | 33.6 | 86.1 |
| SK-MEL-28 | 9.18 | 27.6 | 77.9 | 8.14 | >100 | >100 | 11.2 | 24.0 | 51.3 |
| SK-MEL-5 | 1.42 | 8.35 | 30.0 | 0.39 | 2.52 | >100 | 2.29 | 6.17 | 22.1 |
| UACC-257 | 5.44 | 19.4 | 48.6 | 6.15 | 59.2 | >100 | 3.49 | 14.4 | 39.8 |
| UACC-62 | 4.53 | 16.8 | 44.4 | 3.22 | 34.8 | >100 | 10.3 | 23.5 | 53.8 |
| Ovarian Cancer | | | | | | | | | |
| IGROV1 | 3.74 | 44.8 | >100 | 4.57 | >100 | >100 | 5.23 | 17.7 | 54.1 |
| OVCAR-3 | 3.98 | 15.0 | 44.9 | 0.90 | 3.84 | 24.8 | 2.10 | 4.31 | 8.85 |
| OVCAR-4 | 3.98 | 50.4 | >100 | 5.48 | >100 | >100 | 4.40 | 16.1 | 43.5 |
| OVCAR-5 | 15.9 | 51.4 | >100 | 30.7 | >100 | >100 | 5.86 | 20.0 | 53.3 |
| OVCAR-8 | 4.94 | 31.1 | >100 | 0.50 | 38.3 | >100 | 2.95 | 9.51 | 42.9 |
| ADR-RES | 1.11 | 48.3 | >100 | 0.29 | 3.69 | >100 | 3.46 | 15.2 | 51.2 |
| SK-OV-3 | 8.91 | 57.0 | >100 | 0.50 | 5.12 | >100 | 13.9 | 27.1 | 53.2 |
| Renal Cancer | | | | | | | | | |
| 786-0 | 4.41 | 20.5 | >100 | 2.99 | 18.7 | >100 | 2.46 | 6.96 | 28.8 |
| A498 | 9.07 | 23.5 | 55.2 | 10.3 | 53.5 | >100 | 11.7 | 25.0 | 53.1 |
| ACHN | 4.57 | >100 | >100 | 0.66 | >100 | >100 | 3.94 | 14.6 | 50.4 |
| CAKI-1 | 5.25 | >100 | >100 | 19.1 | >100 | >100 | 8.37 | 22.6 | 55.7 |
| RXF-393 | 2.17 | 15.3 | 46.0 | 0.23 | 0.63 | >100 | 2.15 | 5.39 | 18.7 |
| SN12C | 3.94 | 20.0 | 74.1 | 1.76 | 83.5 | >100 | 2.85 | 7.98 | 30.8 |
| TK-10 | 3.87 | 9.66 | >100 | 5.34 | 41.2 | >100 | 3.36 | 9.33 | 31.2 |
| UO-31 | 3.31 | 20.7 | 66.4 | 0.46 | >100 | >100 | 2.51 | 7.50 | 33.5 |
| Prostate Cancer | | | | | | | | | |
| PC-3 | 4.47 | 22.0 | 87.9 | 2.92 | >100 | >100 | 1.80 | 3.89 | 8.44 |
| DU-145 | 6.37 | 44.6 | >100 | 0.35 | 2.62 | >100 | 3.47 | 12.9 | 40.1 |

TABLE 2-continued

Effect of pPHOS USYDS4, USYDS9 and USYDS6 on human cancerous cells growth

| | Compounds | | | | | | | | |
|---|---|---|---|---|---|---|---|---|---|
| | USYDS4 (µM) | | | USYDS9 (µM) | | | USYDS6 (µM) | | |
| | $GI_{50}$ | TGI | $LC_{50}$ | $GI_{50}$ | TGI | $LC_{50}$ | $GI_{50}$ | TGI | $LC_{50}$ |
| Breast Cancer | | | | | | | | | |
| MCF7 | 2.57 | 18.2 | 51.1 | 2.81 | >100 | >100 | 4.02 | 18.0 | 60.5 |
| MDA-MB-231 | 1.04 | 18.4 | >100 | 0.38 | 2.61 | >100 | 1.72 | 4.54 | 17.2 |
| HS 578T | 1.00 | 7.11 | >100 | 0.20 | 0.73 | >100 | 1.67 | 5.29 | 35.8 |
| T-47D | 2.13 | 6.93 | >100 | 4.78 | 36.9 | >100 | 5.03 | 20.3 | 57.9 |
| MDA-MB-468 | 2.53 | 9.51 | 55.1 | 2.42 | 8.48 | >100 | 2.30 | 6.39 | 26.0 |

TABLE 3

Effect of pPHOS USYDS7 on human cancerous cells growth

| | Compound USYDS7 (µM) | | |
|---|---|---|---|
| | $GI_{50}$ | TGI | $LC_{50}$ |
| Leukemia | | | |
| CCRF-CEM | 2.73 | 8.48 | 71.2 |
| HL-60 (TB) | 2.39 | 5.06 | 13.8 |
| K-562 | 2.14 | 4.78 | 17.4 |
| MOLT-4 | 2.01 | 5.19 | 26.5 |
| RPMI-8226 | 2.31 | 6.01 | 61.1 |
| Non-Small Cell Lung Cancer | | | |
| A549/ATCC | 1.88 | 4.06 | 8.78 |
| EKVX | 4.25 | 14.7 | 44.9 |
| HOP-62 | 3.67 | 15.0 | 51.6 |
| HOP-92 | 1.52 | 4.21 | 14.2 |
| NCI-H226 | 2.28 | 6.24 | 28.1 |
| NCI-H23 | 1.81 | 5.22 | 29.5 |
| NCI-H322M | 5.29 | 18.1 | 44.7 |
| NCI-H460 | 1.64 | 3.22 | 6.33 |
| NCI-H522 | 1.61 | 3.57 | 7.92 |
| Colon Cancer | | | |
| COLO 205 | 1.79 | 4.34 | 12.2 |
| HCC-2998 | 1.95 | 4.26 | 9.34 |
| HCT-116 | 1.57 | 3.02 | 5.82 |
| HCT-15 | 1.29 | 3.78 | 22.0 |
| HT29 | 3.64 | 10.8 | 45.8 |
| KM12 | 1.93 | 3.88 | 7.79 |
| SW-620 | 1.58 | 3.19 | 6.42 |
| CNS Cancer | | | |
| SF-268 | 2.26 | 5.47 | 22.7 |
| SF-295 | 3.37 | 11.4 | 44.6 |
| SF-539 | 2.21 | 6.14 | 35.2 |
| SNB-19 | 2.80 | 8.64 | 39.9 |
| SNB-75 | 2.98 | 12.8 | 49.1 |
| U251 | 1.49 | 2.93 | 5.74 |
| Prostate Cancer | | | |
| PC-3 | 2.02 | 4.57 | 11.3 |
| DU-145 | 2.65 | 7.62 | 28.3 |
| Melanoma | | | |
| LOX IMVI | 1.71 | 3.41 | 6.81 |
| MALME-3M | 1.97 | 4.46 | 10.4 |
| M14 | 1.79 | 3.71 | 7.73 |
| MDA-MB-435 | 2.29 | 6.47 | 31.7 |
| SK-MEL-2 | 3.20 | 7.82 | 42.9 |
| SK-MEL-28 | 3.65 | 11.8 | 36.7 |
| SK-MEL-5 | 1.80 | 3.68 | 7.54 |
| UACC-257 | 2.18 | 5.93 | 23.0 |
| UACC-62 | 2.80 | 7.84 | 31.5 |
| Ovarian Cancer | | | |
| IGROV1 | 3.12 | 8.39 | 36.7 |
| OVCAR-3 | 1.82 | 3.36 | 6.19 |
| OVCAR-4 | 2.85 | 11.1 | 66.8 |
| OVCAR-5 | 3.04 | 11.6 | 39.0 |
| OVCAR-8 | 1.68 | 3.65 | 7.95 |
| ADR-RES | 2.23 | 7.90 | 42.4 |
| SK-OV-3 | 5.98 | 19.4 | 46.5 |
| Renal Cancer | | | |
| 786-0 | 1.99 | 4.47 | 10.2 |
| A498 | 11.1 | 23.8 | 50.8 |
| ACHN | 2.58 | 9.12 | 37.6 |
| CAKI-1 | 4.24 | 16.2 | 49.0 |
| RXF-393 | 1.53 | 3.23 | 6.80 |
| SN12C | 1.65 | 3.16 | 6.03 |
| TK-10 | 3.62 | 11.2 | 34.3 |
| UO-31 | 1.60 | 3.46 | 7.46 |
| Breast Cancer | | | |
| MCF7 | 2.10 | 12.0 | 57.9 |
| MDA-MB-231 | 1.49 | 3.89 | 10.7 |
| HS 578T | 1.84 | 8.09 | 50.9 |
| T-47D | 1.88 | 6.09 | 43.5 |
| MDA-MB-468 | 2.12 | 4.84 | 13.9 |

In summary, all the prenylated polyhydroxystilbene derivatives USYDS1 to USYDS9 and USYDS13 exhibited structure dependent inhibition of cancerous cell growth. In some cell lines, growth was inhibited at nano-molar concentrations. USYDS1 displayed the most potent activity followed by USYDS9 then USYDS2 in the inhibition of cancerous cell growth. The other pPHOS compounds tested were shown to be moderate inhibitors. FIGS. 3 to 9 show dose response curves for the inhibition of human cancerous cell growth, for the various cell lines exhibited in the table above, by compounds USYDS1 to USYDS9 and USYDS13.

Worthy of note is that these pPHOS required at least a 10 fold excess in concentration to cause cell death ($LC_{50}$ values) or cause necrosis, over that required to inhibit cell growth ($GI_{50}$ values). This indicates that the pPHOS were likely to cause the cancer cells to undergo programmed cell death (apoptosis) or cell cycle arrest.

B) Two prenylated polyhydroxystilbene derivatives, namely USYDS10 and USYDS14 were evaluated for inhibition of cell growth, as shown in Table 4A and 4B below, against the cell lines indicated at a range of concentrations ($1 \times 10^{-8}$-$1 \times 10^{-4}$ M) at the National Cancer Institute (NCI), USA.

TABLE 4A

Inhibitory effect on cancer cells growth of USYDS10

| | GI50 | TGI | LC50 |
|---|---|---|---|
| Leukemia | | | |
| HL-60(TB) | 3.27E−7 | 1.88E−6 | >1.00E−4 |
| K-562 | 3.86E−7 | 3.17E−5 | >1.00E−4 |
| MOLT | 5.96E−7 | 1.99E−5 | >1.00E−4 |
| RPMI | 3.24E−7 | 1.63E−5 | >1.00E−4 |
| SR | 1.88E−7 | >1.00E−4 | >1.00E−4 |
| Non-Small Cell Lung Cancer | | | |
| A549/ATCC | 6.60E−7 | 2.25E−5 | >1.00E−4 |
| EKVX | 1.22E−5 | 7.34E−5 | >1.00E−4 |
| HOP | 5.81E−7 | 1.77E−5 | 4.23E−5 |
| HOP | 3.98E−7 | 2.63E−5 | 9.32E−5 |
| NCI-H226 | 5.35E−6 | 3.50E−5 | >1.00E−4 |
| NCI-H23 | 3.80E−7 | 1.52E−5 | 7.83E−5 |
| NCI-H322M | 1.18E−5 | 3.14E−5 | 8.37E−5 |
| NCI-H460 | 3.81E−7 | 1.29E−5 | 6.61E−5 |
| NCI-H522 | 3.49E−7 | 1.46E−5 | 4.22E−5 |
| Colon Cancer | | | |
| COLO | 1.53E−5 | 2.97E−5 | 5.77E−5 |
| HCC-2998 | 1.81E−6 | 1.19E−5 | 3.98E−5 |
| HCT-116 | 4.80E−7 | 1.30E−5 | 4.27E−5 |
| HCT-15 | 4.98E−7 | 2.09E−5 | >1.00E−4 |
| HT29 | 5.72E−6 | 2.13E−5 | 6.90E−5 |
| KM12 | 4.97E−7 | 1.53E−5 | 8.58E−5 |
| SW-620 | 3.62E−7 | 2.15E−5 | 8.55E−5 |
| CNS Cancer | | | |
| SF-268 | 1.40E−6 | 4.96E−5 | >1.00E−4 |
| SF-295 | 2.01E−6 | 1.91E−5 | >1.00E−4 |
| SF-539 | 3.76E−7 | 1.29E−5 | 4.17E−5 |
| SNB-19 | 6.13E−7 | 2.28E−5 | >1.00E−4 |
| SNB-75 | 2.36E−7 | 1.22E−5 | 3.61E−5 |
| U251 | 4.19E−7 | 1.62E−5 | 7.88E−5 |
| Melanoma | | | |
| LOX IMVI | 5.72E−7 | 1.93E−5 | 8.00E−5 |
| MALME-3M | 1.87E−5 | 4.17E−5 | 9.29E−5 |
| M14 | 2.84E−7 | 1.42E−5 | 4.16E−5 |
| MDA-MB-435 | 3.85E−8 | 2.56E−7 | >1.00E−4 |
| SK-MEL-2 | 5.76E−7 | 3.26E−5 | >1.00E−4 |
| SK-MEL-28 | 5.72E−7 | 1.69E−5 | 4.30E−5 |
| SK-MEL-5 | 2.91E−7 | 1.27E−5 | 3.60E−5 |
| UACC-257 | 1.17E−5 | 2.94E−5 | 7.37E−5 |
| UACC-62 | 5.21E−7 | 1.55E−5 | 4.28E−5 |
| Ovarian Cancer | | | |
| IGROV1 | 2.03E−6 | >1.00E−4 | >1.00E−4 |
| OVCAR-3 | 3.72E−7 | 2.03E−5 | >1.00E−4 |
| OVCAR-4 | 1.03E−6 | 1.82E−5 | 5.77E−5 |
| OVCAR-5 | 8.92E−6 | 2.80E−5 | 8.31E−5 |
| OVCAR-8 | 4.67E−7 | 6.50E−5 | >1.00E−4 |
| NCI/ADR-RES | 1.83E−7 | 8.04E−7 | >1.00E−4 |
| SK-OV-3 | 4.22E−7 | 1.14E−5 | 3.42E−5 |
| Renal Cancer | | | |
| 786-0 | 6.81E−7 | 2.01E−5 | 7.45E−5 |
| A498 | 2.17E−6 | 7.85E−6 | 3.48E−5 |
| ACHN | 9.03E−7 | 3.79E−5 | >1.00E−4 |
| CAKI-1 | 5.39E−7 | 6.68E−5 | >1.00E−4 |
| RXF 393 | 2.21E−7 | | 3.76E−5 |
| SN12C | 6.71E−7 | 2.98E−5 | >1.00E−4 |
| TK-10 | 9.55E−6 | 5.15E−5 | >1.00E−4 |
| UO-31 | 8.78E−7 | 2.17E−5 | 9.52E−5 |
| Prostate Cancer | | | |
| PC-3 | 2.27E−6 | 3.12E−5 | >1.00E−4 |
| DU-145 | 4.42E−7 | 2.05E−5 | >1.00E−4 |
| Breast Cancer | | | |
| MCF7 | 3.32E−7 | 1.30E−5 | 5.06E−5 |
| MDA-MB-231/ATCC | 6.42E−7 | 3.20E−5 | >1.00E−4 |
| HS 578T | 2.92E−7 | 2.60E−5 | >1.00E−4 |
| BT-549 | 7.98E−7 | 1.90E−5 | 4.93E−5 |
| T-47D | 1.47E−6 | 2.47E−5 | >1.00E−4 |
| MDA-MB-468 | 3.73E−7 | 1.44E−5 | 4.49E−5 |

TABLE 4B

Inhibitory effect on cancer cells growth of USYDS14

| | GI50 | TGI | LC50 |
|---|---|---|---|
| Leukemia | | | |
| HL-60(TB) | 4.06E−6 | 1.63E−5 | >1.00E−4 |
| K-562 | 8.33E−7 | 1.42E−5 | >1.00E−4 |
| MOLT-4 | 4.03E−6 | 2.10E−5 | >1.00E−4 |
| RPMI-8226 | 4.07E−6 | 2.45E−5 | >1.00E−4 |
| SR | 6.70E−7 | 2.46E−5 | >1.00E−4 |
| Non-Small Cell Lung Cancer | | | |
| A549/ATCC | 4.33E−6 | 1.65E−5 | 4.55E−5 |
| EKVX | 6.45E−6 | 2.12E−5 | 5.17E−5 |
| HOP-62 | 1.43E−6 | 3.77E−6 | 9.98E−6 |
| HOP-92 | 1.49E−6 | 7.58E−6 | 3.29E−5 |
| NCI-H226 | 1.72E−6 | 3.60E−6 | 7.52E−6 |
| NCI-H23 | 2.92E−6 | 1.73E−5 | 5.76E−5 |
| NCI-H322M | 1.25E−5 | 2.57E−5 | 5.28E−5 |
| NCI-H460 | 3.87E−6 | 1.49E−5 | 5.12E−5 |
| NCI-H522 | 7.50E−7 | 2.26E−6 | 5.85E−6 |
| Colon Cancer | | | |
| COLO 205 | 1.46E−5 | 2.85E−5 | 5.57E−5 |
| HCC-2998 | 2.90E−6 | 1.06E−5 | 4.07E−5 |
| HCT-116 | 4.20E−6 | 1.60E−5 | 4.66E−5 |
| HCT-15 | 2.06E−6 | 1.04E−5 | 4.33E−5 |
| HT29 | 1.40E−5 | 2.91E−5 | 6.09E−5 |
| KM12 | 3.74E−6 | 1.44E−5 | 5.74E−5 |
| SW-620 | 2.88E−6 | 1.67E−5 | 6.38E−5 |
| CNS Cancer | | | |
| SF-268 | 4.65E−6 | 1.78E−5 | 4.85E−5 |
| SF-295 | 3.91E−6 | 1.53E−5 | 4.31E−5 |
| SF-539 | 2.96E−6 | 1.05E−5 | 3.78E−5 |
| SNB-19 | 5.01E−6 | 2.01E−5 | 5.22E−5 |
| SNB-75 | 1.79E−6 | 7.80E−6 | 2.93E−5 |
| U251 | 3.09E−6 | 1.27E−5 | 3.94E−5 |
| Melanoma | | | |
| LOX IMVI | 1.36E−6 | 3.37E−6 | 8.35E−6 |
| MALME-3M | 3.14E−6 | 2.18E−5 | 5.48E−5 |
| M14 | 2.95E−6 | 1.36E−5 | 5.00E−5 |
| MDA-MB-435 | 3.73E−7 | 8.45E−6 | 4.00E−5 |
| SK-MEL-2 | 3.72E−6 | 1.25E−5 | 4.12E−5 |
| SK-MEL-28 | 3.05E−6 | 1.64E−5 | 4.16E−5 |
| SK-MEL-5 | 5.54E−7 | 1.87E−6 | 4.46E−6 |
| UACC-257 | 1.02E−5 | 2.35E−5 | 5.40E−5 |
| UACC-62 | 2.61E−6 | 1.32E−5 | 3.91E−5 |
| Ovarian Cancer | | | |
| IGROV1 | 3.65E−6 | 1.37E−5 | 6.54E−5 |
| OVCAR-3 | 3.52E−6 | 1.35E−5 | 4.11E−5 |
| OVCAR-4 | 2.98E−6 | 1.36E−5 | 3.86E−5 |
| OVCAR-5 | 1.24E−5 | 2.58E−5 | 5.36E−5 |
| OVCAR-8 | 3.59E−6 | 1.56E−5 | 6.49E−5 |
| NCI/ADR-RES | 7.80E−7 | 1.14E−5 | 4.93E−5 |
| SK-OV-3 | 2.85E−6 | 1.37E−5 | 3.72E−5 |
| Renal Cancer | | | |
| 786-0 | 3.44E−6 | 1.18E−5 | 4.00E−5 |
| A498 | 1.30E−5 | 2.66E−5 | 5.46E−5 |
| ACHN | 2.98E−6 | 1.25E−5 | 3.65E−5 |
| CAKI-1 | 3.59E−6 | 1.75E−5 | 4.54E−5 |
| RXF 393 | 1.07E−6 | 3.58E−6 | 1.48E−5 |
| SN12C | 3.61E−6 | 1.51E−5 | 4.20E−5 |
| TK-10 | 3.79E−6 | 1.21E−5 | 3.54E−5 |

TABLE 4B-continued

Inhibitory effect on cancer cells growth of USYDS14

|  | GI50 | TGI | LC50 |
|---|---|---|---|
| UO-31 | 3.71E−6 | 1.79E−5 | 4.63E−5 |
| Prostate Cancer | | | |
| PC-3 | 6.65E−6 | 2.16E−5 | 5.50E−5 |
| DU-145 | 8.20E−6 | 2.11E−5 | 4.75E−5 |
| Breast Cancer | | | |
| MCF7 | 2.74E−6 | 1.18E−5 | 4.19E−5 |
| MDA-MB-231/ATCC | 3.15E−6 | 1.43E−5 | 4.53E−5 |
| HS 578T | 2.71E−6 | 2.05E−5 | >1.00E−4 |
| BT-549 | 4.27E−6 | 1.63E−5 | 4.69E−5 |
| T-47D | 2.71E−6 | 7.84E−6 | 6.18E−5 |
| MDA-MB-468 | 1.42E−6 | 4.12E−6 | 1.64E−5 |

In summary, all the prenylated polyhydroxystilbene derivatives USYDS10 and USYDS14 exhibited structure dependent inhibition of cancerous cell growth.

2. Calculated Log Partition Coefficients (Log P) Values of Various Hydroxystilbenes.

The calculated Log P values for USYDS1 and USYDS2 and known hydroxystilbenes are presented in the table 5 below.

TABLE 5

Calculated Log P values of various hydroxystilbenes

| Compound USYDS2 | 5.37 | Rhapontigenin | 2.82 |
| Compound USYDS1 | 5.58 | Compound USYDS1 without a prenyl group. | 3.49 |
| Resveratrol | 3.14 | Pinosylvin | 3.68 |
| Piceatannol | 1.90 | | |

The potent inhibition of pPHOS compounds, for example USYDS1 and USYDS2, may be explained in terms of their increased hydrophobicity, as demonstrated by their calculated Log partition coefficient (Log P) values. USYDS1 and USYDS2 have Log P values almost twice that of the hydroxystilbene resveratrol. The effects of Log P on therapeutic compounds relate primarily to tissue penetration and distribution. Higher Log P values will enable compounds to more easily cross cell membranes and enter cells.

3. Effect of Prenylated Polyhydroxystilbene Derivatives on UV-Irradiated Human Skin Cells.

Normal adult human keratinocytes (NHK) cells (Invitrogen, Vic, Australia) were cultured in keratinocyte growth medium Epilife supplemented with calcium and human keratinocyte growth supplement (HKGS, containing 0.2 ng EGF per mL, 5 mg insulin per mL, 5 mg transferrin per mL, 0.18 mg hydrocortisone per mL, and 0.2% bovine pituitary extract) (Invitrogen, Vic, Australia) in 12-well culture plates until the subconfluent state is reached. Cells were cultured to a density of $5\times10^3$ cells per mL/well in a 24-well plate for 24 h at 37° C. in a humidified incubator with 5% carbon dioxide and tested according to the protocols described below:

Determination of Optimal Doses of UV Irradiation.

Cells, seeded at a density as described above, were washed twice with PBS (phosphate buffered saline) then irradiated with a range of UVA and UVB doses known as MED (minimal erythema dose, 1 MED=25.43/light intensity). Cells were replaced with growth medium and incubated for about 24 h at 37° C. in a humidified incubator with 5% carbon dioxide. Cell viability was measured using the MTS assay (CellTiter 96® AQ$_{ueous}$ One Solution Cell Proliferation Assay) (Promega, Vic Australia).

Rescue Assay.

Cells were washed twice with PBS, replaced with a thin layer of PBS, then irradiated with the optimal doses of UVA and UVB as determined above. Immediately after irradiation, cells were replaced with fresh culture medium containing the test samples at a range of concentrations, and further incubated in a humidified $CO_2$ incubator at 37° C. for 24 hr. Supernatants were collected and kept at −80° C. until determination of PGE2 and cytokines (IL1, 6, 8, 10 & 12) concentration using ELISA kits.

Protective Assay.

Cells were washed twice with PBS, replaced with a thin layer of PBS containing different concentrations of the test compounds then irradiated with optimal doses of UVA and UVB as determined above. Immediately after irradiation, cells were replaced with fresh culture medium and further incubated in a humidified $CO_2$ incubator at 37° C. for 24 h. Supernatants were be collected and kept at −80° C. until determination of PGE2 and cytokines (IL1, 6, 8, 10 & 12) concentration using ELISA kits.

Sham-treated control cultures were handled identically but not exposed to UV irradiation. Stilbenes compounds including USYDS1, 2, 13, 5, and 7 and propolis extract were tested at 0.1, 1 and 10 µM or µg/mL.

Results for the determination of optimal doses of UV irradiation revealed that at 1 MED of UVA and UVB irradiation, there is no significant effect on cell viability. Thus, this condition was chosen for investigation of the effects of stilbenes and propolis extract on levels of cytokines in the rescue assay.

In preliminary investigation on modulation of cytokine productions in UV irradiated human epidermal keratinocytes (HEK) it was observed that a mixture of USYDS1 and USYDS2 moderately inhibit the production of IL-6, TGFα, G-CSF and GM-CSF (2-3 fold). However, it was found that the prenylated polyhydroxystilbene derivatives significantly increased IL-8 and IL-1rα production (4-5 fold) from UV irradiated cells. IL-8 is known to play a role in the onset of immunity response. IL-1rα (naturally occurring cytokine receptor antagonist) on the other hand plays an important role in inhibition of deleterious effect of IL-1 during inflammatory processes. Therefore, these preliminary results demonstrate that the prenylated polyhydroxystilbene derivates of the present invention may be good candidates for the treatment of conditions associated with immunity suppression and inflammation.

4. Antioxidant Activities of the Stilbenes and Propolis Extracts 1,1-Diphenyl-2-picrylhydrazyl (DPPH*) Scavenging Activity Assay The (1,1-diphenyl-2-picrylhydrazyl) DPPH assay is commonly used to test free radical scavenging ability of a compound or extracts of natural products by measurement of the reduction of DPPH* radicals at 517 nm. In its radical form, DPPH* shows a strong absorption at 517 nm due to its odd electron. Upon reduction by an antioxidant or radical scavenger, the absorption disappears and the resulting decolorization by scavenging the radical is stoichiometric with respect to the number of electrons taken up (DPPH*+AH→DPPH:H+A*). The DPPH assay was carried out in a stepwise procedure as described below.

Figure 10:
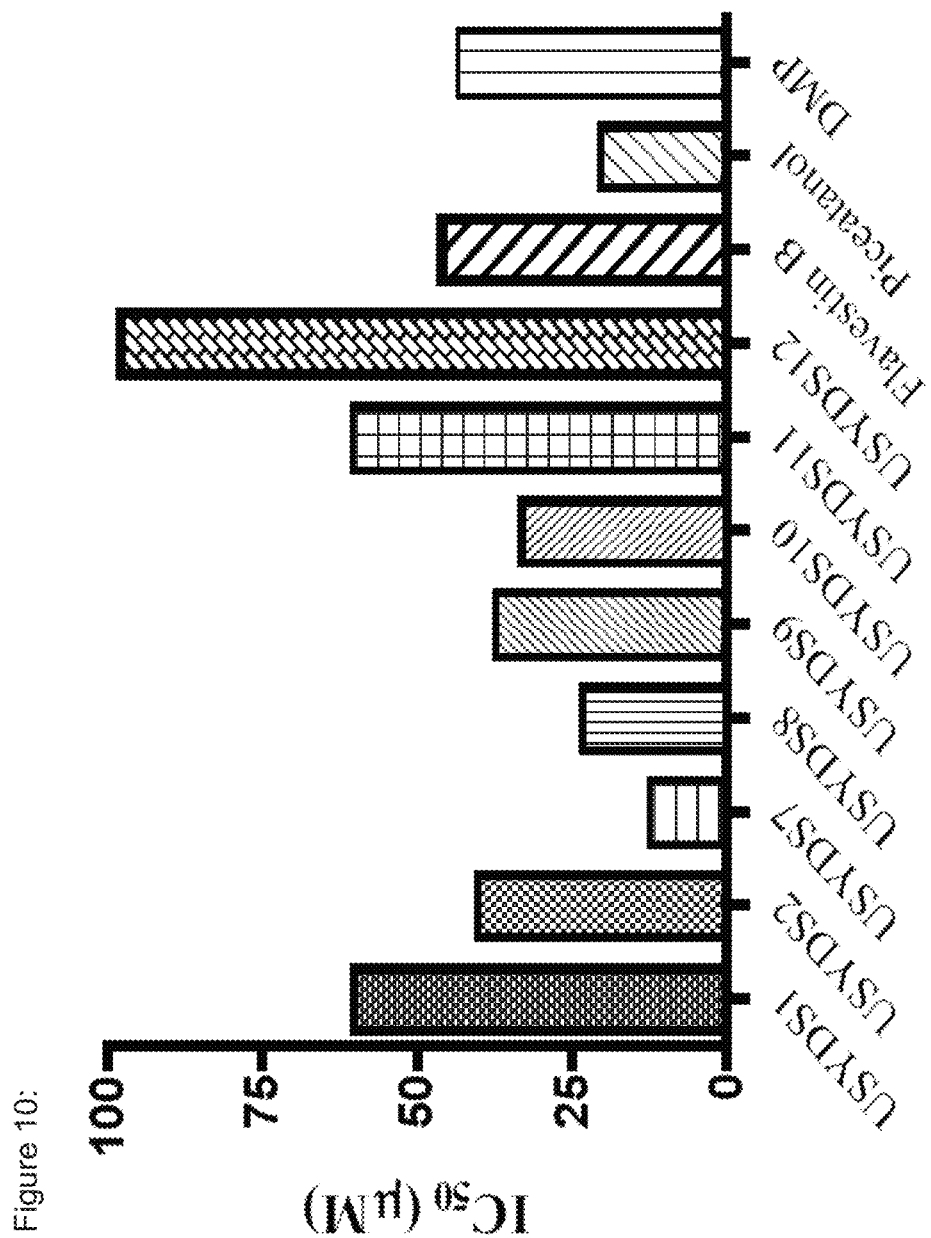
FIG. 10. graphically represents the effect of stilbene compounds on free radical scavenging.

A methanolic solution of DPPH (0.1 mM) was stirred in a dark container at room temperature for 20 min. The solution was scanned between 400-750 nm to obtain a maximum wavelength (λmax, ~510 nm). The concentration of the DPPH solution was adjusted with methanol to result in a maximum absorbance of approximately 1.0. Test samples at different concentrations and standard antioxidant solution (0.05 mL) were added to 0.95 mL of methanolic DPPH solution in a cuvette. Final concentrations of the test samples were 0.1, 1, 10, 50, 100 and 200 µM. The mixtures were shaken vigorously and allowed to stand in the dark for 30 min at room temperature. Absorbance of the resulting solution was measured at the maximum wavelength (~510 nm). A decrease in absorbance indicated a free radical scavenging effect of the test samples. Dose response curves of the test samples were established to determine their $IC_{50}$ values (concentrations that show 50% reduction in UV absorbance).
Results pPHOS compounds in this study exhibited a moderate to weak effect on free radical scavenging except for USYDS7 which exhibited a strong effect. These results are displayed in FIG. 10.

5. Effect of Stilbene Derivatives on Nicotinamide Adenine Dinucleotide (NAD)-Dependent Deacetylase Sirtuin-2 (SIRT1).

SIRT1 is a member of Sir2 family (class III) which is a NAD-dependent histone deacetylase. Deacetylation by SIRT1 enzyme can target many substrates including histone, tumor suppressor p53, forkhead transcription factor (FOXO), peroxisome proliferator-activated receptor-γ (PPARγ) and co-activator-1α (PGC-1α).[10] SIRT1 has been shown to be involved in the regulation of many physiopathological processes like inflammation, cellular aging, apoptosis/proliferation, metabolism and cell cycle regulation (Chung, Yao et al. 2010). Accordingly, modulating SIRT1 activity could be a potential therapeutic target to control many diseases such as cancer, metabolic syndrome, obesity, neurodegenerative disorder, skeletal muscle dysfunction and aging-related diseases.[11]

Figure 11:
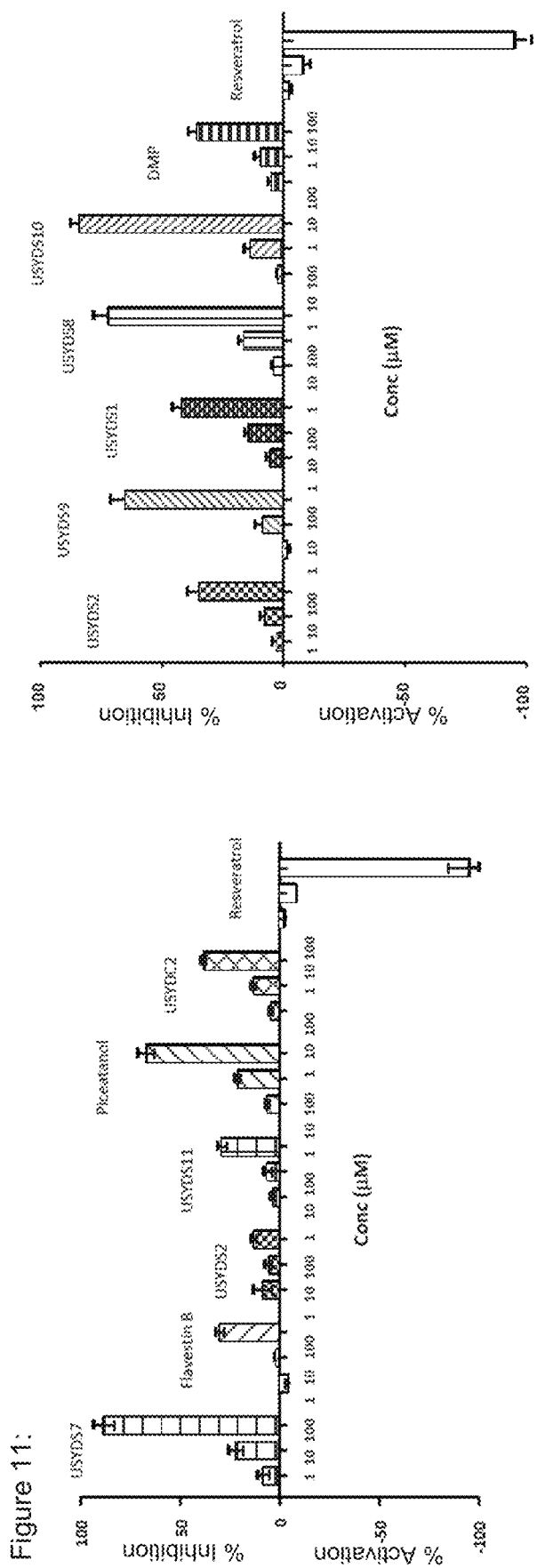
FIG. 11. graphically represents the concentration dependent inhibition of the NAD-dependent deacetylase sirtuin-2 (SIRT1) enzyme by stilbene compounds.

SIRT1 assay kit (Cayman Chemical, Ann Arbor, Mich., USA) provides a fluorescence-based method for screening of SIRT1 inhibitors or activators. The assay was carried out according to the instructions from the manufacturer. In brief, the assay consists of two steps, both performed in the same plate. In the first step, the substrate, which comprises the p53 sequence Arg-His-Lys-Lys(ε-acetyl)-AMC (7-amino-4-methylcoumarin), is incubated with human recombinant SIRT1 along with its cosubstrate $NAD^+$. Deacetylation sensitizes the substrate such that treatment with the developer in the second step releases a fluorescent product which was analysed using fluorometric plate reader at an excitation wavelength of 350-360 nm and an emission wavelength of 450-465 nm. Stilbenes were assayed at three concentrations (1, 10 and 100 µM). Data represents two independent experiments each performed in triplicate.
Results All the stilbenes, except resveratrol, exhibited a concentration dependent inhibition of SIRT1 as shown in FIGS. 11 A and B. Modulation of SIRT1 activity could lead to the development of therapeutic agents for the treatment of diseases including cancer, metabolic syndrome, obesity, neurodegenerative disorder, and aging-related diseases.

6. Antibacterial Activities of USYDS1, USYDS2 and Ethanolic Extract of Sedge Type-1 Propolis
Summary.

The minimum inhibition concentration (MIC) screening was performed with 14 bacterial strains and 4 compounds. The MICs were determined by the broth microdilution method according to the Clinical and Laboratory Standards Institute (CLSI) guidelines. The MIC screening was performed on 96-well plates containing the compounds in serial 2-fold dilutions from 64 to 0.06 µg/ml. The bacterial inoculations were prepared in cation-adjusted Mueller Hinton medium broth from cultures grown on appropriate agar plates which are prepared freshly every week. The growth controls and sterile controls were included in each assay plates. The assay plates were incubated in an ambient-air incubator at 35±2° C. for 16-20 hr (24 hr for MRSA), and bacterial growth was observed and recorded. All MICs of reference compound levofloxacin in the MIC screening are within the standard range described in CLSI S100-A20. The potency of 3 test samples is the order of USYDS1>USYDS2>ethanolic propolis extract.

1. Materials
1.1. Strains
Bacteria Panel for MIC Screening

| Microorganism | Gram | Strain | [1]Resistance | [2]Plasmid | Cultivation condition | MIC screening condition |
|---|---|---|---|---|---|---|
| Escherichia coli | G⁻ | ATCC (25922) | | | TSA, ambient air, 35 ± 2° C. | CAMHB, ambient air, 35 ± 2° C., 20 hr |
| Pseudomonas aeruginosa | G⁻ | ATCC (27853) | | | TSA, ambient air, 35 ± 2° C. | CAMHB, ambient air, 35 ± 2° C., 20 hr |
| Klebsiella pneumoniae | G⁻ | ATCC (700603) | AMP, AZT, CFX, CPD, CAZ, CHL, PIP, TET | Yes | TSA, ambient air, 35 ± 2° C. | CAMHB, ambient air, 35 ± 2° C., 20 hr |
| Haemophilus influenzae | G⁻ | ATCC (49247) | | | Chocolate agar, 5% $CO_2$, 35 ± 2° C. | HTM, ambient air, 35 ± 2° C., 20 hr |
| Acinetobacter calcoaceticus | G⁺ | ATCC (51432) | IMI | | TSA, ambient air, 35 ± 2° C. | CAMHB, ambient air, 35 ± 2° C., 20 hr |
| Enterococcus faecium | G⁺ | ATCC (700221) | VAN | | TSA +5% sheep blood, ambient air, 35 ± 2° C. | CAMHB, ambient air, 35 ± 2° C., 20 hr |
| Enterococcus faecalis | G⁺ | ATCC (29212) | | | TSA + 5% sheep blood, ambient air, 35 ± 2° C. | CAMHB, ambient air, 35 ± 2° C., 20 hr |
| Streptococcus pyogenes | G⁺ | ATCC (700492) | | | TSA + 5% sheep blood, 5% $CO_2$, 35 ± 2° C. | CAMHB + 3% horse blood, ambient air, 35 ± 2° C., 20 hr |
| Streptococcus pneumoniae | G⁺ | ATCC (49619) | PEN | | TSA + 5% sheep blood, 5% $CO_2$, 35 ± 2° C. | CAMHB + 3% horse blood, ambient air, 35 ± 2° C., 20 hr |

-continued

| Microorganism | Gram | Strain | ¹Resistance | ²Plasmid | Cultivation condition | MIC screening condition |
|---|---|---|---|---|---|---|
| Streptococcus pneumoniae | G⁺ | Clinical isolate | ERY | | TSA + 5% sheep blood, 5% $CO_2$, 35 ± 2° C. | CAMHB + 3% horse blood, ambient air, 35 ± 2° C., 20 hr |
| Staphylococcus aureus | G⁺ | ATCC (29213) | | | TSA, ambient air, 35 ± 2° C. | CAMHB, ambient air, 35 ± 2° C., 20 hr |
| Staphylococcus aureus | G⁺ | ATCC (43300) | MET, OXA | | TSA, ambient air, 35 ± 2° C. | CAMHB, ambient air, 35 ± 2° C., 20 hr |
| Staphylococcus aureus | G⁺ | Clinical isolate | LEV | | TSA, ambient air, 35 ± 2° C. | CAMHB, ambient air, 35 ± 2° C., 20 hr |
| Staphylococcus aureus | G⁺ | Clinical isolate | MET, ERY, CLI | | TSA, ambient air, 35 ± 2° C. | CAMHB, ambient air, 35 ± 2° C., 20 hr |

[1]Known resistance;
[2]Known plasmid presence

Abbreviation

TSA, trypticase soy agar; CAMHB, cation-adjusted Mueller Hinton broth; HTM, *Haemophilus* test medium; AMP, ampicillin; AZT, aztreonam; CFX, cefoxitin; CPD, cefpodoxime; CAZ, ceftazidime; CHL, chloramphenicol; PIP, piperacillin; TET, tetracycline; IMI, imipenem; VAN, vancomycin; PEN, penicillin; ERY, erythromycin; MET, methicillin; OXA, oxacillin; LEV, levofloxacin; CLI, clindamycin.

1.2. Media and Reagents

Trypticase soy agar (BD 211043), Cation-adjusted Mueller Hinton broth (BD 212322), *Haemophilus* test medium base (Fluka 51295), Hemin (Fluka 51280), β-NAD (Fluka 43410), Levofloxacin (Sigma 28266), Sheep blood (Quad Five 630-500), Lysed horse blood (Quad Five 205-500), 0.5 McFarland barium sulfate standard, Sterile 0.85% NaCl (w/v).

2. Methods 2.1. Prepare Bacterial Strains

A. Revive bacterial strains from storage frozen (−80° C.) two days before the MIC screening. Streak onto surface of appropriate agar plates, and incubate the plates for 20-24 hr at 35±2° C. in an appropriate atmosphere.
Streptococci: TSA II, 5% $CO_2$
Enterococci: TSA II, ambient air
*Haemophilus influenzae*: chocolate agar, 5% $CO_2$
Other strains in the panel: TSA, ambient air B. Select 5-10 well-isolated colonies of similar morphology and restreak onto fresh agar plates using sterile loops. Incubate the plates for 20-24 hr at 35±2° C. in an appropriate atmosphere as above.

2.2. Prepare Compound Plates

Compound stock solutions were prepared in 100% DMSO on the day of MIC screening and use immediately. Compound stock concentration=[(highest testing concentration)×10³ µl/3 µl] (e.g. if the required highest testing concentration is 64 µg/ml in assay plates, stock concentration=64×10³/3=2.2 mg/ml). The potency of testing compound is assumed as 100% unless otherwise stated whereas the potency of reference compound is calculated according to manufacturer's analysis data.

Eleven two-fold dilutions per compound were made then transferred 3 µl to each well of test plate. Final concentration of DMSO in the MIC screening is ~3%.

2.3. Prepare Bacterial Inoculation

A. Take out medium broth from 4° C. fridge and allow it to warm to room temperature.

B. Transfer colonies from fresh culture plates into 5 ml of saline with sterile loops and mix well. Measure and adjust turbidity to 0.5 McFarland barium sulphate standard using a turbidity meter. Alternatively, transfer 1-2 colonies into 500 µl of saline and adjust OD625 to ~0.1 using a plate reader.

C. Dilute bacterial inoculum 1:280 for Gram-positive and fastidious strains and 1:400 for Gram-negative strains into corresponding medium broth (CAMHB, CAMHB+3% lysed horse blood, HTM) (e.g. 35.6 µl of inoculum into 10 ml of CAMHB or 25 µl of inoculum into 10 ml of CAMHB).
*H. influenzae*: HTM
Streptococci: CAMHB+3% lysed horse blood
Other strains in the panel: CAMHB 2.4. Prepare Assay Plates A. Add 100 µl of the bacterial inoculum to each well of the compound plates except wells B12, D12, F12 and H12.
B. Add 100 µl of medium broth to wells B12, D12, F12 and H12 of the compound plates.
C. Stack four plates together and cover with a sterile plate lid. Incubate in an ambient-air incubator at 35±2° C. for 16-20 hours (24 hours for MRSA).

2.5. Perform Colony Counts

A. Dilute the bacterial inoculum (0.5 McFarland) to a serial of 10-1 to 10-7 in saline solution (e.g. 100 µl bacterial inoculum+900 µl of saline).
B. Spread 100 µl of each dilution (10-4, 10-5, 10-6, and 10-7) onto CAMHA plates in triplication, let the liquid soak into the agar for 10 minutes, invert the agar plates and incubate for 24 hr at 35±2° C.

2.6. Record MICs and Calculate CFUs

A. Open the compound plate layout in the compound management system, and check the assay plate barcode.
B. Place the assay plate on the top of MIC reader, and adjust the magnification mirror to read each wells, record growth status as raw data. (Optional) Record photo image of each assay plates using high-speed high-resolution scanner.
C. Determine MIC break points according to CLSI guideline.
D. Count colonies and calculate CFU of bacterial inoculum.

3. Results 3.1. MIC Summary Table

The MIC screening was performed with 14 bacterial strains (11 ATCC strains and 3 clinical isolates) and 4 compounds (USYDS1, USYDS2 and ethanolic extract of propolis and reference compound levofloxacin). The MICs are summarized in the below Table 6. The MIC values of reference compound Levofloxacin obtained in this study are within the standard range as described in S100-A20 [2]. The final concentration of DMSO in the MIC screening was ~3%, and did not inhibit the growth of most microorganisms.

TABLE 6

MICs (μg/ml) of USYDS1, USYDS2 and ethanolic extract of propolis against fourteen bacterial strains. Levofloxacin is reference compound.

| | Compounds | | | | | | | |
|---|---|---|---|---|---|---|---|---|
| | Levofloxacin | | USYDS1 | | USYDS2 | | Ethanolic propolis extract | |
| | Exp 1 | Exp 2 | Exp 1 | Exp 2 | Exp 1 | Exp 2 | Exp 1 | Exp 2 |
| *Acinetobacter calcoaceticus* | 4 | 4 | >64 | >64 | >64 | >64 | >64 | >64 |
| *Escherichia coli* | <0.0625 | <0.0625 | 16 | 16 | 64 | 32 | >64 | >64 |
| *Enterococcus faecalis* (ATCC 29212) | 1 | 1 | 16 | 16 | 32 | 32 | 64 | 64 |
| *Enterococcus faecium* (ATCC 700221) | >64 | >64 | 8 | 16 | 32 | 32 | 64 | 32 |
| *Haemophilus influenzae* | <0.0625 | <0.0625 | 32 | 32 | 32 | 32 | 64 | 64 |
| *Klebsiella pneumoniae* | 1 | 1 | >64 | >64 | >64 | >64 | >64 | >64 |
| *Pseudomonas aeruginosa* | 1 | 1 | >64 | >64 | >64 | >64 | >64 | >64 |
| Staphylococcus aureus (ATCC 29213) | 0.5 | 0.25 | 16 | 8 | 32 | 16 | 32 | 32 |
| Staphylococcus aureus (ATCC 43300) | 0.25 | 0.25 | 8 | 8 | 16 | 16 | 32 | 32 |
| Staphylococcus aureus (Levofloxacin-resistant) | 64 | 64 | 8 | 8 | 16 | 16 | 16 | 16 |
| Staphylococcus aureus (MRSA, Erythromycin & clindamycin-resistant) | 8 | 8 | 8 | 8 | 16 | 16 | 32 | 32 |
| *Streptococcus pneumoniae* (ATCC 49619) | 0.5 | 0.5 | 32 | 32 | 32 | 32 | 32 | 32 |
| *Streptococcus pyogenes* (ATCC 700942) | 0.5 | 0.5 | 64 | 64 | 64 | 64 | >64 | >64 |
| *Streptococcus pneumoniae* (Erythromycin-resistant) | 1 | 1 | 32 | 32 | 32 | 64 | 64 | >64 |

4. Discussion

The prenylated tetrahydroxystilbenes USYDS1 and USYDS2 showed a moderate antibacterial activities with the rank of potency of USYDS1>USYDS2>ethanolic extract of propolis.

7. The Effect of USYDS1, USYDS2 and USYDS10 Compounds on Kinases Activities

The following is a list of kinases in the studied.

| No. | Kinase |
|---|---|
| 1 | ABL2 |
| 2 | AKT1 |
| 3 | AKT2 |
| 4 | AKT3 |
| 5 | ALK1 |
| 6 | AMPK (A1/B1/G1) |
| 7 | AMPK (A2/B1/G1) |
| 8 | Aurora A |
| 9 | Aurora B |
| 10 | Aurora C |
| 11 | AXL |
| 12 | BLK |
| 13 | BTK |
| 14 | CAMK1 |
| 15 | CDK1/CyclinA2 |
| 16 | CDK1/CyclinB |
| 17 | CDK2/CyclinA2 |
| 18 | CDK3/CyclinE1 |
| 19 | CDK4/CyclinD1 |
| 20 | CDK4/CyclinD3 |
| 21 | CDK5/CyclinP25 |
| 22 | CDK6/CyclinD1 |
| 23 | CDK6/CyclinD3 |
| 24 | CDK7/CyclinH1/MNAT1 |
| 25 | CHK1 |
| 26 | c-KIT |
| 27 | c-KIT(V654A) |
| 28 | EGFR(T790M, L858R) |
| 29 | EphA1 |
| 30 | EphA2 |
| 31 | EphA3 |
| 32 | EphA4 |
| 33 | EphB1 |
| 34 | EphB2 |
| 35 | EphB3 |
| 36 | ERK1 |
| 37 | FGFR1(V561M) |
| 38 | FGFR2 |
| 39 | FGFR3 |
| 40 | FGR |
| 41 | FLT1 (VEGFR1) |
| 42 | FLT3 |
| 43 | GSK3α |
| 44 | HER2 |
| 45 | IGF1R |
| 46 | InsR |
| 47 | KDR |
| 48 | LCK |
| 49 | NEK2 |
| 50 | p38β |
| 51 | PDGFRβ |
| 52 | PI3Kα |
| 53 | PI3Kβ |
| 54 | PI3Kγ |
| 55 | PI3Kδ |
| 56 | PKAcα |
| 57 | PKAcβ |
| 58 | PKAcγ |
| 59 | PKCα |
| 60 | PKCβ1 |
| 61 | PKCγ |

| No. | Kinase |
|---|---|
| 62 | PKCε |
| 63 | PKCθ |
| 64 | PKCδ |
| 65 | PKCδ |
| 66 | PKC$_L$ |
| 67 | PLK2 |
| 68 | PLK3 |
| 69 | RAF1 |
| 70 | BRAF |
| 71 | BRAF(v599E) |
| 72 | RET |
| 73 | RON |
| 74 | SRC |
| 75 | TrkA |
| 76 | TrkB |

EXPERIMENTS

Materials:
Kinase-Glo(Plus)/ADP-Gloassay buffer
25 mMHEPES, 10 mMMgCl2, 0.01% Triton X-100, 100 µg/mLBSA, 2.5 mMDTT, pH7.4.
Caliper assay buffer
100 mMHEPES, 10 mMMgCl2, 100 µl/L Brij35 (30%), 1 mMDTT, pH7.4.
Assay Substrates
  MBP protein, UnactiveMEK1, Rbprotein were purchased from SignalChem.
Poly(glu:tyr)(4:1) was purchased from Sigma. PIP2 was purchased from Cayman.
Peptide substrates were synthesized in HD Biosciences, China.
ATP was purchased from Sigma. KinaseGloPlus reagent, KinaseGloreagent and ADP Gloreagent were purchased from Promega
Assay Procedure—Caliper Format
  Mix Kinases, substrate, ATP and compound in 96-well assay plate, total volume is 50 µL. Incubate assay plate at 30° C. for 1 hour. Stop reaction by adding 20 µL of 35 mM EDTA and transfer 26 µL stopped reaction to 384-well assay plate. Read the assay plate on the plate reader.
Assay Procedure—ADP-GloFormat
  Mix Kinases, substrate, ATP and compound in 384-well assay plate, total volume is 10 µl. Incubate assay plate at 30° C. for 1 hour. Add 10 µl/well of ADP GloReagent to the assay plate, incubate at 27° C. for 40 min.
  Add 20 µl/well Detection Reagent to the assay plate, incubate at 27° C. for 30 min. Read the assay plate on the plate reader
Assay Procedure—Kinase-Glo(Plus)Format
  Mix Kinase, substrate, ATP and compound in 384-well assay plate, total volume is 10 µl. Incubate assay plate at 30° C. for 1 hour. Add 10 µl/well KinaseGlo(Plus) reagent to the reaction mixture, and then incubate at 27° C. for 20 min. Read the assay plate on plate reader.
  Hundred percent effect was performed without compound and enzyme, but containing ATP and substrate.
  Zero percent effect was carried out without compound, but containing ATP, substrate and enzyme.
  SB202190 is reference compounds for kinase p38β; Staurosporine(STSP) is reference compound for the remaining kinases.
Results
  Kinases that inhibited more than 60% are summarised in the table below. It is interesting to note that all three compounds inhibited kinases TrKA and PI3Kδ and PI3Kγ. Both USYDS1 and USYDS10 appear to display similar inhibitory activities towards the kinases.

| Compound | Kinases |
|---|---|
| USYDS1 | FLT3, TrkA, CDK2/CyclinA2, CDK4/CyclinD3, PI3Kα, PI3Kδ, PI3Kγ |
| USYDS2 | TrkA, PI3Kβ, PI3Kδ, PI3Kγ |
| USYDS10 | FLT3, TrkA, KDR, FLT1, CDK2/CyclinA2, PI3Kα, PI3Kβ, PI3Kδ, PI3Kγ, CDK1/CyclinB |

8. Acute Toxicity Study of USYDS1
Method
  A single mouse is given a single IP injection of 400 mg/kg; a second mouse receives a dose of 200 mg/kg IP and a third mouse receives a single dose of 100 mg/kg IP. The mice are observed for a period of 2 weeks. They are sacrificed if they lose more than 20% of their body weight or if there are other signs of significant toxicity. If all 3 mice must be sacrificed, then the next 3 dose levels (50, 25, 12.5 mg/kg) are tested in a similar way. This process is repeated until a tolerated dose is found. This dose is then designated the maximum tolerated dose (MTD) and is used to calculate the amount of material given to experimental mice during anti-tumor testing. The mice are allowed ad libitum feed and water. Drug was dissolved in 100% DMSO at concentration of 200 mg/mL.
Result

| Group | Dose (mg/kg/dose) | Route | Death days | Survivor/Total day 15 | Injection volume |
|---|---|---|---|---|---|
| 1 | 100 | IP | None | 1/1 | 0.5 µL/gm body wt |
| 2 | 200 | IP | 1 | 0/1 | 1 µL/gm body wt |
| 3 | 400 | IP | 1 | 0/1 | 2 µL/gm body wt |

The MTD of USYDS1 was determined as 100 mg/kg. This concentration indicates low mammalian toxicity and is being used for further anti-tumor testing. Hollow fiber assay (BEC/C) for USYDS1 is under progression. The hollow fibre assay is a preliminary rapid screen for assessing novel putative chemotherapeutic compounds against a range of cancer cell lines prior to their evaluation in the mouse xenograft model. The hollow fiber model has a shorter evaluation time and a reduced compound requirement compared to traditional xenograft models. The model allows for the effective selection of cancer cell types in the xenograft.
Chemotypes of Plants that Produce Resins as Sources of Prenylated Polyhydroxystilbene Derivatives
  Resins, gums or exudates obtained from plants of the *Lepidosperma* genus from different locations were analysed by quantitative $^1$H-NMR (q-NMR) for prenylated polyhydroxystilbene content, which include C- and O-prenylated, O-methylated and non-O-methylated derivatives. Different proportions of these prenylated polyhydroxystilbene derivatives from the resins form a basis to classify the plants accordingly.
  There are at least 3 different chemotypes of *Lepidosperma* plants identified thus far and each of these plants display several sub-chemotypes. Type 1 is the most common plant which contains approximately equal proportion of both C- and O-prenylated derivatives. Type 2 plant contains only C-prenylated derivatives. Where as, type 3 plant contains no O-methylated prenylated polyhydroxystilbene derivatives.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

REFERENCES (1) Denmark, E.; Regens, C. S.; Tetsuya, K. *J. of Am. Chem. Soc.* 2007, 129, 2774-2276.
(2) Ali, I. A. I.; Fathalla, W. *Heteroatom Chemistry* 2006, 17, 280-288.
(3) Krohn, K.; Thiem, J. *J. Chem. Soc., Perkin Trans.* 1 1977, 1186-1190.
(4) Soerme, P.; Arnoux, P.; Kahl-Knutsson, B.; Leffler, H.; Rini, J. M.; Nilsson, U. J. *J. Am. Chem. Soc.* 2005, 127, 1737-1743.
(5) Andrus, M. B.; Liu, J.; Meredith, E. L.; Nartey, E. *Tetrahedron Lett.* 2003, 44, 4819-4822.
(6) Rao, M. L. N.; Awasthi, D. K.; Banerjee, D. *Tetrahedron Lett.* 2010, 51, 1979-1981.
(7) Yang, P.-Y.; Zhou, Y.-G. *Tetrahedron Asymmetry* 2004, 15, 1145-1149.
(8) Rooney, J. M. *Journal of Macromolecular Science, Part A* 1986, 23, 823-829.
(9) Batsomboon, P.; Phakhodee, W.; Ruchirawat, S.; Ploypradith, P. *J Org. Chem.* 2009, 74, 4009-4012.
(10) Michan, S.; Sinclair D. *Biochem. J.* 2007, 404, 1-13.
(11) Yamamoto H.; Schoonjans K.; Auwerx *J. Mol. Endocrinol.* 2007, 21, 1745-1755.

What is claimed is:

1. A method for treating cancer, comprising administering a therapeutically effective amount of a compound of formula (Ia):

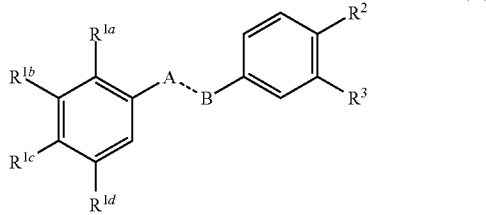

or pharmaceutically acceptable salts or solvates thereof, wherein:
$R^{1a}$ is selected from, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;
$R^{1b}$ is selected from, H, OH, $OR^4$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;
$R^{1c}$ is selected from H, OH, $OR^{4a}$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;
$R^{1d}$ is selected from H, OH, $OR^4$, $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;

wherein at least one of $R^{1b-1d}$ is OH and at least one of $R^{1a-1d}$ is $CH_2CH=C(CH_3)_2$, $OCH_2CH=C(CH_3)_2$, $CH=CHCH(CH_3)_2$, $CH=CHC(CH_3)=CH_2$, $OCH=CHCH(CH_3)_2$, or $OCH=CHC(CH_3)=CH_2$;
$R^2$ is selected from OH, $OR^{4a}$, $OCH_2CH=C(CH_3)_2$, $CH=CHC(CH_3)=CH_2$, $OCH=CHCH(CH_3)_2$, or $OCH=CHC(CH_3)=CH_2$;
$R^3$ is selected from OH, $OR^4$, $OCH_2CH=C(CH_3)_2$, $CH=CHC(CH_3)=CH_2$, $OCH=CHCH(CH_3)_2$, or $OCH=CHC(CH_3)=CH_2$;
$R^4$ is selected from, methyl, ethyl, propyl, isopropyl, butyl, isobutyl, t-butyl or benzyl;
$R^{4a}$ is selected from, ethyl, propyl, isopropyl, butyl, isobutyl, t-butyl or benzyl; and
A----B is selected from CH=CH, CH=CH(CH_2)pCH_2, or $CH_2-CH_2(CH_2)pCH_2$, where p is an integer selected from the group consisting of 1 and 2.

2. A method according to claim 1, wherein the cancer is leukemia, non-small cell lung cancer, colon cancer, CNS cancer, melanoma, ovarian cancer, renal cancer, prostate cancer, or breast cancer.

3. A method according to claim 2 wherein the cancer is leukemia.

4. A method according to claim 2 wherein the cancer is melanoma.

5. A method according to claim 1, wherein two of $R^{1b-1d}$ are H.

6. A method according to claim 1, wherein one of $R^{1b-1d}$ is H.

7. A method according to claim 1, wherein none of $R^{1b-1d}$ are H.

8. A method according to claim 1, wherein at least one of $R^{1a-1d}$ is $CH_2CH=C(CH_3)_2$.

9. A method according to claim 1, wherein at least one of $R^{1a-1d}$ is $OCH_2CH=C(CH_3)_2$.

10. A method according to claim 1, wherein at least two of $R^{1b-1d}$ are OH.

11. A method according to claim 1, wherein $R^{1b}$ is $OR^4$ and $R^4$ is methyl.

12. A method according to claim 1, wherein at least one of $R^{1b-1d}$ is $OR^4$ or $OR^{4a}$ and $R^4$ or $R^{4a}$ is benzyl.

13. A method according to claim 1, wherein at least one of $R^2$ or $R^3$ is OH.

14. A method according to claim 1, wherein $R^3$ is $OR^4$ and $R^4$ is methyl.

15. A method according to claim 1, wherein both $R^2$ and $R^3$ are OH.

16. A method according to claim 1, wherein $R^3$ is $OR^4$ and $R^4$ is benzyl.

17. A method according to claim 1, wherein A----B is CH=CH or CH=CH(CH_2)pCH_2, where p is an integer selected from the group consisting of 1 and 2.

18. A method according to claim 1, wherein A----B is $CH_2-CH_2(CH_2)pCH_2$, and where p is an integer selected from the group consisting of 1 and 2.

19. A method according to claim 1, wherein the compound of formula (Ia) is formula (Ie):

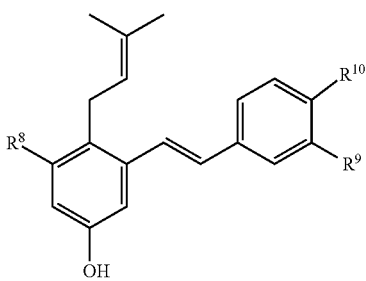

(1e)

wherein, $R^8$ and $R^9$ are each independently selected from the group consisting of OH, OMe, OEt, OPr, O$^i$Pr, OBu, O$^i$Bu, and O$^t$Bu, and wherein $R^{10}$ is OH.

20. A method according to claim 1, wherein the compound is chemically synthesised.

21. A method according to claim 1, wherein the compound originates from propolis, and wherein the propolis originates from plants of the *Lepidosperma* genus.

22. A method according to claim 1, wherein the compound originates from the resin, gum, or exudate of the *Lepidosperma* genus.

23. A method of claim 1, wherein the compound or pharmaceutically acceptable salt or solvate thereof is administered as a pharmaceutical composition which also comprises one or more pharmaceutically acceptable carriers, diluents, or excipients.

24. A method of claim 23, wherein the pharmaceutical composition includes one or more further therapeutic agents.

25. A method of claim 23, wherein the pharmaceutical composition is in the form of a parenteral solution, emulsion, or suspension.

* * * * *